US010017561B2

(12) United States Patent
Horowitz et al.

(10) Patent No.: US 10,017,561 B2
(45) Date of Patent: Jul. 10, 2018

(54) NEUTRALIZING MOLECULES TO INFLUENZA VIRUSES

(71) Applicant: I2 PHARMACEUTICALS, INC., Boulder, CO (US)

(72) Inventors: Lawrence Horowitz, Atherton, CA (US); Ramesh Bhatt, Belmont, CA (US); Arun Kashyap, Newark, CA (US)

(73) Assignee: I2 PHARMACEUTICALS, INC., Boulder, CO (US)

( * ) Notice: Subject to any disclaimer, the term of this patent is extended or adjusted under 35 U.S.C. 154(b) by 0 days.

(21) Appl. No.: 14/970,244

(22) Filed: Dec. 15, 2015

(65) Prior Publication Data

US 2016/0096882 A1    Apr. 7, 2016

Related U.S. Application Data

(63) Continuation of application No. 13/261,004, filed as application No. PCT/US2010/034604 on May 12, 2010.

(60) Provisional application No. 61/228,114, filed on Jul. 23, 2009, provisional application No. 61/177,987, filed on May 13, 2009.

(51) Int. Cl.
| | |
|---|---|
| *C07K 16/00* | (2006.01) |
| *C07K 16/10* | (2006.01) |
| *A61K 9/00* | (2006.01) |
| *A61K 39/145* | (2006.01) |
| *C12N 7/00* | (2006.01) |
| *A61K 39/00* | (2006.01) |

(52) U.S. Cl.
CPC ........ *C07K 16/1018* (2013.01); *A61K 9/0043* (2013.01); *A61K 9/0053* (2013.01); *A61K 39/145* (2013.01); *C12N 7/00* (2013.01); *A61K 2039/505* (2013.01); *A61K 2039/5252* (2013.01); *A61K 2039/5254* (2013.01); *A61K 2039/54* (2013.01); *A61K 2039/543* (2013.01); *A61K 2039/55* (2013.01); *C07K 2317/21* (2013.01); *C07K 2317/33* (2013.01); *C07K 2317/56* (2013.01); *C07K 2317/565* (2013.01); *C07K 2317/567* (2013.01); *C07K 2317/76* (2013.01); *C07K 2317/92* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 4,256,746 A | 3/1981 | Miyashita et al. | |
| 4,307,016 A | 12/1981 | Asai et al. | |
| 4,313,946 A | 2/1982 | Powell et al. | |
| 4,315,929 A | 2/1982 | Freedman et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,424,219 A | 1/1984 | Hashimoto et al. | |
| 4,439,196 A | 3/1984 | Higuchi | |
| 4,447,224 A | 5/1984 | De Cant et al. | |
| 4,447,233 A | 5/1984 | Mayfield | |
| 4,450,254 A | 5/1984 | Isley et al. | |
| 4,475,196 A | 10/1984 | La Zor | |
| 4,486,194 A | 12/1984 | Ferrara | |
| 4,487,603 A | 12/1984 | Harris | |
| 4,522,811 A | 6/1985 | Eppstein et al. | |
| 4,563,304 A | 1/1986 | Carlsson et al. | |
| 4,596,556 A | 6/1986 | Morrow et al. | |
| 4,683,192 A | 7/1987 | Nishiyama | |
| 4,683,202 A | 7/1987 | Mullis | |
| 4,790,824 A | 12/1988 | Morrow et al. | |
| 4,800,159 A | 1/1989 | Mullis et al. | |
| 4,816,567 A | 3/1989 | Cabilly et al. | |
| 4,941,880 A | 7/1990 | Burns | |
| 4,965,188 A | 10/1990 | Mullis et al. | |
| 5,064,413 A | 11/1991 | McKinnon et al. | |
| 5,182,205 A | 1/1993 | Bauer et al. | |
| 5,208,020 A | 5/1993 | Chari et al. | |
| 5,312,335 A | 5/1994 | McKinnon et al. | |
| 5,374,548 A | 12/1994 | Caras | |
| 5,383,851 A | 1/1995 | McKinnon, Jr. et al. | |
| 5,399,163 A | 3/1995 | Peterson et al. | |
| 5,399,331 A | 3/1995 | Loughrey et al. | |
| 5,416,016 A | 5/1995 | Low et al. | |

(Continued)

FOREIGN PATENT DOCUMENTS

| | | |
|---|---|---|
| EP | 0269127 A2 | 6/1988 |
| EP | 1396500 A1 | 3/2004 |

(Continued)

OTHER PUBLICATIONS

Johnson, George, and Wu, Tai Te. "The Kabat database and a bioinformatics example." Antibody Engineering: Methods and Protocols (2004); 248: 11-25.
U.S. Appl. No. 12/413,308 (abandoned).
U.S. Appl. No. 13/261,004 (abandoned).
U.S. Appl. No. 13/371,347 (abandoned).
U.S. Appl. No. 13/374,202 (abandoned).
U.S. Appl. No. 14/047,301 (pending).
U.S. Appl. No. 14/128,455 (pending).
U.S. Appl. No. 14/235,431 (pending).
U.S. Appl. No. 14/367,862 (pending).
U.S. Appl. No. 14/373,326 (abandoned).

(Continued)

*Primary Examiner* — Brad Duffy
(74) *Attorney, Agent, or Firm* — Cooley LLP

(57) ABSTRACT

The present invention concerns methods and means for identifying, producing, and engineering neutralizing antibodies against influenza A viruses, and to the neutralizing antibodies produced. In particular, the invention concerns neutralizing antibodies against various influenza A virus subtypes, and methods and means for making such antibodies.

11 Claims, 17 Drawing Sheets

(56) References Cited

U.S. PATENT DOCUMENTS

| | | | |
|---|---|---|---|
| 5,416,064 A | 5/1995 | Chari et al. |
| 5,427,908 A | 6/1995 | Dower et al. |
| 5,474,765 A | 12/1995 | Thorpe |
| 5,475,982 A | 12/1995 | Laude-Bousquet |
| 5,480,968 A | 1/1996 | Kraus et al. |
| 5,585,499 A | 12/1996 | Chari et al. |
| 5,622,929 A | 4/1997 | Willner et al. |
| 5,641,869 A | 6/1997 | Vandlen et al. |
| 5,762,918 A | 6/1998 | Thorpe |
| 5,824,805 A | 10/1998 | King et al. |
| 5,846,545 A | 12/1998 | Chari et al. |
| 6,333,410 B1 | 12/2001 | Chari et al. |
| 6,337,070 B1 | 1/2002 | Yoshinobu et al. |
| 6,441,163 B1 | 8/2002 | Chari et al. |
| 6,716,821 B2 | 4/2004 | Zhao et al. |
| 6,720,409 B2 | 4/2004 | Okuno et al. |
| 7,276,497 B2 | 10/2007 | Chari et al. |
| 7,473,796 B2 | 1/2009 | Chari et al. |
| 7,612,181 B2 | 11/2009 | Wu et al. |
| 8,114,967 B2 | 2/2012 | Bhatt et al. |
| 8,198,417 B2 | 6/2012 | Steeves et al. |
| 9,169,318 B2 | 10/2015 | Howowitz et al. |
| 2002/0054882 A1 | 5/2002 | Yoshinobu et al. |
| 2003/0198637 A1 | 10/2003 | Tong et al. |
| 2003/0215453 A1 | 11/2003 | Dedera et al. |
| 2005/0169933 A1 | 8/2005 | Steeves et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2006/0147997 A1 | 7/2006 | Ramakrishnan |
| 2007/0004909 A1 | 1/2007 | Johnson et al. |
| 2007/0191314 A1 | 8/2007 | Klucker et al. |
| 2008/0014205 A1 | 1/2008 | Horowitz et al. |
| 2008/0124345 A1 | 5/2008 | Rothe |
| 2009/0082213 A1 | 3/2009 | Horowitz et al. |
| 2009/0098164 A1 | 4/2009 | Bhatt et al. |
| 2009/0226455 A1 | 9/2009 | Filvaroff |
| 2009/0274713 A1 | 11/2009 | Chari et al. |
| 2010/0004139 A1 | 1/2010 | Bhatt et al. |
| 2010/0040635 A1 | 2/2010 | Horowitz et al. |
| 2010/0062950 A1 | 3/2010 | Bhatt et al. |
| 2010/0210034 A1 | 8/2010 | Bates |
| 2010/0255010 A1 | 10/2010 | Fuh |
| 2010/0297174 A1 | 11/2010 | Garcia-Sastre et al. |
| 2011/0256154 A1 | 10/2011 | Vincent et al. |
| 2012/0123098 A1 | 5/2012 | Bhatt et al. |
| 2012/0128671 A1 | 5/2012 | Howowitz et al. |
| 2012/0156217 A1 | 6/2012 | Setiady et al. |
| 2012/0202713 A1 | 8/2012 | Bhatt et al. |
| 2012/0294853 A1 | 11/2012 | McDonagh et al. |
| 2014/0228544 A1 | 8/2014 | Bhatt et al. |
| 2014/0308287 A1 | 10/2014 | Bhatt et al. |
| 2015/0004162 A1 | 1/2015 | Kashyap et al. |
| 2015/0011736 A1 | 1/2015 | Horowitz et al. |
| 2015/0045540 A1 | 2/2015 | Howowitz et al. |
| 2016/0354486 A1 | 12/2016 | Horowitz et al. |
| 2017/0136118 A1 | 5/2017 | Horowitz et al. |

FOREIGN PATENT DOCUMENTS

| | | |
|---|---|---|
| JP | 2011-516423 A | 5/2011 |
| WO | WO 1984/000687 A1 | 3/1984 |
| WO | WO 1997/016208 A1 | 5/1997 |
| WO | WO 2000/073349 A1 | 12/2000 |
| WO | WO 2001/035993 A2 | 5/2001 |
| WO | WO 2001/060402 A2 | 8/2001 |
| WO | WO 2002/030463 A2 | 4/2002 |
| WO | WO 2002/096457 A2 | 12/2002 |
| WO | WO 2004/003019 A2 | 1/2004 |
| WO | WO 2004/010957 A2 | 2/2004 |
| WO | WO 2006/065533 A2 | 6/2006 |
| WO | WO 2007/077028 A2 | 7/2007 |
| WO | WO 2007/134327 A2 | 11/2007 |
| WO | WO 2008/028946 A2 | 3/2008 |
| WO | WO 2008/089073 A2 | 7/2008 |
| WO | WO 2008/100624 A2 | 8/2008 |
| WO | WO 2008/118970 A2 | 10/2008 |
| WO | WO 2008/153236 A1 | 12/2008 |
| WO | WO 2009/021754 A2 | 2/2009 |
| WO | WO 2009/079259 A2 | 6/2009 |
| WO | WO 2009/121004 A2 | 10/2009 |
| WO | WO 2009/134976 A1 | 11/2009 |
| WO | WO 2010/006286 A2 | 1/2010 |
| WO | WO 2010/132604 A2 | 11/2010 |
| WO | WO 2010/151808 A1 | 12/2010 |
| WO | WO 2011/071957 A1 | 6/2011 |
| WO | WO 2011/112955 A1 | 9/2011 |
| WO | WO 2011/143307 A1 | 11/2011 |
| WO | WO 2011/153431 A2 | 12/2011 |
| WO | WO 2013/003652 A1 | 1/2013 |
| WO | WO 2013/016714 A1 | 1/2013 |
| WO | WO 2013/096828 A1 | 6/2013 |
| WO | WO 2013/109994 A1 | 7/2013 |

OTHER PUBLICATIONS

U.S. Appl. No. 14/924,467 (abandoned).
U.S. Appl. No. 14/979,114 (pending).
U.S. Appl. No. 15/177,232 (pending).
Abbas, Cellular and Molecular Immunology, 4th Ed., Chapter 7, p. 144.
Ada, G.L. and Jones, P.D. "The Immune response to influenza infection", Current topics in Microbiology and Immunology (1986); 128: 1-54.
Adams, Camellia W., et al. "Humanization of a recombinant monoclonal antibody to produce a therapeutic HER dimerization inhibitor, pertuzumab." Cancer Immunology, Immunotherapy (2006); 55.6: 717-727.
Ashkenazi, A., "Directing cancer cells to self-destruct with pro-apoptotic receptor agonists", Nat. Rev. Drug Discov. (2008); 7: 1001-1012.
Bankovich et al. "Structural insight into pre-B cell receptor function", Science (2007); 316: 291-294.
Bendig, Mary M., "Humanization of Rodent Monoclonal Antibodies by CDR grafting." Methods: Companion to Methods in Enzymology (1995); 8.2: 83-93.
Bowie, James U., et al. "Deciphering the message in protein sequences: tolerance to amino acid substitutions." Science (1990); 247.4948: 1306-1310.
Brummell, David A., et al. "Probing the combining site of an anti-carbohydrate antibody by saturation-mutagenesis: role of the heavy-chain CDR3 residues." Biochemistry (1993); 32.4: 1180-1187.
Burks et al., "In vitro scanning saturation mutagenesis of an antibody binding pocket", PNAS 94: 412-417, (1997).
Carlsson et al., "Protein Thiolation and Reversible Protein-Protein Conjugation", Biochem. J., 173:723-737 (1978).
Casset et al. "A peptide mimetic of an anti-CD4 monoclonal antibody by rational design", Biochemical and Biophysical Research Communications (2003); 307: 198-205.
Chen et al. "Selection and analysis of an optimized anti-VEGF antibody: Crystal structure of an affinity-matured Fabin complex with Antigen", Journal of Molecular Biology (1999); 293: 865-881.
Chumsae, et al., "Comparison of methionine oxidation in thermal stability and chemically stressed samples of a fully human monoclonal antibody", Journal of Chromatography (2007); 850: 285-294.
Colman, "Effects of amino acid sequence changes on antibody-antigen interactions", Research in Immunol. (1994); 145: 33-36.
Collins et al. "A genome annotation-driven approach to cloning the human ORFeome", Genome Biology (2004); 5(10): R84, Epub Sep. 30, 2004.
Colman et al., "Structure of the catalytic and antigenic sites in influenza virus neuraminidase", Nature (1983); 303: 41-44.
Couch and Kasel, "Immunity to influenza in man", Annual Reviews in Microbiology (1983); 37.1: 529-549.
Daniel, Claude, et al. "Mapping of linear antigenic sites on the S glycoprotein of a neurotropic murine coronavirus with synthetic peptides: a combination of nine prediction algorithms fails to

(56) References Cited

OTHER PUBLICATIONS identify relevant epitopes and peptide immunogenicity is drastically influenced by the nature of the protein carrier." Virology (1994); 202.2: 540-549.
Database UniProt (online) Immunoglobulin lambda-like polypeptide 1, XP002498605 (1990), 3 pages.
Davies and Riechmann, "Affinity improvement of single antibody VH domains: residues in all three hyper variable regions affect antigen binding", Immunotechnology (1996); 2.3: 169-179.
De Pascalis et al. "Grafting of "Abbreviated" complementarity-determining regions containing specificity-determining residues essential for ligand contact to engineer a less immunogenic humanized monoclonal antibody", The Journal of Immunology (2002); 169: 3076-3084.
Dubowchik and Walker, "Receptor-mediated and enzyme-dependent targeting of cytotoxic anticancer drugs", Pharm. Therapeutics 83:67-123 (1999).
Extended European Search Report for European Application No. EP 13177665.0, dated Jan. 16, 2014, 14 pages.
Foreman, et al., "ErbB3 Inhibitor Surrobodies inhibit Tumor Cell Proliferation In Vitro and In Vivo", Molecular Cancer Therapeutics (2012); 11.7: 1411-1420.
Francés et al. "A surrogate 15 kDa JC kappa protein is expressed in combination with mu heavy chain by human B cell precursors", EMBO Journal (1994); 13: 5937-5943.
Franklin, Matthew C., et al. "Insights into ErbB signaling from the structure of the ErbB2-pertuzumab complex." Cancer Cell (2004); 5.4: 317-328.
Friedman et al. "Engineering and characterization of a bispecific HER2 × EGFR-binding affibody molecule", Biotechnology and Applied Biochemistry (2009); 54(2): 121-131.
Gauthier et al. "U-surrogate light chain physicochemical interactions of the human preB cell receptor: implications for VH repertoire selection and cell signaling at the preB cell stage", Journal of Immunology (1999); 162: 41-50.
Gocník, et al., "Antibodies specific to the HA2 glycopolypeptide of influenza. A virus haemagglutinin with fusion-inhibition activity contribute to the protection of mice against lethal infection", Journal of General Virology (2007); 88(Part 3): 951-955.
Goudsmit, Japp, "Discovery of a unique set of human monoclonal antibodies active against H5N1." Presentation at 5th International Bird Flu Summit, Sep. 27, 2007, URL link http://investors.crucell.com/C/132631/present 2007 v2.html, 35 pages.
Goudsmit, Japp, "New Directions in Fighting Flu." Presentation at Symposium for 10th Anniversary of Inflexal V, Apr. 26, 2007, 38 pages.
Govorkova, et al., "Immunization with reverse-genetics-produced H5N1 influenza vaccine protects ferrets against homologous and heterologous challenge." Journal of Infectious Diseases (2006); 194.2: 159-167.
Graduate School of Infection Control Diseases, et al. "Analysis on epitopes of neutralizing antibodies against a highly pathogenic avian influenza H5N1 and preparation of scFv." BMB2007 (30th Meeting of the Molecular Biology Society of Japan/80th Meeting of the Japanese Biochemical Society Joint Meeting) Lecture Abstracts, 2007, p. 851, #4P-1098 (and English translation), 3 pages.
Greenspan and Di Cera. "Defining epitopes: It's not as easy as it seems." Nature Biotechnology (1999); 17(10): 936-937.
Güssow and Seemann. "[5] Humanization of monoclonal antibodies." Methods in Enzymology (1991); 203: 99-121.
Hagiwara, S. "Transgenic expression of VpreB-3 under the control of the immunoglobulin heavy chain enhancer and SV40 promoter", The Kobe Journal of Medical Sciences (1996); 42(1): 43-49.
Hanson, et al., "Passive immunoprophylaxis and therapy with humanized monoclonal antibody specific for influenza A H5 hemagglutinin in mice", Respiratory Research (2006); 7: 126, pp. 1-10.
Hashida et al., "More Useful Maleimide Compounds for the Conjugation of Fab' to Horseradish Peroxidase through Thiol Groups in the Hinge",J. Applied Biochem. (1984); 6(1-2): 56-63.

Hirabayashi et al. "Kinetic analysis of the interactions of recombinant human VpreBand Ig V domain." Journal of Immunology (1995); 155(3): 1218-1228.
Hollis et al. PIR database, 1996, accession No. A33911, accessed on Sep. 12, 2012, Score Alignment 3 pages.
Hollis, Gregory F., et al. "Immunoglobulin lambda light-chain-related genes 14.1 and 16.1 are expressed in pre-B cells and may encode the human immunoglobulin omega light-chain protein." Proceedings of the National Academy of Sciences (1989); 86.14: 5552-5556.
Holm et al. "Functional mapping and single chain construction of the anti-cytokeratin 8 monoclonal antibody TSI." Molecular Immunology (2007); 44.6: 1075-1084.
Holt, et al., "Domain antibodies: proteins for therapy", Trends in Biotechnology (2003); 21.11: 484-490.
Horváth, et al. "A Hemagglutinin-Based Multipeptide Construct Elicits Enhanced Protective Immune Response in Mice Against Influenza A Virus Infection", Immunology Letters (1998); 60.2: 127-136.
International Search Report and Written Opinion for International Application No. PCT/US2008/058283, dated Oct. 30, 2008, 11 pages.
International Preliminary Report on Patentability for International Application No. PCT/US2008/058283, dated Sep. 29, 2009, 7 pages.
International Search Report and Written Opinion for International Application No. PCT/US2009/038636, dated Feb. 8, 2010, 21 pages.
International Preliminary Report on Patentability for International Application No. PCT/US2009/038636, dated Sep. 28, 2010, 13 pages.
International Search Report and Written Opinion for International Application No. PCT/US2010/034604, dated Jan. 26, 2011, 21 pages.
International Preliminary Report on Patentability for International Application No. PCT/US2010/034604, dated Nov. 15, 2011, 13 pages.
International Search Report and Written Opinion for International Application No. PCT/US2012/044746, dated Dec. 4, 2012, 10 pages.
International Preliminary Report on Patentability for International Application No. PCT/US2012/044746, dated Jan. 7, 2014, 6 pages.
International Search Report and the Written Opinion for International Application No. PCT/US2012/048730, dated Nov. 6, 2012, 15 pages.
International Preliminary Report on Patentability for International Application No. PCT/US2012/048730, dated Jan. 28, 2014, 7 pages.
International Search Report and the Written Opinion for International Application No. PCT/US2012/071352, dated May 14, 2013, 15 pages.
International Preliminary Report on Patentability for International Application No. PCT/US2012/071352, dated Jun. 24, 2014, 9 pages.
International Search Report and the Written Opinion for International Application No. PCT/US2013/022308, dated Mar. 8, 2013, 9 pages.
International Preliminary Report on Patentability for International Application No. PCT/US2013/022308, dated Jul. 22, 2014, 5 pages.
Jang et al, "The structural basis for DNA binding by an anti-DNA autoantibody", Molecular immunology (1998); 35.18: 1207-1217.
Johnson et al., "Anti-Tumor Activity of CC49-Doxorubicin Immunoconjugates", Anticancer Res. 15:1387-93 (1995).
Kaneko et al., "New Hydrazone Derivatives of Adriamycin and Their Immunoconjugates—a Correlation between Acid Stability and Cytotoxicity", Bioconjugate Chem. 2:133-41 (1991).
Karasuyama et al. "Surrogate light chain in B cell development", Advances in Immunology (1996); 63: 1-41.
Karasuyama et al. "The proteins encoded by the VpreB and 5 pre-B cell-specific genes can associate with each other and with heavy chain", The Journal of Experimental Medicine (1990); 172.3: 969-972.

(56) References Cited

OTHER PUBLICATIONS

Kashap, et al. "Combinatorial, antibody libraries from survivors of the Turkish H5NI avian influenza outbreak reveal virus neutralization strategies", Proceedings of the National Academy of Sciences (2008); 105(16): 5986-5991.
Kobayashi et al, "Tryptophan H33 plays an important role in pyrimidine (6-4) pyrimidone photoproduct binding by a high-affinity antibody", Protein Engineering (1999); 12.10: 879-884.
Kong, et al., "Successful treatment of avian influenza with convalescent plasma", Hong Kong Med. Journal (2006); 12(6): 489.
Kudo et al. (PIR database, 1987 accession No. A26166, accessed on Jul. 19, 2010 Score Alignment , 4 pages.
Kumar et al., "Molecular Cloning and Expression of the Fabs of Human Autoantibodies in *Escherichia coli*. Determination of the heavy or light chain contribution to the anti-DNA/-Cardiolipin activity of the Fab", J. Biol. Chem. (2000); 275: 35129-35136.
Lamminmaki and Kankare. "Expanding the conformational diversity by random insertions to CDRH2 results in improved anti-estradiol antibodies", J. Mol. Biol., 291: 589-602, (1999).
Lanig et al. "Three dimensional modeling of a pre B-cell receptor", Molecular Immunology (2004); 40(17): 1263-1272.
Lau et al., "Conjugation of Doxorubicin to Monoclonal Anti-carcinoembryonic Antigen Antibody via Novel Thiol-directed Cross-linking Reagents", Bioorg-Med-Chem. 3(10):1299-1304 (1995).
Lau et al., "Novel Doxorubicin-Monoclonal Anti-carcinoembryonic Antigen Antibody Immunoconjugate Activity in vitro", Bioorg-Med-Chem. 3(10): 1305-12 (1995).
Law, et al., "Broadly neutralizing antibodies protect against hepatitis C virus quasispecies challenge", Nature Medicine (2008); 14(1): 25-27.
Lee, et al. "Generation of Bivalent and Bispecific Kringle Single Domains by Loop Grafting as Potent Agonists against Death Receptors 4 and 5." Journal of Molecular Biology (2011); 411(1): 201-219.
Lee, et al., High-affinity human antibodies from phage-displayed synthetic Fab libraries with a single framework scaffold, J. Mol. Biol., 340: 1073-1093, (2004).
Lerner, et al., "Manufacturing immunity to disease in a test tube: the magic bullet realized", Angewandte Chemie International Edition (2006); 45.48: 8106-8125.
Lerner, et. al., "Rare antibodies from combinatorial libraries suggests an S.O.S. component of the human immunological repertoire", Molecular BioSystems (2011); 7.4: 1004-1012.
Lippincott-Schwartz. "Antibodies as Cell Biological Tools." Current Protocols in Cell Biology (2002); 16.0.1-16.0.2.
Liu et al., "New Procedures for Preparation and Isolation of Conjugates of Proteins and a Synthetic Copolymer of D-Amino Acids and Immunochemical Characterization of Such Conjugatest", BIOCHEM., 18:690-697 (1979).
Lu, et al., "Passive immunotherapy for influenza A H5NI virus infection with equine hyperimmune globulin F(ab')2 in mice", Respiratory Research (2006); 7: 43, pp. 1-7.
Luke, et al., "Meta-analysis: Convalescent blood products for Spanish influenza pneumonia: A future H5N1 treatment", Annals of Internal Medicine (2006); 145.8: 599-609.
MacCallum, et al. "Antibody-antigen interactions: contact analysis and binding site topography." Journal of Molecular Biology (1996); 262.5: 732-745.
Mariuzza, et al. "The structural basis of antigen-antibody recognition." Annual Review of Biophysics and Biophysical Chemistry (1987); 16.1: 139-159.
Mårtensson, Inga-Lill, et al. "The pre-B cell receptor checkpoint." FEBS Letters (2010); 584.12: 2572-2579.
Mateu, et al. "Non-additive effects of multiple amino acid substitutions on antigen-antibody recognition." European Journal of Immunology (1992); 22: 1385-1389.
McKeller, Morgan R., and Martinez-Valdez, Hector. "The κ-like pre-B receptor: Surplus biology or a missing link?." Seminars in Immunology (2006); 18(1): 40-43.

Melchers et al. "Fit for life in the immune system? Surrogate L chain tests H chains that test L chains", Proc. Natl. Acad. Sci. USA (1999); 96: 2571-2573.
Melchers et al. "The surrogate light chain in B-cell development", Immunology Today (1993); 14.2: 60-68.
Minegishi et al., "Novel mechanisms control the folding and assembly of 5/14.1 and VpreB to produce an intact surrogate light chain", Proceedings of the National Academy of Sciences (1999); 96.6: 3041-3046.
Morris, Glenn E. "Epitope Mapping of Protein Antigens by Competition ELISA" In: "The Protein Protocols Handbook", Jan. 1, 1996, (Jan. 1, 1996), Humana Press, Totowa, NJ, XP055007939, ISBN: 978-1-60-327259-9, pp. 595-600, DOI: 10.1007/978-1-60327-259-9_96.
Milutinovic, Snezana, et al. "Development of a novel SurrobodyTM that simultaneously activates both death receptors DR4 and DR5 and induces cancer cell death with high potency." Cancer Research (2013); 73.8 Supplement: 4318-4318.
Milutinovic, Snezana, et al. "Dual Agonist Surrobody Simultaneously Activates Death Receptors DR4 and DR5 to Induce Cancer Cell Death." Molecular Cancer Therapeutics (2016); 15.1: 114-124, 11 pages.
Neville, Jr. et al., "Enhancement of Immunotoxin Efficacy by Acid-cleavable Cross-linking Agents Utilizing Diphtheria Toxin and Toxin Mutants*", Biol. Chem. 264:14653-14661 (1989).
Ohnishi and Melchers. "The nonimmunoglobulin portion of λ5 mediates cell-autonomous pre-B cell receptor signaling." Nature Immunology (2003); 4.9: 849-856.
Okuno, et al., "A common neutralizing epitope conserved between the hemagglutinins of influenza A virus H1 and H2 strains." Journal of Virology (1993); 67.5: 2552-2558.
Oner, et al. "Avian influenza A (H5N1) infection in eastern Turkey in 2006." New England Journal of Medicine (2006); 355.21: 2179-2185.
Palese, P. and Shaw, M.L. "Orthomyxoviridae: The viruses and their replication", Fields Virology (2007); 2: 1647-1689.
Pan, et al., "Methionine oxidation in human IgG2 Fc decreases binding affinities to protein A and FcRn", Protein Science (2009); 18.2: 424-433.
Paul, Fundamental Immunology, 3rd Edition, 1993, pp. 292-295.
Portolano, Stefano, et al. "Lack of promiscuity in autoantigen-specific H and L chain combinations as revealed by human H and L chain"roulette"." The Journal of Immunology (1993); 150.3: 880-887.
Rangel et al. "Assembly of the kappa preB receptor requires a V kappa-like protein encoded by a germline transcript", Journal of Biological Chemistry (2005); 280.18: 17807-17814.
Robinson et al., "Targeting ErbB2 and ErbB3 with a bispecific single-chain Fv enhances targeting 39 selectivity and induces a therapeutic effect In vitro", British Journal of Cancer (2008); 99.9: 1415-1425.
Rudikoff et al. "Single amino acid substitution altering antigen-binding specificity", Proceedings of the National Academy of Sciences (1982); 79.6: 1979-1983.
Simmons, et al., "Prophylactic and therapeutic efficacy of human monoclonal antibodies against H5NI influenza", PLOS Medicine (2007); 4(5): 928-936.
Smirnov, et al., "Prevention and treatment of bronchopneumonia in mice caused by mouse-adapted variant of avian H5N2 influenza A virus using monoclonal antibody against conserved epitope in the HA stem region", Archives of Virology (2000); 145.8: 1733-1741.
Smirnov, et al., "An epitope shared by the hemagglutinins of H1, H2, H5 and H6 subtypes of influenza A virus", Acta Virologica (1999); 43.4: 237-244.
Smith-Gill et al, "Contributions of immunoglobulin heavy and light chains to antibody specificity for lysozyme and two haptens", The Journal of Immunology (1987); 139.12: 4135-4144.
Song et al. "Light chain of natural antibody plays a dominant role in protein antigen binding", Biochemical and Biophysical Research Communications (2000); 268.2: 390-394.
Thompson et al. "A pro-B-cell stage characterized by germline Ig transcription without surrogate light chain expression." Immunogenetics (1998); 48(5): 305-311.

(56) References Cited

OTHER PUBLICATIONS

Thorpe et al., "New Coupling Agents for the Synthesis of Immunotoxins Containing a Hindered Disulfide Bond with Improved Stability in Vivo", Cancer Res. 47:5924-5931 (1987).

Throsby, et al., "Heterosubtypic neutralizing monoclonal antibodies cross-protective against H5NI recovered from human IgM memory B cells", PLoS ONE (2008); 3.12:: e3942, pp. 1-15.

Vajdos et al. "Comprehensive functional maps of the antigen-binding site of an Anti-ErbB2 antibody obtained with shotam scanning mutagenesis", Journal of Molecular Biology (2002); 320. 2: 415-428.

Vermot-Desroches, C. et al. "Characterization of monoclonal antibodies directed against trail or trail receptors." Cellular Immunology (2005); 236.1: 86-91.

Ward et al, "Binding activities of a repertoire of single immunoglobulin variable domains secreted from *Escherichia coli*", Nature (1989); 341.6242: 544-546.

Wawrzynczak et al., "In Immunoconjugates: Antibody Conjugates in Radioimagery and Therapy of Cancer," (C.W. Vogel ed., Oxford U. Press (1987).

Wiley and Skehel. "The structure and function of the hemagglutinin membrane glycoprotein of influenza virus." Ann. Rev. Biochem. (1987); 56:365-394.

Wu et al. "Humanization of a Murine monoclonal antibody by simultaneous optimization of framework and CDR residues", Journal of Molecular Biology (1999); 294.1: 151-162.

Xu et al. "Combinatorial surrobody libraries", Proceedings of the National Academy of Sciences (2008); 105.31: 10756-10761.

Xu et al. "Surrobodies with functional tails", Journal of Molecular Biology (2010); 397.1: 352-360.

Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., 101:395-399 (1979).

Yuste, L., "Activation of ErbB2 by Overexpression or by Transmembrane Neuregulin Results in Differential Signaling and Sensitivity to Herceptin", Cancer Research (2005); 65.15: 6801-6810.

Zhou, et al., "Treatment with convalescent plasma for influenza A (H5NI) infection", New England Journal of Medicine (2007); 357.14: 1450-1451.

Creative Biolabs, Data sheet for "Recombinant Anti-DR4 × Anti-DR5 Bi-specific T-cell engagers (BiTE, 3631-G09(SL231))", 2 pages [Retrieved on line] URL:<http://www.creativebiolabs.net/pdf/BITE-MZ047.pdf>, [Retrieved May 11, 2017] 2017.

Ewert, et al., "Stability improvement of antibodies for extracellular and intracellular applications: CDR grafting to stable frameworks and structure-based framework engineering." Methods (2004); 34(2): 184-199.

Figure 3

15 mg/kg antibody treatment after 33LD50 X-31 infection

NEUTRALIZING MOLECULES TO INFLUENZA VIRUSES

REFERENCE TO RELATED APPLICATIONS

This application is a continuation of U.S. patent application Ser. No. 13/261,004, filed Feb. 2, 2012 (now abandoned), which is a National Stage Entry of PCT Application No. PCT/US2010/034604, filed May 12, 2010, which claims priority to U.S. Provisional Application No. 61/228,114, filed Jul. 23, 2009, and to U.S. Provisional Application No. 61/177,987, filed May 13, 2009, each of which is incorporated by reference herein in their entireties.

FIELD OF THE INVENTION

The present invention concerns methods and means for identifying, producing, and engineering neutralizing molecules against influenza A viruses, and to the neutralizing molecules produced. The invention further concerns various uses of the molecules produced, including the design and production of vaccines utilizing the binding sites of the neutralizing molecules of the present invention on the target influenza A virus.

BACKGROUND OF THE INVENTION

The flu is a contagious respiratory illness caused by influenza viruses. It causes mild to severe illness, and at times can lead to death. Annually, in the United States, influenza is contracted by 5-20% of the population, hospitalizing about 200,000, and causing the deaths of about 36,000.

Influenza viruses spread in respiratory droplets caused by coughing and sneezing, which are usually transmitted from person to person. Immunity to influenza surface antigens, particularly hemagglutinin, reduces the likelihood of infection and severity of disease if infection occurs. Although influenza vaccines are available, because a vaccine against one influenza virus type or subtype confers limited or no protection against another type or subtype of influenza, it is necessary to incorporate one or more new strains in each year's influenza vaccine.

Influenza viruses are segmented negative-strand RNA viruses and belong to the Orthomyxoviridae family. Influenza A virus consists of 9 structural proteins and codes additionally for one nonstructural NS1 protein with regulatory functions. The non-structural NS1 protein is synthesized in large quantities during the reproduction cycle and is localized in the cytosol and nucleus of the infected cells. The segmented nature of the viral genome allows the mechanism of genetic reassortment (exchange of genome segments) to take place during mixed infection of a cell with different viral strains. The influenza A virus may be further classified into various subtypes depending on the different hemagglutinin (HA) and neuraminidase (NA) viral proteins displayed on their surface. Influenza A virus subtypes are identified by two viral surface glycoproteins, hemagglutinin (HA or H) and neuraminidase (NA or N). Each influenza virus subtype is identified by its combination of H and N proteins. There are 16 known HA subtypes and 9 known NA subtypes. Influenza type A viruses can infect people, birds, pigs, horses, and other animals, but wild birds are the natural hosts for these viruses. Only some influenza A subtypes (i.e., H1N1 H1N2, and H3N2) are currently in circulation among people, but all combinations of the 16 H and 9 NA subtypes have been identified in avian species, especially in wild waterfowl and shorebirds. In addition, there is increasing evidence that H5 and H7 influenza viruses can also cause human illness.

The HA of influenza A virus comprises two structurally distinct regions, namely, a globular head region and a stem region. The globular head region contains a receptor binding site which is responsible for virus attachment to a target cell and participates in the hemagglutination activity of HA. The stem region contains a fusion peptide which is necessary for membrane fusion between the viral envelope and an endosomal membrane of the cell and thus relates to fusion activity (Wiley et al., *Ann. Rev. Biochem.*, 56:365-394 (1987)).

A pandemic is a global disease outbreak. An influenza pandemic occurs when a new influenza A virus: (1) emerges for which there is little or no immunity in the human population, (2) begins to cause serious illness, and then (3) spreads easily person-to-person worldwide. During the 20$^{th}$ century there have been three such influenza pandemics. First, in 1918, the "Spanish Flu" influenza pandemic caused at least 500,000 deaths in the United States and up to 40 million deaths worldwide. This pandemic was caused by influenza A H1N1 subtype. Second, in 1957, the "Asian Flu" influenza pandemic, caused by the influenza A H2N2 subtype, resulted in at least 70,000 deaths in the United States and 1-2 million deaths worldwide. Most recently in 1968 the "Hong Kong Flu" influenza pandemic, caused by the influenza A H3N2 subtype, resulted in about 34,000 U.S. deaths and 700,000 deaths worldwide.

In 1997, the first influenza A H5N1 cases were reported in Hong Kong. This was the first time that this type of avian virus directly infected humans, but a pandemic did not result because human to human transmission was not observed.

Lu et al., *Resp. Res.* 7:43 (2006) (doi: 10.1186/1465-992-7-43) report the preparation of anti-H5N1 IgGs from horses vaccinated with inactivated H5N1 virus, and of H5N1-specifc F(ab')$_2$ fragments, which were described to protect BALB/c mice infected with H5N1 virus.

Hanson et al., *Resp. Res.* 7:126 (doi: 10.1186/1465-9921-7-126) describe the use of a chimeric monoclonal antibody specific for influenza A H5 virus hemagglutinin for passive immunization of mice.

Neutralizing antibodies to influenza viruses are disclosed in U.S. Application Publication No. 20080014205, published on Jan. 17, 2008.

In view of the severity of the respiratory illness caused by certain influenza A viruses, and the threat of a potential pandemic, there is a great need for effective preventative and treatment methods. The present invention addresses this need by providing influenza A neutralizing molecules against various H subtypes of the virus, including, without limitation, the H1, and H3 subtypes, and the H5 subtype of the influenza A virus. The invention further provides molecules capable of neutralizing more than one, and preferably all, isolates (strains) of a given subtype of the influenza A virus, including, without limitation, isolates obtained from various human and non-human species and isolates from victims and/or survivors of various influenza epidemics and/or pandemics.

Such crossreactive neutralizing molecules can be used for the prevention and/or treatment influenza virus infection, including passive immunization of infected or at risk populations in cases of epidemics or pandemics. Additionally, crossreactive antibodies can be used as a design guide for future vaccine discovery and an assessment tool for current vaccine clinical development.

SUMMARY OF THE INVENTION

In one aspect, the present invention provides binding molecules comprising hypervariable regions from heavy chain and light chain polypeptides. In one embodiment, the binding molecule comprises one, two, or three hypervariable region sequences from a heavy chain selected from the group consisting of SEQ ID NO:7, SEQ ID NO:8, and SEQ ID NO:9, or a functionally active fragment thereof. In another embodiment, the binding molecule comprises all hypervariable region sequences SEQ ID NO:7, SEQ ID NO:8, and SEQ ID NO:9. In one other embodiment, the binding molecule is a binding molecule which is capable of binding a target when associated with a light chain. In one embodiment, the light chain or binding molecule comprises one, two or three hypervariable sequences of the polypeptide sequence of SEQ ID NO:13, SEQ ID NO:14, and SEQ ID NO:15. In another embodiment, the light chain or binding molecule comprises one, two or three hypervariable sequences of the polypeptide sequence of SEQ ID NO:16, SEQ ID NO:17, and SEQ ID NO:18. In one other embodiment, the light chain or binding molecule comprises one, two or three hypervariable sequences of the polypeptide sequence of SEQ ID NO:19, SEQ ID NO:20, and SEQ ID NO:21. In another embodiment, the light chain or binding molecule comprises all hypervariable region sequences SEQ ID NO:13, SEQ ID NO:14, and SEQ ID NO:15. In another embodiment, the light chain or binding molecule comprises all hypervariable region sequences SEQ ID NO:16, SEQ ID NO:17, and SEQ ID NO:18. In one other embodiment, the light chain or binding molecule comprises all hypervariable region sequences SEQ ID NO:19, SEQ ID NO:20, and SEQ ID NO:21.

In another embodiment, the binding molecule that comprises one, two, or three hypervariable region sequences from a heavy chain selected from the group consisting of SEQ ID NO:10, SEQ ID NO:11, and SEQ ID NO:12, or a functionally active fragment thereof. In one other embodiment, the binding molecule comprises all hypervariable region sequences SEQ ID NO:10, SEQ ID NO:11, and SEQ ID NO:12. In one other embodiment, the binding molecule is a binding molecule which is capable of binding a target when associated with a light chain. In one embodiment, the light chain or binding molecule comprises one, two or three hypervariable sequences of the polypeptide sequence of SEQ ID NO:22, SEQ ID NO:23, and SEQ ID NO:24. In one other embodiment, the light chain or binding molecule comprises all hypervariable region sequences SEQ ID NO:22, SEQ ID NO:23, and SEQ ID NO:24.

In one embodiment, the binding molecule is an antibody. In another embodiment, the binding molecule is a surrobody.

In another aspect, the present invention provides binding molecules comprising a VpreB sequence and/or a λ5 sequence. In one embodiment, the binding molecule comprises a polypeptide comprising a VpreB sequence and/or a λ5 sequence. In another embodiment, the binding molecule further comprises a polypeptide comprising a VpreB sequence fused to a λ5 sequence. In one other embodiment, the binding molecule further comprises a κ-like surrogate light chain (SLC) construct comprising a Vκ-like and/or a Jκ sequence.

In all embodiments, the binding molecules (i) neutralize more than one subtype and/or more than one isolate of an influenza A virus, (ii) bind to a hemagglutinin (HA) antigen of the virus, and (iii) inhibit hemagglutination. In another embodiment, the binding molecule which neutralizes at least one of the H1 and H3 influenza A virus subtypes. In one embodiment, the binding molecule neutralizes the H1 and H3 influenza A virus subtypes. In another embodiment, the binding molecule prevents the globular head region of the influenza A virus from binding the surface of a cell. In one other embodiment, the binding molecule prevents the influenza A virus from attaching to a cell to be infected. In another embodiment, the binding molecule binds to an H1 HA antigen. In one embodiment, the binding molecule binds to at least one additional HA antigen. In another embodiment, the additional HA antigen is H3. In another embodiment, the binding molecule binds to an H2 HA antigen.

In one embodiment, the present invention provides an antibody comprising a heavy chain, the heavy chain comprising the amino acid sequence shown as SEQ ID NO:1. In another embodiment, the antibody further comprises a light chain comprising the amino acid sequence selected from the group consisting of SEQ ID NO:3, SEQ ID NO:4, and SEQ ID NO:5. In one other embodiment, the antibody is an antibody which (i) neutralizes more than one subtype and/or more than one isolate of an influenza A virus, (ii) binds to a hemagglutinin (HA) antigen of the virus, and (iii) inhibits hemagglutination. In another embodiment, the antibody is an antibody which neutralizes at least one of the H1 and H3 influenza A virus subtypes. In one embodiment, the antibody is an antibody which neutralizes the H1 and H13 influenza A virus subtypes. In another embodiment, the antibody is an antibody which prevents the globular head region of the influenza A virus from binding the surface of a cell. In one other embodiment, the antibody is an antibody which prevents the influenza A virus from attaching to a cell to be infected. In another embodiment, the antibody is an antibody which binds to an H1 HA antigen. In one embodiment, the antibody is an antibody which binds to at least one additional HA antigen. In another embodiment, the additional HA antigen is H3.

In another embodiment, the antibody comprises a heavy chain, the heavy chain comprising the amino acid sequence shown as SEQ ID NO: 2. In one other embodiment, the antibody further comprises a light chain comprising the amino acid sequence shown as SEQ ID NO:6. In one other embodiment, the antibody is an antibody which (i) neutralizes at least one subtype and/or at least one isolate of an influenza A virus, and (ii) binds to a hemagglutinin (HA) antigen of the virus. In one embodiment, the antibody is an antibody which binds to an epitope of an H5 subtype of the HA antigen. In another embodiment, the antibody is an antibody which neutralizes the H1 HA antigen; which neutralizes the H5 HA antigen; or which neutralizes the H1 and H5 influenza A virus subtypes.

In another embodiment, the antibodies or binding molecules bind to and/or are reactive to and/or neutralize more than one subtype and/or more than one isolate of an influenza A virus. In one embodiment, the virus is a virus having the ability to infect humans. In another embodiment, the isolate is an isolate that has been obtained from a human subject. In one other embodiment, the isolate is an isolate that has been obtained from a non-human animal. In another embodiment, the non-human animal is a bird. In one embodiment, the bird is a wild-fowl or a chicken. In one other embodiment, the non-human animal is a pig.

In another embodiment the antibody or binding molecule is an antibody or binding molecule which binds to an epitope of an H1 subtype of the HA antigen. In one other embodiment, the antibody or binding molecule is an antibody or binding molecule which binds to an epitope of an H3 subtype of the HA antigen. In another embodiment, the antibody or binding molecule is an antibody or binding molecule which binds to an epitope of an H1 subtype of the HA antigen and to an epitope of an H3 subtype of the HA antigen. In one embodiment, the antibody or binding molecule is an antibody or binding molecule which binds to an epitope of an H9 subtype of the HA antigen. In another embodiment, the antibody or binding molecule is an antibody or binding molecule which binds to an epitope of an H5 subtype of the HA antigen. In another embodiment, the antibody or binding molecule is an antibody or binding molecule which binds to an epitope of an H2 subtype of the HA antigen.

In all embodiments, the antibody or binding molecule binds to an epitope which is displayed on the surface of an influenza A virus.

In all embodiments, the H1 subtype is, or the HA is from, a New Caledonia/20/99 isolate of the H1 virus; the H1 subtype is, or the HA is from, a Solomon Islands/3/06 isolate of the H1 virus; or a Memphis/3/2008 isolate of the H1 virus.

In all embodiments, the H3 subtype is, or the HA is from, a Wisconsin/67/05 isolate of the H3 virus; or the H3 subtype is, or the HA is from, a Hong Kong/68 isolate of the H3 virus.

In all embodiments, the H9 subtype is, or the HA is from, a Hong Kong/1073/99 isolate of the H9 virus.

In all embodiments, the H5 subtype is, or the HA is from, a Vietnam/1203/04 isolate of the H5 virus.

In all embodiments, the H2 subtype is, or the HA is from, the Adachi/1/1957 isolate of the H12 virus.

In all embodiments, the antibody or binding molecule is an antibody or binding molecule which is cross-reactive with an H1 HA antigen and an H3 antigen.

In one other embodiment, the present invention provides an antibody or binding molecule which binds essentially the same epitope as the epitope for an antibody comprising a heavy chain polypeptide comprising an amino acid sequence shown as SEQ ID NO:1; or a consensus or variant sequence based upon said amino acid sequence. In another embodiment, the antibody or binding molecule binds essentially the same epitope as the epitope for an antibody comprising a light chain polypeptide comprising an amino acid sequence selected from the group consisting of SEQ ID NO:3, SEQ ID NO:4, and SEQ ID NO:5; or a consensus or variant sequence based upon said amino acid sequence. In one other embodiment, the antibody or binding molecule is an antibody or binding molecule which (i) neutralizes more than one subtype and/or more than one isolate of an influenza A virus, (ii) binds to a hemagglutinin (HA) antigen of the virus; and (iii) inhibits hemagglutination.

In one embodiment, the present invention provides an antibody or binding molecule which binds essentially the same epitope as the epitope for an antibody comprising a heavy chain polypeptide comprising an amino acid sequence shown as SEQ ID NO:2; or a consensus or variant sequence based upon said amino acid sequence. In another embodiment, the antibody or binding molecule binds essentially the same epitope as the epitope for an antibody comprising a light chain polypeptide comprising an amino acid sequence shown as SEQ ID NO:6; or a consensus or variant sequence based upon said amino acid sequence. In one other embodiment, the antibody or binding molecule is an antibody or binding molecule which (i) neutralizes more than one subtype and/or more than one isolate of an influenza A virus, and (ii) binds to a hemagglutinin (HA) antigen of the virus.

In another embodiment, the present invention provides a composition comprising a binding molecule or an antibody described herein.

In another aspect, the present invention provides methods for the treatment and/or prevention of an influenza A virus infection in a subject in need. In one embodiment, the methods comprises administering to said subject an effective amount of a composition described herein. In another embodiment, the method comprises comprising administering to said subject an effective amount of a neutralizing antibody or binding molecule described herein. In one other embodiment, the subject is a human patient.

In another aspect, the present invention provides a vaccine effective against influenza A virus infection. In one embodiment, the vaccine comprises a peptide or polypeptide functionally mimicking a neutralization epitope bound by an antibody or binding molecule described herein. In another embodiment, the vaccine is a synthetic vaccine. In one other embodiment, the vaccine comprises an attenuated influenza A virus, or a part thereof. In another embodiment, the vaccine comprises a killed influenza A virus, or part thereof. In one other embodiment, the antibody or binding molecule is selected from the group consisting of (a) an antibody or binding molecule which binds essentially the same epitope as the epitope for an antibody comprising a heavy chain polypeptide comprising an amino acid sequence shown as SEQ ID NO:1; or a consensus or variant sequence based upon said amino acid sequences; (b) an antibody comprising a heavy chain polypeptide comprising a heavy chain polypeptide comprising an amino acid sequence shown as SEQ ID NO:1; or a consensus or variant sequence based upon said amino acid sequence; (c) an antibody or binding molecule which binds essentially the same epitope as the epitope for an antibody comprising a heavy chain polypeptide comprising an amino acid sequence shown as SEQ ID NO:2; or a consensus or variant sequence based upon said amino acid sequences, or a fragment thereof; and (d) an antibody comprising a heavy chain polypeptide comprising an amino acid sequence shown as SEQ ID NO:2; or a consensus or variant sequence based upon said amino acid sequences, or a fragment thereof.

In all embodiments, the antibody binds an HA antigen. The HA antigen may be selected from the group consisting of an H3 subtype; an H1 subtype; an H2 subtype; an H1 subtype and an H3 subtype; an H5 subtype; an H9 subtype, and any combination thereof. In one embodiment, the antigen is displayed on the surface of an influenza A virus. In another embodiment, the peptide or polypeptide functionally mimicking a neutralization epitope bound by an antibody or binding molecule described herein, comprises antigenic determinants that raise neutralizing antibodies. In another embodiment, the vaccine is suitable for oral administration; transdermal administration; or parenteral administration. In another embodiment, the vaccine is suitable for transmucosal delivery. In one other embodiment, the transmucosal delivery is intranasal administration. In another embodiment, the vaccine is for childhood immunization.

In one aspect, the present invention provides influenza neutralizing antibodies or binding molecules with a length-modified heavy chain loop. The length modified chain may be an extended heavy chain loop or a shortened heavy chain loop. In one embodiment, the antibody or binding molecule is a neutralizing antibody or binding molecule binding to a hemagglutinin of an influenza A virus having the ability to infect humans neutralizing at least one isolate of an influenza A virus, antibody having an extended heavy chain loop. In one other embodiment, the length-modified heavy chain loop is a CDR3 loop or a CDR1 loop. In another embodiment, the CDR3 loop comprises an amino acid sequence SEQ ID NO:9. In yet another antibody, the CDR1 loop comprises an amino acid sequence SEQ ID NO:7.

In another aspect, the present invention provides engineered antibodies or binding molecules with reduced oxidative potential. In one embodiment, the engineered antibody or binding molecule with reduced oxidative potential is an antibody binding to a hemagglutinin of an influenza A virus having the ability to infect humans neutralizing at least one isolate of an influenza A virus having one or more methionine substitutions in a heavy chain variable domain. In another embodiment, the heavy chain variable domain is a CDR3 region. In one other embodiment, the methionine substitution is at position 96 and/or 98 according to Kabat numbering system. In yet another embodiment, the methionine is substituted with a leucine. In one embodiment, the heavy chain variable domain includes an amino acid sequence SEQ ID NO:29.

BRIEF DESCRIPTION OF THE DRAWINGS

FIG. 3 illustrates a representative mutagenesis method for generating a diverse multifunctional antibody collection by the "destinational mutagenesis" method.

FIG. 7A-B show a prophylactic effect by the C05 antibody against high titer lethal H3N2 viral challenge. FIG. 7C-D show a therapeutic effect by the C05 antibody against lethal H3N2 viral challenge. FIG. 7E shows a prophylactic effect by the C05 antibody against high titer seasonal H1N1 viral challenge.

DETAILED DESCRIPTION

A. Definitions

Figure 1:
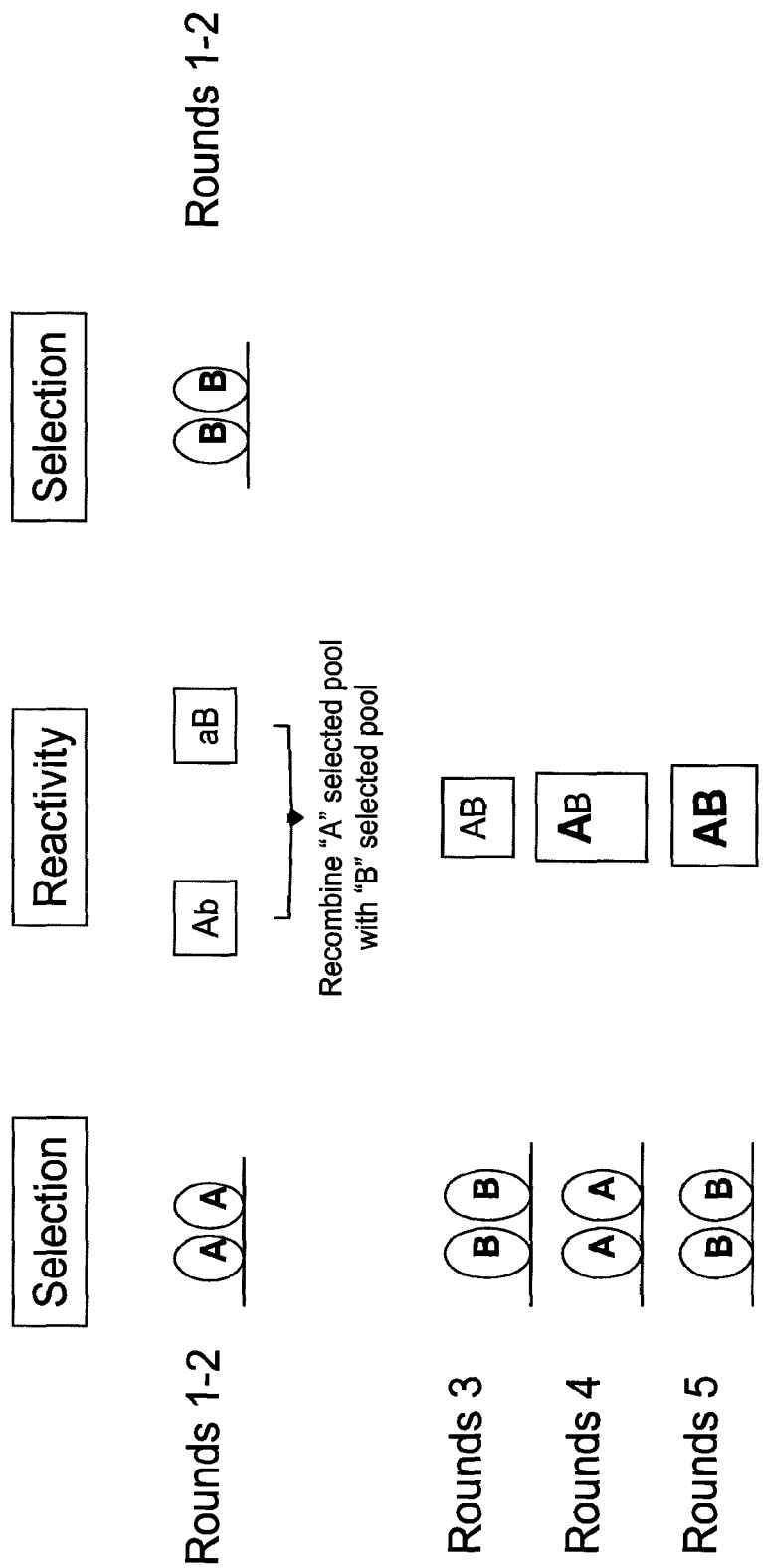
FIG. 1 illustrates a strategy for increasing the reactive strengths towards two different targets (targets A and B), by recombining parallel discovery pools to generate/increase cross-reactivity. Each round of selection of the recombined antibody library increases the reactive strength of the resulting pool towards both targets.
Figure 2:
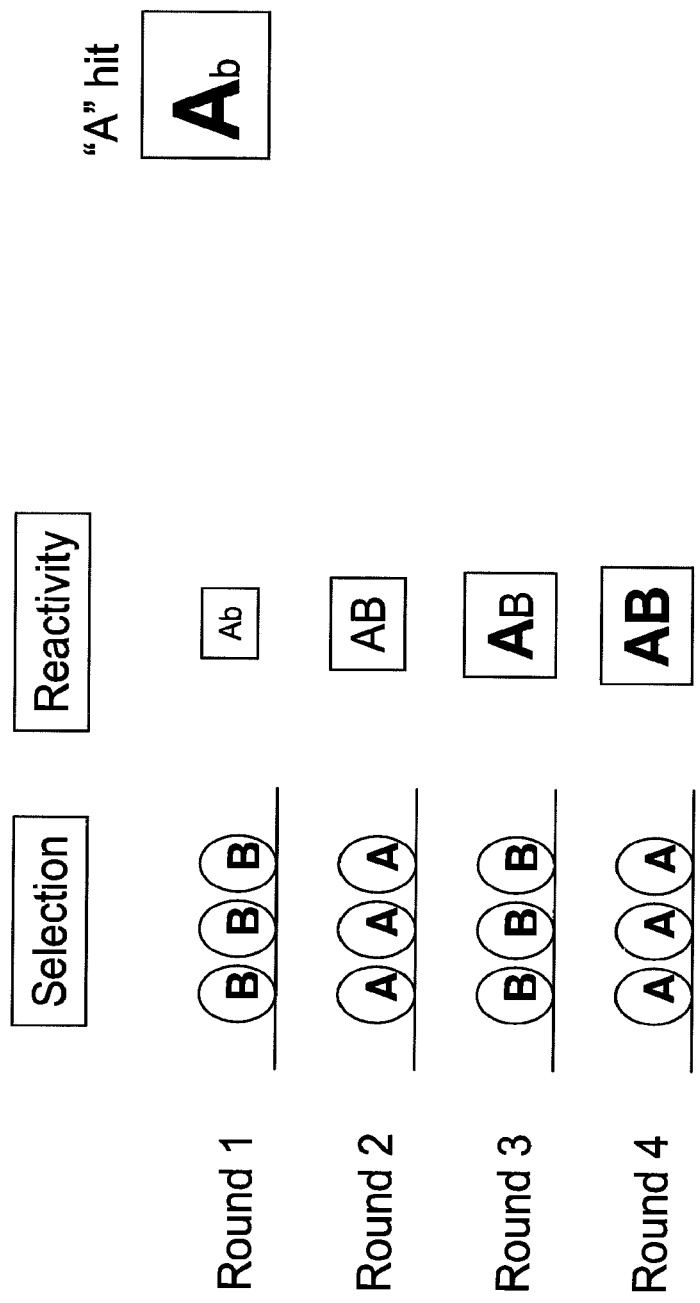
FIG. 2 illustrates a strategy for increasing cross-reactivity to a target B while maintaining reactivity to a target A. First, a clone reactive with target A is selected, then a mutagenic library of the clones reactive with target A is prepared, and selection is performed as shown, yielding one or more antibody clones that show strong reactivity with both target A and target B.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "influenza A subtype" or "influenza A virus subtype" are used interchangeably, and refer to influenza A virus variants that are characterized by a hemagglutinin (H) viral surface protein, and thus are labeled by an H number, such as, for example, H1, H3, H5 and H9. In addition, the subtypes may be further characterized by a neuraminidase (N) viral surface protein, indicated by an N number, such as; for example, N1 and N2. As such, a subtype may be referred to by both H and N numbers, such as, for example, H1N1, H2N2, H3N2, H5N1, H5N2, and H9N2. The terms specifically include all strains (including extinct strains) within each subtype, which usually result from mutations and show different pathogenic profiles. Such strains will also be referred to as various "isolates" of a viral subtype, including all past, present and future isolates. Accordingly, in this context, the terms "strain" and "isolate" are used interchangeably. Subtypes contain antigens based upon an influenza A virus. The antigens may be based upon a hemagglutinin viral surface protein and can be designated as "HA antigen". In some instances, such antigens are based on the protein of a particular subtype, such as, for example, an H1 subtype and an H3 subtype, which may be designated an H1 antigen and an H3 antigen, respectively.

The term "influenza" is used to refer to a contagious disease caused by an influenza virus.

In the context of the present invention, the term "binding molecule" is used in the broadest sense and includes any molecule comprising a polypeptide sequence that specifically binds to a target. The definition includes, without limitation, antibodies and antibody fragments, antibody-like molecules and fragments thereof, whether in monomeric or in a multimeric, such as homo- or heterodimeric, form. Multimeric binding molecules can retain their conformation through covalent and/or non-covalent interactions, and may be conjugated to each other and/or molecules or moieties, as long as they retain the requisite property of binding a target (e.g. an antigen in the case of antibodies).

A binding molecule that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "antibody" (Ab) is used in the broadest sense and includes polypeptides which exhibit binding specificity to a specific antigen as well as immunoglobulins and other antibody-like molecules which lack antigen specificity. Polypeptides of the latter kind are, for example, produced at low levels by the lymph system and, at increased levels, by myelomas. In the present application, the term "antibody" specifically covers, without limitation, monoclonal antibodies, polyclonal antibodies, and antibody fragments.

The terms "reduced oxidative potential" or "decreased oxidative heterogeneity potential" refer to an antibody containing a polypeptide with at least one amino acid substitution from an oxidizable amino acid to a non-oxidizable amino acid. The amino acid sequence may be a substitution for methionine. Antibody polypeptides may be selectively engineered to replace methionine amino acid residues with non-oxidizable amino acid residues thereby providing antibodies with reduced oxidative potential. For example, a methionine may be substituted with a leucine, a serine, or an alanine.

"Native antibodies" are usually heterotetrameric glycoproteins of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J. Mol. Biol.* 186:651 (1985); Novotny and Haber, *Proc. Natl. Acad. Sci. U.S.A.* 82:4592 (1985).

The term "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., *J Mol Biol.* 1996. "Framework" or "FR" residues are those variable domain residues other than the hypervariable region residues as herein defined.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains.

The term "antibody fragment" is a portion of a full length antibody, generally the antigen binding or variable domain thereof. Examples of antibody fragments include, but are not limited to, Fab, Fab', F(ab')$_2$, and Fv fragments, linear antibodies, single-chain antibody molecules, diabodies, and multispecific antibodies formed from antibody fragments. Further examples of antibody fragments include, but are not limited to, scFv, (scFv)$_2$, dAbs (single-domain antibodies), and complementarity determining region (CDR) fragments, and minibodies, which are minimized variable domains whose two loops are amenable to combinatorial mutagenesis.

The term "monoclonal antibody" is used to refer to an antibody molecule synthesized by a single clone of B cells. The modifier "monoclonal" indicates the character of the antibody as being obtained from a substantially homogeneous population of antibodies, and is not to be construed as requiring production of the antibody by any particular method. Thus, monoclonal antibodies may be made by the hybridoma method first described by Kohler and Milstein, *Nature* 256:495 (1975); *Eur. J. Immunol.* 6:511 (1976), by recombinant DNA techniques, or may also be isolated from phage antibody libraries.

The term "polyclonal antibody" is used to refer to a population of antibody molecules synthesized by a population of B cells.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Plückthun in *The Pharmacology of Monoclonal Antibodies,* vol. 113, Rosenburg and Moore eds. Springer-Verlag, New York, pp. 269-315 (1994). Single-chain antibodies are disclosed, for example in WO 88/06630 and WO 92/01047.

The term "diabody" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The term "minibody" is used to refer to an scFv-CH3 fusion protein that self-assembles into a bivalent dimer of 80 kDa (scFv-CH3)$_2$.

The term "aptamer" is used herein to refer to synthetic nucleic acid ligands that bind to protein targets with high specificity and affinity. Aptamers are known as potent inhibitors of protein function.

A dAb fragment (Ward et al., *Nature* 341:544 546 (1989)) consists of a $V_H$ domain or a VL domain.

As used herein the term "antibody binding regions" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "bispecific antibody" refers to an antibody that shows specificities to two different types of antigens. The term as used herein specifically includes, without limitation, antibodies which show binding specificity for a target antigen and to another target that facilitates delivery to a particular tissue. Similarly, multi-specific antibodies have two or more binding specificities.

The expression "linear antibody" is used to refer to comprising a pair of tandem Fd segments ($V_H$-$C_H$1-$V_H$-$C_H$1) which form a pair of antigen binding regions. Linear antibodies can be bispecific or monospecific and are described, for example, by Zapata et al., *Protein Eng.* 8(10):1057-1062 (1995).

For the purposes of the present invention, the term "antibody-like molecule" includes any molecule, other than an antibody fragment as hereinabove defined, that is capable of binding to and neutralizing a viral antigen. The term specifically includes, without limitation, pre-B cell receptor (pre-BCR) like structures, referred to as "surrobodies," including surrogate light chain (SLC) elements, as described, for example, in PCT Publication No. WO 2008/118970, published Oct. 2, 2008, and in Xu et al., *Proc. Natl. Acad. Sci. USA,* 105(31):10756-61 (2008). The SLC is a nondiversified heterodimer composed of the noncovalently associated Vpre-B and λ5 proteins. The VpreB chain is homologous to a Vλ Ig domain, and the λ5 chain is homologous to the Cλ domain of canonical antibodies, respectively. The heterodimeric SLC is covalently associated with the heavy chain in the pre-BCR complex by disulfide bonds between the Cλ domain and the first constant domain of the pre-BCR HC. A unique feature of the SLC is that the VpreB1 and the λ5 domains each have noncanonical peptide extensions. VpreB1 has an additional 21 residues on its C terminus, and λ5 has a 50-aa-long tail on its N terminus (see, e.g. Vettermann et al., *Semin. Immunol.* 18:44-55 (2006)). The surrobody structures specifically include, without limitation, the native trimeric pre-BCR-like functional unit of the pre-BCR, fusion of VpreB1 to λ5, and trimers that eliminated either the λ5 N-terminal 50 aa or the VpreB1 C-terminal 21 aa or both peptide extensions. In addition, chimeric constructs using the constant components of classical antibody light chains are specifically included within the definition of surrobodies.

Other representatives of "antibody-like molecules," as defined herein, are similar structures comprising antibody surrogate κ light chain sequences, where κ light chain sequences are optionally partnered with another polypeptide, such as, for example, antibody heavy and/or light chain domain sequences. A κ-like B cell receptor (κ-like BCR) has been identified, utilizing a κ-like surrogate light chain (κ-like SLC) (Frances et al., *EMBO J* 13:5937-43 (1994); Thompson et al., *Immunogenetics* 48:305-11 (1998); Rangel et al., *J Biol Chem* 280:17807-14 (2005)). Rangel et al., *J Biol Chem* 280(18):17807-17814 (2005) report the identification and molecular characterization of a Vκ-like protein that is the product of an unrearranged Vκ gene, which turned out to the be identical to the cDNA sequence previously reported by Thompson et al., *Immunogenetics* 48:305-311 (1998). Whereas, Frances et al., *EMBO J* 13:5937-43 (1994) reported the identification and characterization of a rearranged germline JCκ that has the capacity to associate with μ heavy chains at the surface of B cell precursors, thereby providing an alternative to the λ5 pathway for B cell development. It has been proposed that κ-like and λ-like pre-BCRs work in concert to promote light chain rearrangement and ensure the maturation of B cell progenitors. For a review, see McKeller and Martinez-Valdez *Seminars in Immunology* 18:4043 (2006).

The term "λ5" is used herein in the broadest sense and refers to any native sequence or variant λ5 polypeptide, specifically including, without limitation, native sequence human and other mammalian λ5 polypeptides, and variants formed by posttranslational modifications, as well a variants of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VprcB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another preferred embodiment, the "variant VpreB polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed. The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another preferred embodiment, the "variant λ5 polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant λ5 polypeptides specifically include, without limitation. λ5 polypeptides in which the unique tail at the N-terminus of the λ5 sequence is partially or completely removed.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term "surrogate light chain sequence," as defined herein, means any polypeptide sequence that comprises a "VpreB sequence" and/or a "λ5 sequence," as hereinabove defined.

The terms "κ-like surrogate light chain variable domain," "Vκ-like SLC," and "Vκ-like" are used interchangeably, and refer to any native sequence polypeptide that is the product of an un-rearranged Vκ gene, and variants thereof. In one embodiment, variants of native sequence Vκ-like polypeptides comprise a C-terminal extension (tail) relative to antibody κ light chain sequences. In a particular embodiment, variants of native sequence Vκ-like polypeptides retain at least part, and preferably all, of the unique C-terminal extension (tail) that distinguishes the Vκ-like polypeptides from the corresponding antibody κ light chains. In another embodiment, the C-terminal tail of the variant Vκ-like polypeptide is a sequence not naturally associated with the rest of the sequence. In the latter embodiment, the difference between the C-terminal tail naturally present in the native Vκ-like sequence and the variant sequence may result from one or more amino acid alterations (substitutions, insertions, deletions, and/or additions), or the C-terminal tail may be identical with a tail present in nature in a different Vκ-like protein. The Vκ-like polypeptides may contain amino acid alterations in regions corresponding to one or more of antibody κ light chain CDR1, CDR2 and CDR3 sequences. In all instances, the variants can, and preferably do, include a C-terminal extension of at least four, or at least five, or at least six, or at least seven, or at least eight, or at least nine, or at least ten amino acids, preferably 4-100, or 4-90, or 4-80, or 4-70, or 4-60, or 4-50, or 4-45, or 4-40, or 4-35, or 4-30, or 4-25, or 4-20, or 4-15, or 4-10 amino acid residues relative to a native antibody κ light chain variable region sequence. As defined herein, Vκ-like polypeptide variant will be different from a native antibody κ or λ light chain sequence or a fragment thereof, and will preferably retain at least about 65%, or at least about 70%, or at least about 75%, or at least about 80%, or at least about 85%, or at least about 90%, or at least about 95%, or at least about 98% sequence identity with a native sequence Vκ polypeptide. In another preferred embodiment, the Vκ-like polypeptide variant will be less than 95%, or less than 90%, or less than 85%, or less than 80%, or less than 75%, or less than 70%, or less than 65%, or less than 60%, or less than 55%, or less than 50%, or less than 45%, or less than 40% identical in its amino acid sequence to a native antibody λ or κ light chain sequence. In other embodiments, the sequence identity is between about 40% and about 95%, or between about 45% and about 90%, or between about 50% and about 85%, or between about 55% and about 80%, or between about 60% and about 75%, or between about 60% and about 80%, or between about 65% and about 85%, or between about 65% and about 90%, or between about 65% and about 95%. In all embodiments, preferably the Vκ-like polypeptides are capable of binding to a target.

The terms "JCκ" and "JCκ-like" are used interchangeably, and refer to native sequence polypeptides that include a portion identical to a native sequence κ J-constant (C) region segment and a unique N-terminal extension (tail), and variants thereof. In one embodiment, variants of native sequence JCκ-like polypeptides comprise an N-terminal extension (tail) that distinguishes them from an antibody JC segment. In a particular embodiment, variants of native sequence JCκ-like polypeptides retain at least part, and preferably all, of the unique N-terminal extension (tail) that distinguishes the JCκ-like polypeptides from the corresponding antibody κ light chain JC segments. In another embodiment, the N-terminal tail of the variant JCκ-like polypeptide is a sequence not naturally associated with the rest of the sequence. In the latter embodiment, the difference between the N-terminal tail naturally present in the native JCκ-like sequence and the variant sequence may result from one or more amino acid alterations (substitutions, insertions, deletions, and/or additions), or the N-terminal tail may be identical with a tail present in nature in a different JCκ-like protein. Variants of native sequence JCκ-like polypeptides may contain one or more amino acid alterations in the part of the sequence that is identical to a native antibody κ variable domain JC sequence. In all instances, the variants can, and preferably do, include an N-terminal extension (unique N-terminus) of at least four, or at least five, or at least six, or at least seven, or at least eight, or at least nine, or at least ten amino acids, preferably 4-100, or 4-90, or 4-80, or 4-70, or 4-60, 4-50, or 4-45, or 4-40, or 4-35, or 4-30, or 4-25, or 4-20, or 4-15, or 4-10 amino acid residues relative to a native antibody κ light chain JC sequence. The JCκ-like polypeptide variant, as defined herein, will be different from a native antibody λ or κ light chain JC sequence, or a fragment thereof, and will preferably retain at least about 65%, or at least about 70%, or at least about 75%, or at least about 80%, or at least about 85%, or at least about 90%, or at least about 95%, or at least about 98% sequence identity with a native sequence JC polypeptide. In another preferred embodiment, the JCκ-like polypeptide variant will be less than 95%, or less than 90%, or less than 85%, or less than 80%, or less than 75%, or less than 70%, or less than 65%, or less than 60% identical in its amino acid sequence to a native antibody A or κ light chain JC sequence. In other embodiments, the sequence identity is between about 40% and about 95%, or between about 45% and about 90%, or between about 50% and about 85%, or between about 55% and about 80%, or between about 60% and about 75%, or between about 60% and about 80%, or between about 65% and about 85%, or between about 65% and about 90%, or between about 65% and about 95%.

Percent amino acid sequence identity may be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822 (b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogues thereof (e.g., DNA or RNA generated using nucleotide analogues or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at a specified position," refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301 336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

The term "neutralizing molecule" is used herein in the broadest sense and refers to any molecule that inhibits a virus from replicatively infecting a target cell, irrespective of the mechanism by which neutralization is achieved, The neutralizing molecule preferably an antibody or an antibody-like molecule or binding molecule, as hereinabove defined, Neutralization can be achieved, for example, by inhibiting the attachment or adhesion of the virus to the cell surface, e.g., by engineering an molecule, such as an antibody or antibody-like molecule or binding molecule, that binds directly to, or close by, the site responsible for the attachment or adhesion of the virus. Neutralization can also be achieved by a molecule, such as an antibody or antibody-like molecule, directed to the virion surface, which results in the aggregation of virions. Neutralization can further occur by inhibition of the fusion of viral and cellular membranes following attachment of the virus to the target cell, by inhibition of endocytosis, inhibition of progeny virus from the infected cell, and the like. The neutralizing molecules, such as antibodies or antibody-like molecules or binding molecules, of the present invention are not limited by the mechanism by which neutralization is achieved.

The term "antibody repertoire" is used herein in the broadest sense and refers to a collection of antibodies or antibody fragments which can be used to screen for a particular property, such as binding ability, binding specificity, ability of gastrointestinal transport, stability, affinity, and the like. The term specifically includes antibody libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

Similarly, a "repertoire of antibody-like molecules" (as hereinabove defined) refers to a collection of such molecules which can be used to screen for a particular property, such as binding ability, binding specificity, ability of gastrointestinal transport, stability, affinity, and the like. The term specifically includes surrobody libraries and libraries of κ-like light chain constructs (as hereinabove defined), including all forms of combinatorial libraries, such as, for example, phage display libraries. Combinatorial surrobody libraries are disclosed, for example, in Xu et al., (2008), supra.

The term "antibody repertoire" is used herein in the broadest sense and refers to a collection of antibodies or antibody fragments which can be used to screen for a particular property, such as binding ability, binding specificity, ability of gastrointestinal transport, stability, affinity, and the like. The term specifically includes antibody libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

An "antibody phage display library" refers to a phage display library that displays antibodies or antibody fragments. The antibody library includes the population of phage or a collection of vectors encoding such a population of phage, or cell(s) harboring such a collection of phage or vectors. The library can be monovalent, displaying on average one single-chain antibody or antibody fragment per phage particle, or multi-valent, displaying, on average, two or more antibodies or antibody fragments per viral particle. The term "antibody fragment" includes, without limitation, single-chain Fv (scFv) fragments and Fab fragments. Preferred antibody libraries comprise on average more than $10^6$, or more than $10^7$, or more than $10^8$, or more than $10^9$ different members.

The term "filamentous phage" refers to a viral particle capable of displaying a heterogenous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al., Gene 9:127-140 (1980), Smith et al., Science 228:1315-1317 (1985); and Parmley and Smith, Gene 73:305-318 (1988)).

The term "panning" is used to refer to the multiple rounds of screening process in identification and isolation of phages carrying compounds, such as antibodies, with high affinity and specificity to a target.

The term "non-human animal" as used herein includes, but is not limited to, mammals such as, for example, non-human primates, rodents (e.g., mice and rats), and non-rodent animals, such as, for example, rabbits, pigs, sheep, goats, cows, pigs, horses and donkeys. It also includes birds (e.g., chickens, turkeys, ducks, geese and the like). The term "non-primate animal" as used herein refers to mammals other than primates, including but not limited to the mammals specifically listed above.

The phrase "functionally different antibodies," and grammatical variants thereof, are used to refer to antibodies that differ from each other in at least one property, including, without limitation, binding specificity, binding affinity, and any immunological or biological function, such as, for example, ability to neutralize a target, extent or quality of biological activity, etc.

The phrase "conserved amino acid residues" is used to refer to amino acid residues that are identical between two or more amino acid sequences aligned with each other.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, binds to an antibody generated in response to such sequence. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

B. General Techniques

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; *Antibody Phage Display: Methods and Protocols*, P. M. O'Brian and R. Aitken, eds., Humana Press, In: *Methods in Molecular Biology*, Vol. 178; *Phage Display: A Laboratory Manual*, C. F. Barbas III et al. eds., Cold Spring Harbor, N.Y., USA, Cold Spring Harbor Laboratory Press, 2001; and Antibodies, G. Subramanian, ed., Kluwer Academic, 2004. Mutagenesis can, for example, be performed using site-directed mutagenesis (Kunkel et al., *Proc. Natl. Acad. Sci USA* 82:488-492 (1985)).

In one aspect, the viral antigen neutralizing molecules of the present invention are antibodies, which are typically selected using antibody or diversified polypeptide libraries. In the following description, the invention is illustrated with reference to certain types of antibody libraries, but the invention is not limited to the use of any particular type of antibody or diversified polypeptide library. Recombinant monoclonal antibody libraries can be based on immune fragments or naïve fragments. Antibodies from immune antibody libraries are typically constructed with $V_H$ and $V_L$ gene pools that are cloned from source B cells into an appropriate vector for expression to produce a random combinatorial library, which can subsequently be selected for and/or screened. Other types of libraries may be comprised of antibody fragments from a source of genes that is not explicitly biased for clones that bind to an antigen. Thus, naïve antibody libraries derive from natural, unimmunized, rearranged V genes. Synthetic antibody libraries are constructed entirely by in vitro methods, introducing areas of complete or tailored degeneracy into the CDRs of one or more V genes. Semi-synthetic libraries combine natural and synthetic diversity, and are often created to increase natural diversity while maintaining a desired level of functional diversity. Thus, such libraries can, for example, be created by shuffling natural CDR regions (Soderlind et al., *Nat. Biotechnol.* 18:852-856 (2000)), or by combining naturally rearranged CDR sequences from human B cells with synthetic c CDR1 and CDR2 diversity (Hoet et al., *Nat. Biotechnol.* 23:455-38 (2005)). The present invention encompasses the use of naïve, synthetic and semi-synthetic antibody libraries, or any combination thereof.

Similarly, the methods of the present invention are not limited by any particular technology used for the display of antibodies. Although the invention is illustrated with reference to phage display, antibodies of the present invention can also be identified by other display and enrichment technologies. Antibody fragments have been displayed on the surface of filamentous phage that encode the antibody genes (Hoogenboom and Winter *J. Mol. Biol.*, 222:381 388 (1992); McCafferty et al., *Nature* 348(6301):552 554 (1990); Griffiths et al. *EMBO J.*, 13(14):3245-3260 (1994)). For a review of techniques for selecting and screening antibody libraries see, e.g., Hoogenboom, *Nature Biotechnol.* 23(9):1105-1116 (2005). In addition, there are systems known in the art for display of heterologous protcins and fragments thereof on the surface of *Escherichia coli*(Agterberg et al., *Gene* 88:37-45 (1990); Charbit et al., *Gene* 70:181-189 (1988); Francisco et al., *Proc. Natl. Acad. Sci. USA* 89:2713-2717 (1992)), and yeast, such as *Saccharomyces cerevisiae* (Boder and Wittrup, *Nat. Biotechnol.* 15:553-557 (1997); Kieke et al., *Protein Eng.* 10:1303-1310 (1997)). Other known display techniques include ribosome or mRNA display (Mattheakis et al., *Proc. Natl. Acad. Sci. USA* 91:9022-9026 (1994); Hanes and Pluckthun, *Proc. Natl. Acad Sci. USA* 94:4937-4942 (1997)), DNA display (Yonezawa et al., *Nucl. Acid Res.* 31(19):e118 (2003)); microbial cell display, such as bacterial display (Georgiou et al., *Nature Biotech.* 15:29-34 (1997)), display on mammalian cells, spore display (Isticato et al., *J. Bacteriol.* 183: 6294-6301 (2001); Cheng et al., *Appl. Environ. Microbiol.* 71:3337-3341 (2005) and provisional application Ser. No. 60/865,574, filed Nov. 13, 2006), viral display, such as retroviral display (Urban et al., *Nucleic Acids Res.* 33:e35 (2005), display based on protein-DNA linkage (Odegrip et al., *Proc. Acad. Natl. Sci. USA* 101:2806-2810 (2004); Reiersen et al., *Nucleic Acids Res.* 33:e10 (2005)), and microbead display (Sepp et al., *FEBS Lett.* 532:455-458 (2002)).

C. Detailed Description of Preferred Embodiments

In one aspect, the present invention concerns the selection, production and use of monoclonal antibodies and antibody-like molecules neutralizing more than one subtype and/or more than one isolate of an influenza A virus, binding to a hemagglutinin (HA) antigen of the virus, but not inhibiting hemagglutination.

The virions of influenza A virus contain 8 segments of linear negative-sense single stranded RNA. The total genome length is 13600 nucleotides, and the eight segments are 2350 nucleotides; 2350 nucleotides; of 2250 nucleotides; 1780 nucleotides; 1575 nucleotides; 1420 nucleotides; 1050 nucleotides; and 900 nucleotides, respectively, in length. Host specificity and attenuation of influenza A virus have been attributed to viral hemagglutinin (H, HA), nucleoprotein (NP), matrix (M), and non-structural (NS) genes individually or in combinations of viral genes (see, e.g., Rogers et al., *Virology* 127:361-373 (1983); Scholtissek et al., *Virology* 147:287-294 (1985); Snyder et al., *J. Clin. Microbiol.* 24:467-469 (1986); Tian et al., *J. Viral.* 53:771-775 (1985); Treanor et al., *Virology* 171:1-9 (1989).

Nucleotide and amino acid sequences of influenza A viruses and their surface proteins, including hemagglutinins and neuraminidase proteins, are available from GenBank and other sequence databases, such as, for example, the Influenza Sequence Database maintained by the Theoretical Biology and Biophysics Group of Los Alamos National Laboratory. The amino acid sequences of 15 known H subtypes of the influenza A virus hemagglutinin (H1-H15) are shown in U.S. Application Publication No. 20080014205, published on Jan. 17, 2008, incorporated herein by reference in its entirety. An additional influenza A virus hemagglutinin subtype (H16) was isolated recently from black-headed gulls in Sweden, and reported by Fouchier et al., *J. Virol.* 79(5):2814-22 (2005). A large variety of strains of each H subtype are also known. For example, the sequence of the HA protein designated H5 A/Hong Kong/156/97 was determined from an influenza A H5N1 virus isolated from a human in Hong Kong in May 1997, and is shown in comparison with sequences of several additional strains obtained from other related H5N1 isolates in Suarez et al., *J. Virol.* 72:6678-6688 (1998).

The structure of the catalytic and antigenic sites of influenza virus neuraminidase have been published by Colman et al., *Nature* 303:41-4 (1983), and neuraminidase sequences are available from GenBank and other sequence databases.

It has been known that virus-specific antibodies resulting from the immune response of infected individuals typically neutralize the virus via interaction with the viral hemagglutinin (Ada et al., *Curr. Top. Microbiol. Immunol.* 128:1-54 (1986); Couch et al., *Annu. Rev. Micobiol.* 37:529-549 (1983)). The three-dimensional structures of influenza virus hemagglutinins and crystal structures of complexes between influenza virus hemagglutinins and neutralizing antibodies have also been determined and published, see, e.g., Wilson et al., *Nature* 289:366-73 (1981); Ruigrok et al., *J. Gen. Virol.* 69 (Pt 11):2785-95 (1988); Wrigley et al., *Virology* 131(2):308-14 (1983); Daniels et al., *EMBO J.* 6:1459-1465 (1987); and Bizebard et al., *Nature* 376:92-94 (2002).

According to the present invention, antibodies with the desired properties are identified from one or more antibody libraries, which can come from a variety of sources and can be of different types.

Comprehensive Human Influenza Antibody Libraries

Comprehensive human influenza antibody libraries can be created from antibodies obtained from convalescent patients of various prior influenza, seasonal outbreaks epidemics, and pandemics, including the 1968 Hong Kong flu (H3N2), the 1957 Asian flu (H2N2), the 1918 Spanish flu (H1N1), and the 2004/2005 Avian flu (H5N1). For example, see U.S. Application Publication No. 20080014205, published on Jan. 17, 2008, incorporated herein by reference in its entirety. In order to prepare such libraries, blood or bone marrow samples are collected from individuals known or suspected to have been infected with an influenza virus. Peripheral blood samples, especially from geographically distant sources, may need to be stabilized prior to transportation and use. Kits for this purpose are well known and commercially available, such as, for example, BD Vacutainer® CPT™ cell preparation tubes can be used for centrifugal purification of lymphocytes, and guanidium, Trizol, or RNAlater used to stabilize the samples. Upon receipt of the stabilized lymphocytes or whole bone marrow, RT-PCR is performed to rescue heavy and light chain repertoires, using immunoglobulin oligo primers known in the art. The PCR repertoire products are combined with linker oligos to generate scFv libraries to clone directly in frame with m13 pIII protein, following procedures known in the art.

In a typical protocol, antibodies in the human sera can be detected by well known serological assays, including, for example, by the well-known hemagglutinin inhibition (HAI) assay (Kendal, A. P., M. S. Pereira, and J. J. Skehel. 1982. *Concepts and procedures for laboratory-based influenza surveillance*. U.S. Department of Health and Human Services, Public Health Service, Centers for Disease Control, Atlanta, Ga.), or the microneutralization assay (Harmon et al., *J. Clin. Microbiol.* 26:333-337 (1988)). This detection step might not be necessary if the serum sample has already been confirmed to contain influenza neutralizing antibodies. Lymphocytes from whole blood or those present in bone marrow are next processed by methods known in the art. Whole RNA is extracted by Tri BD reagent (Sigma) from fresh or RNAlater stabilized tissue. Subsequently, the isolated donor total RNA is further purified to mRNA using Oligotex purification (Qiagen). Next first strand cDNA synthesis, is generated by using random nonamer oligonucleotides and or oligo $(dT)_{18}$ primers according to the protocol of AccuScript reverse transcriptase (Stratagene). Briefly, 100 ng mRNA, 0.5 mM dNTPs and 300 ng random nonamers and or 500 ng oligo $(dT)_{18}$ primers in Accuscript RT buffer (Stratagene) are incubated at 65° C. for 5 min, followed by rapid cooling to 4° C. Then, 100 mM DTT, Accuscript RT, and RNAse Block are added to each reaction and incubated at 42° C. for 1 h, and the reverse transcriptase is inactivated by heating at 70° C. for 15 minutes. The cDNA obtained can be used as a template for RT-PCR amplification of the antibody heavy and light chain V genes, which can then be cloned into a vector, or, if phage display library is intended, into a phagemid vector. This procedure generates a repertoire of antibody heavy and light chain variable region clones ($V_H$ and $V_L$ libraries), which can be kept separate or combined for screening purposes.

Immunoglobulin repertoires from peripheral lymphocytes of survivors of earlier epidemics and pandemics, such as the 1918 Spanish Flu, can be retrieved, stabilized, and rescued in a manner similar to that described above. For additional H1 and H3 libraries repertoires can be recovered from properly timed vaccinated locally-sourced donors. As an additional option commercially available bone marrow total RNA or mRNA can be purchased from commercial sources to produce libraries suitable for H1 and H3, and depending upon the background of donor also suitable for H2 antibody screening.

Synthetic Human-Like Repertoire

In the methods of the present invention, the synthetic human antibody repertoire can be represented by a synthetic antibody library, which can be made by methods known in the art or obtained from commercial sources. Thus, for example, a fully synthetic human repertoire is described in Horowitz et al. U.S. Patent Application Publication No. 20090082213 published on Mar. 26, 2009, the entire disclosure of which is hereby expressly incorporated by reference. In brief, this patent application describes libraries of immunoglobulins in which predetermined amino acids have been combinatorially introduced into one or more complementarity-determining regions of the immunoglobulin of interest. Additionally, for example, a universal immunoglobulin library, including subsets of such library, are described in U.S. Patent Application Publication No. 20030228302 published on Dec. 11, 2003, the entire disclosure of which is hereby expressly incorporated by reference.

Specific sublibraries of antibody heavy and light chains with various mutations can be combined to provide the framework constructs for the antibodies of the present invention, which is followed by introducing diversity in the CDRs of both heavy and light chains. This diversity can be achieved by methods known in the art, such as, for example, by Kunkel mutagenesis, and can be repeated several times in order to further increase diversity. Thus, for example, diversity into the heavy and light chain CDR1 and CD2 regions, separately or simultaneously, can be introduced by multiple rounds of Kunkel mutagenesis. If necessary, the various Kunkel clones can be segregated by CDR lengths and/or clones lacking diversity in a targeted CDR (e.g., CDR1 or CDR3) can be removed, e.g., by digestion with template-specific restriction enzymes. Upon completion of these steps, the size of the library should exceed about $10^9$ members, but libraries with lesser members are also useful.

In a specific embodiment, both immunized antibody libraries and synthetic antibody libraries are used for identifying the neutralizing antibodies of the present invention. The two types of libraries are fundamentally different. The synthetic antibody libraries are synthesized collections of human antibodies with the predicted ability to bind antigens, while an immunized repertoire will contain sequences to specifically recognize avian H5 hemagglutinin, and/or H1, H2, or H3 hemagglutinin, as the case may be. Thus, the immunized repertoires are theoretically optimized to recognize critical components of targeted influenza subtype(s). As a result these differences the two methods produce a different set of antibodies and thus provide a more efficient approach for identifying the desired neutralizing antibodies.

Hyperimmunized Non-Human Primate Antibody Libraries

In this method, an antibody library is rescued from hyperimmunized non-human primates, such as, for example, macaque or baboons. Specifically, non-human primates are immunized with various subtypes of the influenza A virus or with various hemagglutinin (H) proteins. Animals developing titers of antibody recognizing the influenza A virus subtype or hemagglutinin they were immunized with are sacrificed and their spleens harvested. Blood or bone marrow of the immunized animals is collected, and antibodies produced are collected and amplified as described above for the comprehensive influenza antibody libraries.

Strategies for Isolating Neutralizing Antibodies of the Invention

Regardless of the type of antibody library or libraries used, antibodies with dual specificities, such as, for example, showing reactivity with two different influenza A subtypes and/or with two strains (isolates) of the same subtype, and/or with human and non-human isolates, can be discovered and optimized through controlled cross-reactive selection and/or directed combinatorial and/or mutagenic engineering.

In a typical enrichment scheme, illustrated in FIG. 1, a library including antibodies showing cross-reactivity to two targets, designated as targets A and B, are subjected to multiple rounds of enrichment (see U.S. Application Publication No. 20080014205, published on Jan. 17, 2008, incorporated herein by reference in its entirety). If enrichment is based on reactivity with target A, each round of enrichment will increase the reactive strength of the pool towards target A. Similarly, if enrichment is based on reactivity with target B, each round of enrichment will increase the reactive strength of the pool towards target B. Although this approach refers to panning, which is the selection method used when screening phage display libraries (see below), the approach is equally applicable to any type of library discussed above, other otherwise known in the art, and to any type of display technique. Targets A and B include any targets to which antibodies bind, including but not limited to various isolates, types and sub-types of influenza viruses.

Since the goal of the present invention is to identify neutralizing antibodies with multiple specificities, a cross-reactive discovery selection scheme has been developed. In the interest of simplicity, this scheme is illustrated in FIG. 2 showing the selection of antibodies with dual specificities. In this case, an antibody library including antibodies showing reactivity with two targets, targets A and B, is first selected for reactivity with one of the targets, e.g., target A, followed by selection for reactivity with the other target, e.g., target B. Each successive selection round reinforces the reactive strength of the resulting pool towards both targets. (see also U.S. Application Publication No. 20080014205, published on Jan. 17, 2008, incorporated herein by reference in its entirety). Accordingly, this method is particularly useful for identifying antibodies with dual specificity. Of course, the method can be extended to identifying antibodies showing reactivity towards further targets, by including additional rounds of enrichment towards the additional target(s). Again, if the library screened is a phage display library, selection is performed by cross-reactive panning, but other libraries and other selection methods can also be used.

A combination of the two methods discussed above includes two separate enrichment rounds for reactivity towards target A and target B, respectively, recombining the two pools obtained, and subsequent cross-reactive selection rounds, as described above (see U.S. Application Publication No. 20080014205, published on Jan. 17, 2008, incorporated herein by reference in its entirety). This approach is illustrated in FIG. 1. Just as in the pure cross-reactive selection, each round of selection of the recombined library increases the reactive strength of the resulting pool towards both targets.

In a further embodiment, illustrated in FIG. 2, first a clone showing strong reactivity with a target A, and having detectable cross-reactivity with target B is identified. Based on this clone, a mutagenic library is prepared, which is then selected, in alternating rounds, for reactivity with target B and target A respectively. This scheme will result in antibodies that maintain strong reactivity with target A, and have increased reactivity with target B (see U.S. Application Publication No. 20080014205, published on Jan. 17, 2008, incorporated herein by reference in its entirety). Just as before, selection is performed by panning, if the libraries screened are phage display libraries, but other libraries, other display techniques, and other selection methods can also be used, following the same strategy.

As discussed above, targets A and B can, for example, be two different subtypes of the influenza A virus, two different strains (isolates) of the same influenza A virus, subtypes or isolates from two different species, where one species is preferably human. Thus, for example, target A may be an isolate of the New Caledonia isolate of the H1N1 virus, and target B may be the Wisconsin isolate of the H3N2 virus. It is emphasized that these examples are merely illustrative, and antibodies with dual and multiple specificities to any two or multiple targets can be identified, selected and optimized in an analogous manner.

Alternatively, if an antibody library such as the UAL that allows segregation of discrete frameworks and CDR lengths is used to find an antibody to target A, then an antigen B could be screened for and the library could be restricted to a diverse collection of similar parameters. Once an antibody to antigen B is found then chimeric or mutagenic antibodies based upon the respective A and B antibodies could be used to engineer a dual specific collection.

Phage Display

In a particular embodiment, the present invention utilizes phage display antibody libraries to functionally discover neutralizing monoclonal antibodies with multiple (including dual) specificities. Such antibodies can, for example, be monoclonal antibodies capable of neutralizing more than one influenza A virus subtype, including the H1, H13 and/or the H9 subtypes, the H5, H7 and/or H9 subtypes, such as the H1 and H3, H5 and H1; H5 and H2; H5 and H3; H5, H1, and H2; H5, H1, and H3; H5, H2 and H3; H1, H2 and H3, etc., subtypes, and/or more than one strain (isolate) of the same subtype.

To generate a phage antibody library, a cDNA library obtained from any source, including the libraries discussed above, is cloned into a phagemid vector.

Thus, for example, the collection of antibody heavy and light chain repertoires rescued from lymphocytes or bone marrow by RT-PCR as described above, is reassembled as a scFv library fused to m13 pIII protein. The combinatorial library will contain about more than $10^6$, or more than $10^7$, or more than $10^8$, or more than $10^9$ different members, more than $10^7$ different members or above being preferred. For quality control random clones are sequenced to assess overall repertoire complexity.

Similarly, following the initial PCR rescue of heavy and light chain variable regions from a naïve or immunized human, or hyperimmunized nonhman primate antibody library, the PCR products are combined with linker oligos to generate scFv libraries to clone directly in frame with M13 pIII coat protein. The library will contain about more than $10^6$, or more than $10^7$, or more than $10^8$, or more than $10^9$ different members, more than $10^7$ different members or above being preferred. As a quality control step, random clones are sequenced in order to assess overall repertoire size and complexity.

Antibody phage display libraries may contain antibodies in various formats, such as in a single-chain Fv (scFv) or Fab format. For review see, e.g., Hoogenboom, *Methods Mol. Biol.* 178:1-37 (2002).

Screening

Screening methods for identifying antibodies with the desired neutralizing properties have been described above. Reactivity can be assessed based on direct binding to the desired hemagglutinin proteins.

Hemagglutinin (HA) Protein Production

Hemagglutinin (HA) proteins can be produced by recombinant DNA technology. In this method, HA genes are cloned into an appropriate vector, preferably a baculovirus expression vector for expression in baculovirus-infected insect cells, such as *Spodoptera frugiperda* (Sf9) cells.

The nucleic acid coding for the HA protein is inserted into a baculovirus expression vector, such as Bac-to-Bac (Invitrogen), with or without a C-terminal epitope tag, such as a poly-his (hexahistidine tag). A poly-his tag provides for easy purification by nickel chelate chromatography.

In general the cloning involves making reference cDNAs by assembly PCR from individually synthesized oligos. Corresponding isolate variant HA proteins are made by either substituting appropriate mutant oligos into additional assembly PCRs or by mutagenesis techniques, such as by Kunkel mutagenesis.

Recombinant baculovirus is generated by transfecting the above Bacmid into Sf9 cells (ATCC CRL 1711) using lipofectin (commercially available from Gibco-BRL). After 4-5 days of incubation at 28° C., the released viruses are harvested and used for further amplifications. Viral infection and protein expression are performed as described by O'Reilley et al., *Baculovirus Expression Vectors: A Laboratory Manual* (Oxford: Oxford University Press, 1994).

Expressed poly-His-tagged HA polypeptides can then be purified, for example, by $Ni^{2+}$-chelate affinity chromatography as follows. Supernatents are collected from recombinant virus-infected Sf9 cells as described by Rupert et al., *Nature* 362:175-179 (1993). A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non-specifically bound protein. After reaching $A_{280}$ baseline again, the column is developed with a 0 to 500 mM imidazole gradient in the secondary wash buffer. One-mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged HA polypeptide are pooled and dialyzed against loading buffer.

Alternatively, purification of an IgG-tagged (or Fc-tagged) HA polypeptide can be performed using known chromatography techniques, including, for instance, Protein A or protein G column chromatography.

As an alternative to using Sf9 cells HA proteins can also be produced in other recombinant host cells, prokaryote, yeast, or higher eukaryote cells. Suitable prokaryotes include but are not limited to eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635).

In addition to prokaryotes, eukaryotic microbes such as filamentous fungi or yeast are suitable cloning or expression hosts for vectors containing nucleic acid encoding an HA polypeptide. *Saccharomyces cerevisiae* is a commonly used lower eukaryotic host microorganism. However, a number of other genera, species, and strains are commonly available and useful herein, such as *Schizosaccharomyces pombe* (Beach and Nurse, *Nature* 290: 140 (1981); EP 139,383 published 2 May 1985); *Kluyveromyces* hosts (U.S. Pat. No. 4,943,529; Fleer et al., *Bio/Technology* 9:968-975 (1991)) such as, e.g., *K. lactis* (MW98-8C, CBS683, CBS4574; Louvencourt et al., *J. Bacteriol.* 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology* 8:135 (1990)), *K. thermotolerans*, and *K. marxianus; yarrowia* (EP 402,226); *Pichia pastoris* (EP 183,070; Sreekrishna et al., *J. Basic Microbiol.* 28:265-278 (1988)); *Candida; Trichoderma reesia* (EP 244,234); *Neurospora crassa* (Case et al., *Proc. Natl. Acad. Sci. USA* 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* 112:284-289 (1983); Tilburn et al., *Gene* 26:205-221 (1983); Yelton et al., *Proc. Natl. Acad. Sci. USA* 81:1470-1474 (1984)) and *A. niger* Kelly and Hynes, EMBO J. 4:475-479 (1985). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs* 269 (1982).

Suitable host cells for the expression of HA proteins include cells of multicellular organisms. Examples of invertebrate cells include the above-mentioned insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (HEK 293 or HEK 293 cells subcloned for growth in suspension culture (Graham et al., *J. Gen Virol.* 36:59 (1977)); Chinese hamster ovary cells/-DHFR (CHO, Urlaub and Chasin, *Proc. Natl. Acad. Sci. USA* 77:4216 (1980)); mouse sertoli cells (TM4, Mather, *Biol. Reprod.* 23:243-251 (1980)); human lung cells (W138, ATCC CCL75); human liver cells (Hep G2, HB 8065); and mouse mammary tumor (MMT 060562, ATCC CCL51). The selection of the appropriate host cell is deemed to be within the skill in the art.

Hemagglutinin (HA) Protein Panning

HA protein is immobilized on to the surface of microtiter wells or magnetic beads to pan the described above libraries. In a particular embodiment, each library is allowed to bind one or more H proteins at 4 degrees for two hours and then washed extensively with cold PBS, before eluting HA specific binding clones with 0.2M glycine-HCl buffer (pH2.5). The recovered phage is pH neutralized and amplified by infecting a susceptible host *E. coli*. Subsequently, phagemid production can be induced to repeat the enrichment of positive clones and subsequent clones isolation for triage. Upon sufficient enrichment the entire pool is transferred by infection into a non amber suppressor *E. coli* strain such as HB2151 to express soluble scFv proteins. Alternatively the pool(s) could be subcloned into a monomeric scFv expression vector, such as pBAD, and recombinant soluble scFv proteins are expressed for in vitro analysis and characterization, as described below.

Characterization

Clones are tested for binding affinity to one or more H proteins, as described above. For example, binding is tested to an H1 protein (Refseq ABQ10137, Isolate New Caledonia/20/99 (H1N1) and/or Refseq ABU99069, Isolate Solomon Islands/3/06 (H1N1)), and in parallel test to an H3 protein (Refseq ACC67032, Isolate Wisconsin/67/05 (H3N2), and/or Refseq CAA24269, Hong Kong/68 (H3N2), but other isolates can also be used alone or in any combination. The positive clones obtained based on the demonstrated binding can be tested for neutralizing ability. The typical functional test for neutralization involves hemagglutination inhibition assays using whole virus binding to red blood cells. Alternatively, hemagglutination assays with recombinant hemagglutinin protein and red blood cells are possible. In order to eliminate the need for whole blood, the hemagglutinin binding inhibition assay can be performed on airway epithelial cells. The binding assay can be performed in any configuration, including, without limitation, any flow cytometric or cell ELISA (cELISA) based assays. Using cELISA is advantageous in that it obviates the use of expensive flow cytometry equipment and can provide for more automated clonal assessment and greater data collection. On the other hand, flow cytometry may provide greater sensitivity, consistency, and speed.

In one aspect, the antibodies of the present invention have a binding affinity for an H1 HA containing influenza virus and/or an H3 HA containing influenza virus. Binding affinities of the antibodies of the present invention can be determined by methods known to those of skill in the art, for example by the Scatchard analysis of Munson et al., Anal. Biochem., 107:220 (1980). In one embodiment, the binding affinity is <100 pM. In other embodiments, the binding affinity of the antibody is from about $1\times10^{-7}$ to about $1\times10^{-13}$ M, from about $1\times10^{-8}$ to about $1\times10^{-12}$ M, or from about $1\times10^{-9}$ to about $1\times10^{-11}$ M. In other embodiments, the binding affinity of the antibody is about $1\times10^{-7}$ M, about $1\times10^{-8}$ M, about $1\times10^{-9}$ M, about $1\times10^{-1\times10}$ M, about $1\times10^{-11}$ M, about $1\times10^{-12}$ M, or about $1\times10^{-13}$ M.

Optimization: Mutagenesis Libraries

For the efficient management of influenza epidemics and pandemics, including a potential pandemic associated with human infections caused by a non-human animal virus, antibodies that effectively neutralize current isolates of the H proteins, as well as future mutations, are needed. In order to achieve this goal, diverse H (e.g., H1, H3, H5, etc.) neutralizing clones need to be identified that bind all known isolates of the targeted hemagglutinin subtype(s).

Cross-reactive antibodies, in some instances, emerge through directed screening against single antigens. To increase the likelihood of isolating cross-reactivity cones one would apply multiple selective pressures by processively screening against multiple antigens. In either event cross-reactivity can be further improved by antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

One mutagenic method designed to intentionally introduce cross-reactivity of the antibodies herein with more than one influenza A subtype and/or more than one isolate of the same subtype, is referred herein as "destinational" mutagenesis. Destinational mutagenesis can be used to rationally engineer a collection of antibodies based upon one or more antibody clones, preferably of differing reactivities. In the context of the present invention, destinational mutagenesis is used to encode single or multiple residues defined by analogous positions on like sequences such as those in the individual CDRs of antibodies. In this case, these collections are generated using oligo degeneracy to capture the range of residues found in the comparable positions. It is expected that within this collection a continuum of specificities will exist between or even beyond those of the parental clones. The objective of destinational mutagenesis is to generate diverse multifunctional antibody collections, or libraries, between two or more discrete entities or collections. In the case of influenza this method can be utilized to use two antibodies that recognize two distinct epitopes, isolates, or subtypes and morph both functional qualities into a single antibody. As an example, a first influenza A antibody can be specific to an isolate of the H1 subtype and a second antibody is specific to an isolate of the H3 subtype of the influenza A virus. To create a destinational mutagenesis library, the CDR sequences for both antibodies are first attained and aligned. Next all positions of conserved identity are fixed with a single codon to the matched residue. At non-conserved positions a degenerate codon is incorporated to encode both residues. In some instances the degenerate codon will only encode the two parental residues at this position. However, in some instances additional co-products are produced. The level of co-product production can be dialed in to force co-product production or eliminate this production dependent upon size limits or goals.

Thus, for example, if the first position of the two antibodies respectively are threonine and alanine, the degenerate codon with A/G-C- in the first two positions would only encode threonine or alanine, irrespective of the base in the third position. If, for example, the next position residues are lysine and arginine the degenerate codon A-A/G-A/G will only encode lysine or arginine. However, if the degenerate codon A/C-A/G-A/G/C/T were used then asparagine, histidine, glutamine, and serine coproducts will be generated as well.

Figure 3:
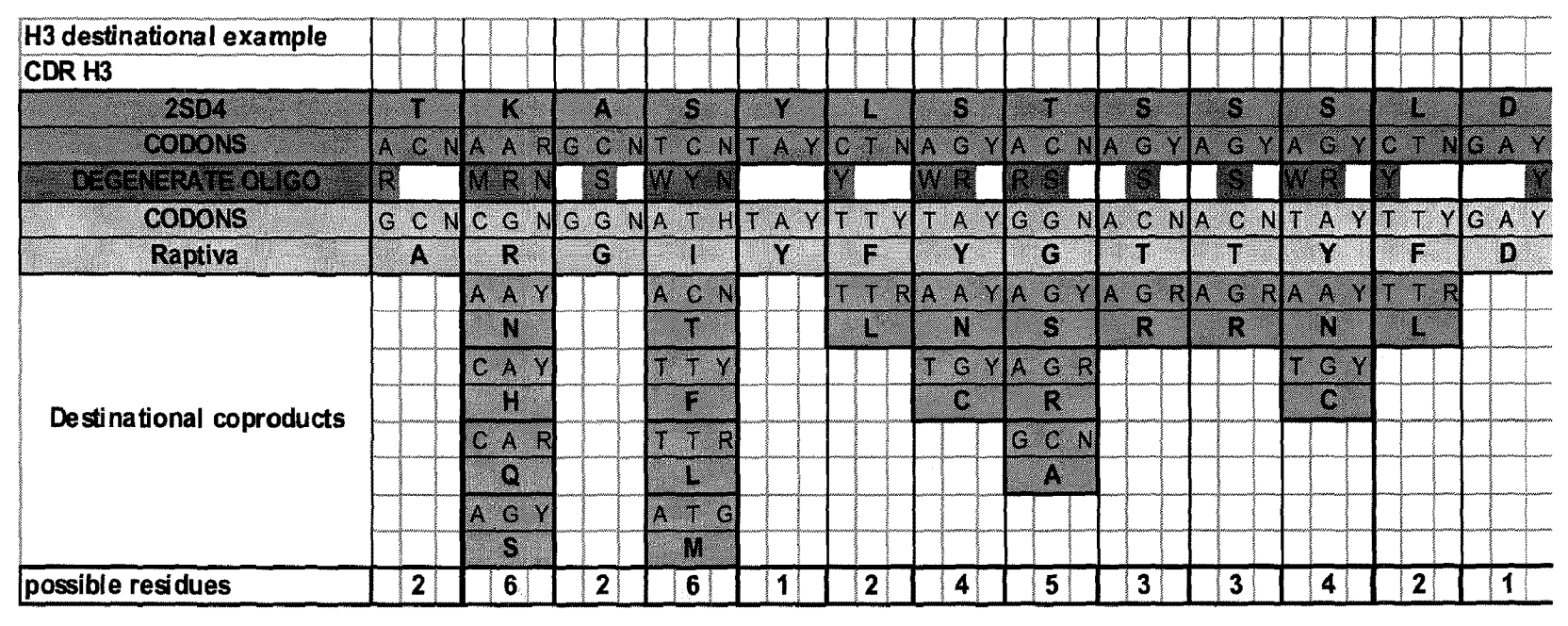

As a convenience it is simpler to use only antibodies with matched CDR lengths. One way to force this is to screen a size restricted library for the second antigen, based on the CDR length and potentially even framework restrictions imparted by the initially discovered antibody. It is noted, however, that using CDRs of equal length is only a convenience and not a requirement. It is easy to see that, while this method will be useful to create large functionally diverse libraries of influenza A virus neutralizing antibodies, its applicability is much broader. This mutagenesis technique can be used to produce functionally diverse libraries or collections of any antibody (see U.S. Application Publication No. 20080014205, published on Jan. 17, 2008 and incorporated herein by reference in its entirety). Thus, FIG. 3 is included herein to illustrate the use of the destinational mutagenesis method using CDRs of a TNF-α antibody and a CD11a antibody as the parental sequences mutagenized.

As crossreactivity is not commonly selected for naturally it is likely that executing typical mutagenic strategies may not enable potent crossreactivity. Destinational mutagenesis was devised as a directed method to generate spectrums of antibodies with crossreactive potention. Alternatively CDR amalgamation may provide another rapid and potent strategy for the creation and/or optimization of cross-reactive antibodies. It is well established that antigen binding and specificity is heavily influenced by differing combinations of selected CDRs from either or both chains. As the CDRs contained in preexisting antibodies may already be pre-optimized against target, one could create single antibodies, or collections of antibodies composed of CDR amalgams from multiple antibodies, as depicted in FIG. 6, that may prove effective against heterogeneous targets.

Figure 6:
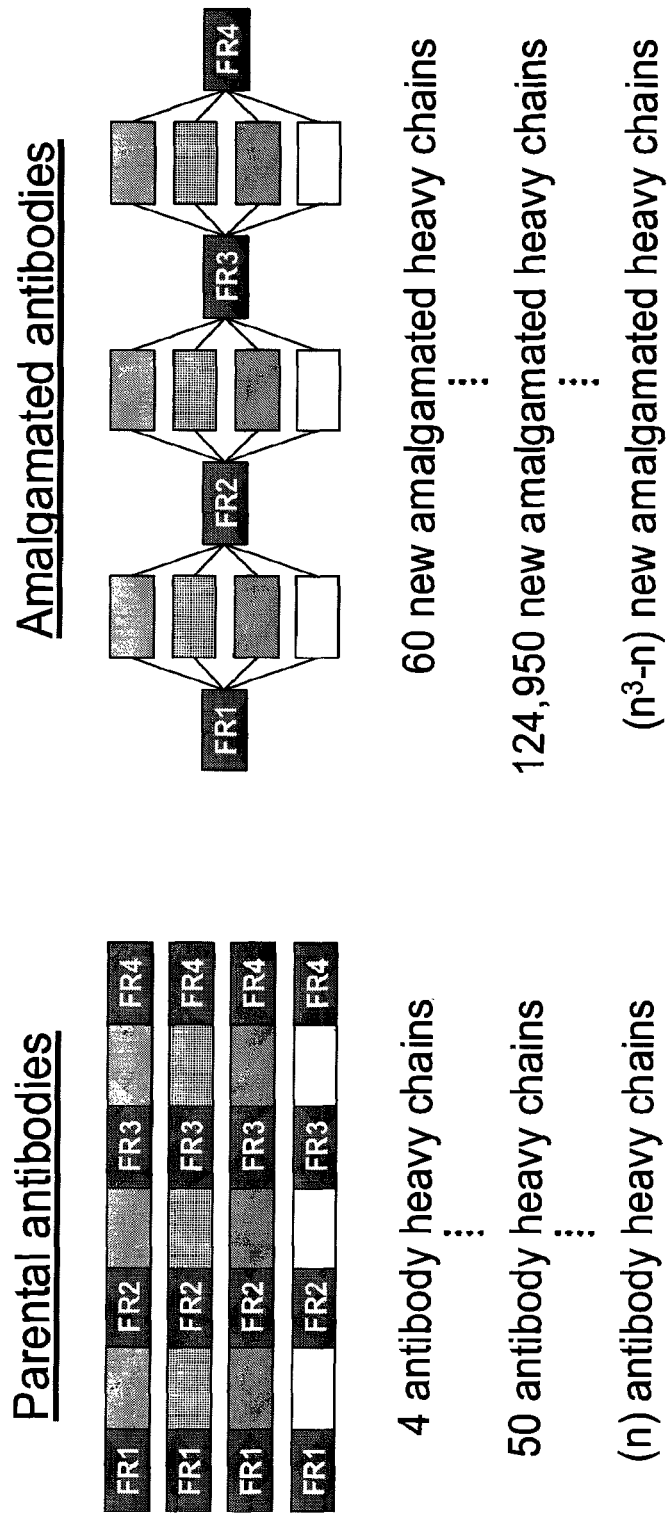
FIG. 6 illustrates a representative method for generating an amalgamated antibody library.

In FIG. 6, CDR amalgamated antibodies are depicted as a combinatorial superimposition of CDRs upon a single framework, but they could be superimposed upon multiple related and unrelated frameworks, or even chimeric frameworks thereof, increasing the overall diversity and productivity of the resulting amalgamated antibody or antibodies. Amalgamated libraries have the benefit of leveraging productive diversity found in existing antibodies, and the capacity to identify numerous new antibodies per amalgamated collection. This broader utilization of additional heavy chain frameworks allow sampling of binding in the context of CDR and framework variants that allow combinations not attainable in conventional B cell maturation from where greater crossreactivity and potency could be derivatized. As CDRs serve as interactive loops to engage target, one could create far more extensive combinations by mixing CDRs between both heavy and light chains, respective and irrespective of their original placements.

If more conventional optimization is sufficient to increase potency or spectrum of activity then targeted random mutagenesis, saturation mutagenesis, or even error-prone PCR could be utilized.

Targeted random mutagenesis (Matteuchi and Heyneker, *Nucleic Acids Research* 11: 3113-3121 (1983)) using ambiguously synthesized oligonucleotides is a technique that generates an intended codon as well as all possible codons at specific ratios, with respect to each other, at designated positions. Ambiguously synthesized oligonucleotides result in the reduced accuracy of nucleotide addition by the specific addition of non "wild type" bases at designated positions, or codons. This is typically performed by fixing the ratios of wild type and non wild type bases in the oligonucleotide synthesizer and designating the mixture of the two reagents at the time of synthesis.

Saturation mutagenesis (Hayashi et al., *Biotechniques* 17:310-315 (1994)) is a technique in which all 20 amino acids are substituted in a particular position in a protein and clones corresponding to each variant are assayed for a particular phenotype. (See, also U.S. Pat. Nos. 6,171,820; 6,358,709 and 6,361,974.)

Error prone PCR (Leung et al., *Technique* 1:11-15 (1989); Cadwell and Joyce, *PCR Method Applic.* 2:28-33 (1992)) is a modified polymerase chain reaction (PCR) technique introducing random point mutations into cloned genes. The resulting PCR products can be cloned to produce random mutant libraries or transcribed directly if a T7 promoter is incorporated within the appropriate PCR primer.

Other mutagenesis techniques are also well known and described, for example, in *In Vitro Mutagenesis Protocols*, J. Braman, Ed., Humana Press, 2001.

Optimization: Selection Considerations for Mutagenesis Library Screening

In the present case, one of the main goals is to engineer and isolate an antibody (or antibodies), from a collection, to effectively treat current H1 and/or H3 (or H5 or H9) isolates as well as future mutations. To engineer an antibody with tolerances capable of recognizing mutations in new isolates H1/H3, neutralizing clones that bind a variety of H1/H3 isolates need to be identified. It is expected that if a clone is selected on a first H1/H3 isolate it will bind/neutralize a second H1/H3 isolate to a lesser degree. In this case the goal is to improve recognition of the second H1/H3 isolate dramatically within the context of improving (or at least maintaining) the first H1/H3 isolate binding. Therefore, selection is first done for improvements on second H1/H3 reference protein followed by selection on the first H/H3 protein. Doing so provides a greater selective pressure on the new strain, while maintaining pressure on the second parameter.

Other H neutralizing antibodies can be optimized in an analogous manner. In this case one can select and optimize using any reference protein sequences from other isolates (e.g., H5, H9, etc.), and current as either a starting point or destination.

In addition, intertype recognition is tested with the neutralizing antibody clones. An example of intertype recognition is coincidental or engineered H1 binding from a non-H1 sourced or optimized clone.

In aggregate, the multiple mutagenesis collections and screens can be based upon the C5 and A11 antibodies, the C5-like and A11-like antibodies, C5 and A11 antibody-like molecules, C5 and C5-like surrobodies, and A11 and A11-like surrobodies. Whereby, each of the aforementioned molecules could be subject to any and all of the selections mentioned above to isolate appropriately reactive molecules that have broad spectrum reactivity and high potency.

Epitope Mapping of Neutralizing Antibodies

Once neutralizing antibodies with the desired properties have been identified, it might be desirable to identify the dominant epitope or epitopes recognized by the majority of such antibodies. Methods for epitope mapping are well known in the art and are disclosed, for example, in Morris, Glenn E., *Epitope Mapping Protocols*, Totowa, N.J. ed., Humana Press, 1996; and *Epitope Mapping: A Practical Approach*, Westwood and Hay, eds., Oxford University Press, 2001.

Epitope mapping concerns the identification of the epitope to which an antibody binds. There are many methods known to those of skill in the art for determining the location of epitopes on proteins, including crystallography analysis of the antibody-antigen complex, competition assays, gene fragment expression assays, and synthetic peptide-based assays (see for example, in Chapter 11 of Harlow and Lane, Using Antibodies, a Laboratory Manual, Cold Spring Harbor Laboratory Press, Cold Spring Harbor, N.Y., 1999; U.S. Pat. No. 7,332,579, each of which is incorporated herein by reference in its entirety). An antibody binds "essentially the same epitope" as a reference antibody, when the two antibodies recognize epitopes that are identical or sterically overlapping epitopes. A commonly used method for determining whether two antibodies bind to identical or sterically overlapping epitopes is the competition assay, which can be configured in all number of different formats, using either labeled antigen or labeled antibody. Usually, an antigen is immobilized on a 96-well plate, and the ability of unlabeled antibodies to block the binding of labeled antibodies is measured using radioactive or enzyme labels.

Production of Neutralizing Antibodies

Once antibodies with the desired neutralizing properties are identified, such antibodies, including antibody fragments can be produced by methods well known in the art, including, for example, hybridoma techniques or recombinant DNA technology.

In the hybridoma method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these cell lines, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (19.84); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Recombinant monoclonal antibodies can, for example, be produced by isolating the DNA encoding the required antibody chains and co-transfecting a recombinant host cell with the coding sequences for co-expression, using well known recombinant expression vectors. Recombinant host cells can be prokaryotic and eukaryotic cells, such as those described above.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.* 151:2296 (1993); Chothia et al., *J. Mol. Biol.* 196:901 (1987)). It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences.

In addition, human antibodies can be generated following methods known in the art. For example, transgenic animals (e.g., mice) can be made that are capable, upon immunization, of producing a full repertoire of human antibodies in the absence of endogenous immunoglobulin production. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669, 5,589,369 and 5,545,807.

Neutralizing Antibodies

A number of neutralizing antibodies have been identified through the use of the techniques described herein, including those described in the Example below. In one aspect, the present invention provides neutralizing antibodies that bind to a hemagglutinin protein epitope. In one embodiment, the neutralizing antibody binds to at least one epitope on the HA1 subunit of the hemagglutinin protein. In another embodiment, the neutralizing antibody binds to at least two, at least three, at least four, at least five, or at least six epitopes on the HA1 subunit of the hemagglutinin protein.

In some embodiments, the antibodies of the present invention neutralize viruses containing H3 and/or H1. In other embodiments, the antibodies neutralize both H3 and H1. In one embodiment, the antibodies of the present invention prevent hemagglutination. In other embodiments, the antibodies prevent the binding of an influenza A virus to a target cell to be infected. In another embodiment, the anti-hemagglutinin antibody prevents the receptor binding site on the globular head region of the HA of an influenza A virus from attaching to a target cell to allow hemagglutinin activity of HA to occur.

Based on the experiments described in the Examples below, a number of anti-hemagglutinin antibody heavy chain/light chain pairings were identified. In another embodiment, the antibodies of the present invention are cross-reactive to two or more influenza A virus subtypes. In one embodiment, the antibody contains a heavy chain polypeptide containing an amino acid sequence shown as SEQ ID NO:1 or SEQ ID NO:2 and a light chain polypeptide containing an amino acid sequence shown as SEQ ID NO:3, SEQ ID NO:4, SEQ ID NO:5, or SEQ ID NO:6. In a preferred embodiment, the neutralizing antibody of the present invention binds to an epitope that is substantially the same as the epitope for (i) an antibody comprising a heavy chain amino acid sequence shown as SEQ ID NO:2 and a light chain amino acid sequence shown as SEQ ID NO:6 (clone 1286-A11 in the Example below and as shown in Table 1); (ii) an antibody comprising a heavy chain amino acid sequence shown as SEQ ID NO:1 and a light chain amino acid sequence shown as SEQ ID NO:3 (clone 1286-C5 in the Example below and as shown in Table 1); (iii) an antibody comprising a heavy chain amino acid sequence shown as SEQ ID NO:1 and a light chain amino acid sequence shown as SEQ ID NO:4 (clone 1286-C5 in the Example below and as shown in Table 1); or (iv) an antibody comprising a heavy chain amino acid sequence shown as SEQ ID NO:1 and a light chain amino acid sequence shown as SEQ ID NO:5 (clone 1286-C5 in the Example below and as shown in Table 1).

TABLE 1

| Heavy Chain Sequence | SEQ ID NO | Light Chain Sequence | SEQ ID NO |
|---|---|---|---|
| QVQLQESGGGLVQPGESL RLSCVGSGSSFGESTLSYY AVSWVRQAPGKGLEWLSI | 1 | QSVLTQPPSVSGAPGQRVTISC TGSSSNIGAGYDVHWYQQLP GTAPKLLIYDNNNRPSGVPDR | 3 |

TABLE 1 -continued

| Heavy Chain Sequence | SEQ ID NO | Light Chain Sequence | SEQ ID NO |
|---|---|---|---|
| INAGGGDIDYADSVEGRF TISRDNSKETLYLQMTNL RVEDTGVYYCAKHMSMQ QVVSAGWERADLVGDAF DVWGQGTMVTVSS | | FSGSKSGASASLAITGLQAEDE AHYYCQSYDNSLSGSVFGGGT QLTVLS | |
| | | DIQLTQSPSSLSASVGDRVTLT CQASQDIRKFLNWYQQKPGK GPKLLIYDASNLQRGVPSRFSG GGSGTDFTLIISSLQPEDVGTY YCQQYDGLPFTFGGGTKLEIK | 4 |
| | | DIQLTQSPSSLSASIGDRVTITC QASQDIRNSLNWYEHKPGKAP KLLIHDASNLETGVPSRFSGGG SGTDFTLTISSLQPEDFATYYC QQANSFPLTFGGGTKVEIK | 5 |
| QVQLQQSGPRLVKPSQTL SLTCAISGDSVSGDSGTW NWIRQSPSRGLEWLGRTY YRSKWYNDYAESVKSRIV IKADTSKNEFSLQLNSVTP EDTAIYYCARAGVKIFGLI VGALDNWGRGTLVTVSS | 2 | EIVMTQSPGTLSLSPGERATLS CRASQSVSSSYLAWYQQKPG QAPRLLIYGASTRATGVPDRF HGGGSGTDFTLTISRLEPEDFA VYYCQQYDTSSGLTFGGGTK VEIK | 6 |

Antibodies with longer than typical heavy chain loops have been reported as demonstrating certain properties. For instance, a longer than typical heavy chain CDR3 loop has been linked to polyreactivity (Schettino et al. J. Immunol. 1997; 158; 2477-2489), and more recently they have been connected with numerous anti-HIV antibodies (Saphire et al. Science 2001; 293; 1151-1159; Kunert et al. AIDS Res. Hum. Retroviruses; 1998; 14(13); 1115-1128; Barbas et al. J Mol Biol 1993; 230(3):812-823) and anti-Pneumococcal antibodies (Baxendale et al. 2008; Clin. Exper. Immunol. 2007; 151; 51-60). An extended loop may facilitate deeper probing and interactions with pathogenic antigens. In the case of an HIV antibody, which contains a 19 amino acid length heavy chain CDR3, the target is engaged very specifically through the formation of a finger-like projection that contacts susceptible recessed regions on gp120. As described in Example 7, the C05 antibody heavy chain sequence has a remarkably atypical length heavy chain CDR1 loop of 11 amino acids and CDR3 loop of 25 amino acids.

In one aspect, the present invention relates to an influenza neutralizing antibody or binding molecule having a length-modified heavy chain CDR loop. Normally, the length of human heavy chain CDR1 loop that contacts antigen is typically either about 6 or 8 amino acids and the typical length of a human heavy chain CDR3 loop that contacts antigen is about 13 amino acids (Kabat et al., *Sequences of Proteins of Immunological Interest*, National Institutes of Health, Bethesda, Md., ed. 5, (1991)); MacCallum et al. 1996, J. Mol. Biol. 262, 732-745). In one embodiment, the length modified heavy chain is an "extended" heavy chain CDR loop, which refers to a CDR loop that is longer than the typical heavy chain CDR loop of an antibody.

In one embodiment, the antibody or binding molecule has an extended heavy chain CDR3 loop and/or an extended heavy chain CDR1 loop. In one embodiment, the extended heavy chain CDR3 loop is about 1 amino acid, about 2 amino acids, about 3 amino acids, about 4 amino acids, about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 amino acids longer than a typical heavy chain CDR3 loop. In another embodiment, the extended heavy chain CDR3 loop is about 1 to about 20 amino acid, about 1 to about 19 amino acids, about 1 to about 18 amino acids, about 1 to about 17 amino acids, about 1 to about 16 amino acids, about 1 to about 15 amino acids, about 1 to about 14 amino acids, about 1 to about 13 amino acids, about 1 to about 12 amino acids, about 1 to about 11 amino acids, about 1 to about 10 amino acids, about 1 to about 9 amino acids, about 1 to about 8 amino acids, about 1 to about 7 amino acids, about 1 to about 6 amino acids, about 1 to about 5 amino acids, about 1 to about 4 amino acids, about 1 about 3 amino acids, or about 1 to about 2 amino acids longer than a typical heavy chain CDR3 loop. In yet another embodiment, the extended heavy chain CDR3 loop is about 14, about 15, about 16, about 17, about 18, about 19, about 20, about 21, about 22, about 23, about 24, about 25, about 26, about 27, about 28, about 29, about 30, about 31, about 32, about 33, about 34, or about 35 amino acids long.

In a preferred embodiment, the extended heavy chain CDR3 loop is about 25 amino acids long. In another preferred embodiment, the extended heavy chain CDR3 loop comprises the amino acid sequence AKHMSMQQV-VSAGWERADLVGDAFD (SEQ ID NO:9). As the antibodies described are capable of inhibiting hemagglutination, it is possible that this long heavy chain CDR3 loop also forms a projection that probes deeply into the globular head. Such a deep probe of the globular head may provide a novel means of interfering with sialic acid coordination in the recesses of the globular head domain of hemagglutinin. This may contribute to the remarkable breadth of activity observed for antibodies having an extended CDR3 loop, as described herein.

In one embodiment, the antibody or binding molecule has an extended heavy chain CDR1 loop. In one embodiment, the extended heavy chain CDR1 loop is about 1 amino acid, about 2 amino acids, about 3 amino acids, about 4 amino acids, about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, or about 15 amino acids longer than a typical heavy chain CDR1 loop. In another embodiment, the extended heavy chain CDR1 loop is about 1 to about 15 amino acids, about 1 to about 14 amino acids, about 1 to about 13 amino acids, about 1 to about 12 amino acids, about 1 to about 11 amino acids, about 1 to about 10 amino acids, about 1 to about 9 amino acids, about 1 to about 8 amino acids, about 1 to about 7 amino acids, about 1 to about 6 amino acids, about 1 to about 5 amino acids, about 1 to about 4 amino acids, about 1 about 3 amino acids, or about 1 to about 2 amino acids longer than a typical heavy chain CDR1 loop. In yet another embodiment, the extended heavy chain CDR3 loop is about 3, about 4, about 5, about 6, about 7, about 8, about 9, about 10, about 11, about 12, about 13, about 14, or about 15 amino acids long.

In a preferred embodiment, the extended heavy chain CDR1 loop is about 11 amino acids long. In another preferred embodiment, the extended heavy chain CDR1 loop comprises the amino acid sequence GESTLSYYAVS (SEQ ID NO:7). As the heavy chain CDR1 region placement is typically proximal to CDR3 and towards the edge of the binding face, it is possible that the additional length (e.g., 3-5 amino acids) may impart additional physical docking surface area creating greater stability for the antibody to the hemaggluttinin. Curiously, analyses of the VH gene does not reveal the use of such an extended length of CDR1. Similarly, BLAST searches were unsuccessful at identifying any previously reported antibodies with such a CDR1 length. It bears consideration that positive selection played a role in reinforcing such a novel CDR1 length and composition.

In one other aspect, the length-modified heavy chain loop is a shortened heavy chain loop. The shortened heavy chain loop may comprise a deletion. In one embodiment, the CDR1 loop and/or the CDR3 loop comprise a deletion. In another embodiment, SEQ ID NO: 7 and/or SEQ ID NO:9 comprise a deletion. In one embodiment, the deletion within the heavy chain CDR1 or CDR3 loop is about 1 amino acid, about 2 amino acids, about 3 amino acids, about 4 amino acids, about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, or about 15 amino acids, or about 16 amino acids, or about 16 amino acids, or about 17 amino acids, or about 18 amino acids, or about 19 amino acids, or about 20 amino acids, or about 21 amino acids, or about 22 amino acids, or about 23 amino acids, or about 24 amino acids.

In one aspect, the present invention relates to an influenza neutralizing antibody or binding molecule having reduced oxidative potential or decreased oxidative heterogeneity potential. The oxidation of methionine by peroxides in aqueous formulations of polypeptides is considered to be detrimental to the development of protein-based therapeutics. The concern is at least two-fold. First, if the methionines are essential then oxidation must be controlled so that the antibody can maintain activity. However, if they are not essential for activity then non-oxidizable substitutions are preferred in order to produce antibodies or binding molecules with decreased heterogeneity. In one embodiment, the antibodies or binding molecules with reduced oxidative potential have a variant heavy chain amino acid sequence. In another embodiment, the variant amino acid sequence is in the CDR3 loop. In one embodiment, the variant amino acid sequence includes at least one substitution corresponding to an amino acid at position 96 and/or 98 according to Kabat numbering convention. In a preferred embodiment, a methionine at position 96 and/or 98 is the substituted amino acid. In yet another embodiment, the variant heavy chain amino acid sequence contains at least one substitution of a methionine residue. In one embodiment, the variant heavy chain amino acid sequence contains at least two substitutions of methionine residues. In a preferred embodiment, the variant sequence contains at least one methionine to leucine substitution, more preferably at least two methionine to leucine substitutions. In another embodiment, the variant sequence comprises one of the following:

```
                                    (SEQ ID NO: 25)
AKHMSLQQVVSAGWERADLVGDAFD;

(SEQ ID NO: 26)
AKHLSMQQVVSAGWERADLVGDAFD;

(SEQ ID NO: 27)
AKHASLQQVVSAGWERADLVGDAFD;
and (SEQ ID NO: 28)
AKHSSLQQVVSAGWERADLVGDAFD, preferably
                                    (SEQ ID NO: 29)
AKHLSLQQVVSAGWERADLVGDAFD.
```

In one embodiment, the antibody or binding molecule with decreased oxidative heterogeneity potential retains one or more of the following features: (i) neutralizes more than one subtype and/or more than one isolate of an influenza A virus, (ii) binds to a hemagglutinin (HA) antigen of the virus, (iii) inhibits hemagglutination, or any combination thereof.

In one aspect, the present invention concerns neutralizing antibodies or binding molecules with a polypeptide that comprises, consists essentially of, or consists of one or more the amino acid sequences shown as SEQ ID NOS: 1-29.

In another aspect, the present invention concerns a neutralizing antibody or binding molecule having a combination of heavy or light chain amino acid sequences described herein. For example, the heavy and light chain amino acid sequences for the 1286-C05 and 1286-A11 antibodies have been characterized (Example 2) and the present invention contemplates combinations as between their various heavy and light chains, CDR regions thereof, and/or functionally active fragments thereof. Antibodies or binding molecules described herein may be composed of the heavy and light chains and/or heavy and light chain hypervariable CDR regions (SEQ ID NOS:1-29) in any combination. In one embodiment, the antibody or binding molecule comprises a heavy chain SEQ ID NO:1 or 2 and a light chain SEQ ID NO:6; or a heavy chain SEQ ID NO:1 or 2 and one or more of light chains SEQ ID NOS:3, 4, or 5. In another embodiment, the antibody or binding molecule comprises (i) a heavy chain SEQ ID NO:1 and one or more of heavy chain hypervariable CDR regions SEQ ID NOS:10-12; (ii) a heavy chain SEQ ID NO:2 and one or more of heavy chain hypervariable CDR regions SEQ ID NOS:7-9; (iii) one of light chain SEQ ID NOS: 13-21 and one or more of heavy chain hypervariable CDR regions SEQ ID NOS:10-12; and (iv) one of light chain SEQ ID NOS:22-24 and one or more of heavy chain hypervariable CDR regions SEQ ID NOS: 7-9. In other embodiments, the antibody or binding molecule comprises (i) one or more of heavy chain hypervariable CDR regions SEQ ID NOS:7, 8, or 9 and one or more of heavy chain hypervariable CDR regions SEQ ID NOS:10, 11, or 12; (ii) one or more of heavy chain hypervariable CDR regions SEQ ID NOS:7, 8, or 9 and one or more of light chain hypervariable CDR regions SEQ ID NOS:22, 23, or 24; and (iii) one or more of heavy chain hypervariable CDR regions SEQ ID NOS:10, 11, or 12 and one or more of light chain hypervariable CDR region SEQ ID NOS:13-21. Those of ordinary skill in the art will appreciate other combinations of SEQ ID NOS:1-29, or functionally active fragments thereof.

Use of Neutralizing Antibodies

The influenza neutralizing antibodies of the present invention can be used for the prevention and/or treatment of influenza type A infections and for the development of vaccines presenting the appropriate cross neutralizing epitopes. For therapeutic applications, the antibodies or other molecules, the delivery of which is facilitated by using the antibodies or antibody-based transport sequences, are usually used in the form of pharmaceutical compositions. Techniques and formulations generally may be found in *Remington's Pharmaceutical Sciences,* 18th Edition, Mack Publishing Co. (Easton, Pa. 1990). See also, Wang and Hanson "Parenteral Formulations of Proteins and Peptides: Stability and Stabilizers," *Journal of Parenteral Science and Technology*, Technical Report No. 10, Supp. 42-2S (1988).

In one aspect, the present invention concerns a method of treating or preventing influenza in a subject in need. In one embodiment, the method includes the step of administering an influenza neutralizing antibody described herein to a subject in need. The antibody may be the C05 antibody. As described in Example 6, the C05 antibody may provide a therapeutic or prophylactic effect against influenza infection, e.g., an H3N2 infection.

Antibodies are typically formulated in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

The neutralizing antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257:286-288 (1982) via a disulfide interchange reaction. A chemotherapeutic agent is optionally contained within the liposome. See Gabizon et al. *J. National Cancer Inst.* 81(19)1484 (1989).

For the prevention or treatment of disease, the appropriate dosage of antibody will depend on the type of infection to be treated the severity and course of the disease, and whether the antibody is administered for preventive or therapeutic purposes. The antibody is suitably administered to the patient at one time or over a series of treatments. Depending on the type and severity of the disease, about 1 µg/kg to about 15 mg/kg of antibody is a typical initial candidate dosage for administration to the patient, whether, for example, by one or more separate administrations, or by continuous infusion.

The neutralizing antibodies of the present invention can be additionally used as a tool for epitope mapping of antigenic determinants of an influenza A virus, and are useful in vaccine development. Indeed, as shown in the Example below, the inventors herein have identified several broadly reactive neutralizing antibodies that can be used as guides for vaccine design.

Thus, the neutralizing antibodies of the present invention can be used to select peptides or polypeptides that functionally mimic the neutralization epitopes to which the antibodies bind, which, in turn, can be developed into vaccines against influenza A virus infection. In one embodiment, the present invention provides a vaccine effective against an influenza A virus comprising a peptide or polypeptide that functionally mimics a neutralization epitope bound by an antibody described herein. In one embodiment, the vaccine comprises a peptide or polypeptide functionally mimicking a neutralization epitope bound by an antibody that binds a hemagglutinin (HA) antigen. In another embodiment, the vaccine may be synthetic. In other embodiments, the vaccine may comprise (i) an attenuated influenza A virus, or a part thereof; or (ii) a killed influenza A virus, or part thereof. In one other embodiment, the vaccine comprises a peptide or polypeptide functionally mimicking a neutralization epitope bound by an antibody that binds a hemagglutinin (HA) antigen. The HA antigen may be an H3 subtype or an H1 subtype. In another embodiment, the HA antigen is displayed on the surface of an influenza A virus.

In another embodiment, the peptides or polypeptides of the vaccine contain antigenic determinants that raise cross-reactive influenza A virus neutralizing antibodies.

In one aspect, the present invention provides the use of antibodies described herein for the preparation of a medicament or pharmaceutical composition useful in or for the prevention or treatment of a disease in a subject in need. In another embodiment, the present invention provides pharmaceutical compositions for treating or preventing a disease in a subject in need, said composition comprising an influenza neutralizing antibody described herein.

Non-Antibody Molecules with Neutralizing Properties

Although in the previous description the invention is illustrated with reference to antibody libraries, libraries of other, non-antibody molecules, such as surrobodies, can be prepared, used, and optimized in a similar manner. Thus, the construction of unique combinatorial protein libraries based on the pre-B cell receptor (pre-BCR) ("surrobody libraries") are described in Xu et al., 2008, supra. As discussed before, the pre-BCR is a protein that is produced during normal development of the antibody repertoire. Unlike that of canonical antibodies, the pre-BCR subunit is a trimer that is composed of an antibody heavy chain paired with two surrogate light chain (SLC) components. Combinatorial libraries based on these pre-BCR proteins in which diverse heavy chains are paired with a fixed SLC were expressed in mammalian, *Escherichia coli*, and phagemid systems. These libraries contain members that have nanomolar affinity for a target antigen. A description of the library construction, selective enrichment, and biophysical characterization of library members is detailed in the Materials and Methods section of Xu et al., (2008), supra. Any of the antibody sequences described herein may be used to construct such binding or non-antibody molecules, such as for example surrobodies.

Further details of the invention are illustrated by the following non-limiting Examples.

Example 1—Antibody Libraries from Influenza Donors

Donors selected for inclusion into the Comprehensive Influenza Library were confirmed to have had a previous influenza infection, been approximately 5 years old at the time of a the 1957 H2N2 or 1968 H3N2 influenza pandemics, and to be in current good health. Serology on a panel of H1N1 A/NewCaledonia/20/99, H3N2 A/Panama/2007/99 and H5N1 A/Vietnam/1203/2004 virus or hemagglutinin proteins was performed to confirm the presence of antibodies to the hemagglutinin proteins.

First 5-20 ml of bone marrow was collected from each donor meeting the selection criteria and mixed with RNAlater (Applied Biosystems) per the manufacture's instructions to preserve the integrity of cellular RNA. RNA was isolated using a TRI-BD reagent protocol (Sigma-Aldrich).

Heavy chain and light chain repertoires were recovered from each donor derived RNA by RT-PCR using random primed cDNA template for heavy chains, oligo dT primed cDNA template for light chains and gene specific variable domain primers.

Next, 1 ug each of pooled Kappa light chain and pooled Lambda light chain per donor are digested with NotI and BamHI and gel purified using Qiagen Gel Extraction Kit. For kappa and lambda light chain cloning 5 ug of each vector was digested with NotI and BamHI and gel purified using Qiagen Gel Extraction Kit. Light chain library ligations are performed with 200 ng of gel purified Kappa or Lambda inserts and 1 ug of gel purified vector. Incubation is overnight at 14° C. To determine cloning efficiencies, a control ligation reaction is set up equal to the amount of one electroporation (200-300 ng vector DNA) without the addition of light chain inserts. Prior to transformation the ligations are desalted using Edge BioSystem Perfroma spin columns. Each library was transformed in 3-5 electroporations using 80 µl Dh5α electrocompentent cell aliquots, with each recovered into 1 ml SOC, pooled and outgrown for one hour at 37 C. A sample of each library is plated on selective media and used to determine the efficiency of cloning and total number of transformants. The remainder is transferred to 200 ml 2YT+100 ug/ml Ampicillin+2% glucose and grown overnight at 37° C. Successful libraries have background of less than 10% and total transformants exceeding $1\times10^6$ members. The following day light chain library plasmids were isolated using a Qiagen High Speed Maxiprep Kit.

To clone heavy chain collections 1.5-2 ug each of the 5 donor specific heavy chains variable genes (VH1/7, VH 2, 5, 6, VH 3, and VH 4) are digested with a 40 Unit excess/ug DNA with SfiI and XhoI and gel purified using Qiagen Gel Extraction Kit. To prepare the recipient plasmid 15 ug of each light chain library vector is digested with a 40 Unit excess/ug DNA with SfiI and XhoI and gel purified using Qiagen Gel Extraction Kit. Library ligations are accomplished by combining 1.2 ug SfiI/XhoI digested, gel purified heavy chain DNA per donor pooled to contain 300 ng of each of the 5 heavy chain variable gene families with 5 ug of each light chain library, Kappa and Lambda respectively. A control ligation reaction is set up equal to the amount of one electroporation (300-600 ng vector DNA) without the addition of heavy chain inserts. The ligations were incubated overnight at 14° C. and then desalted with Edge BioSystem Pefroma spin columns. The ligation was transformed into 8-12 electroporations per library are done using 80 ul TG-1 cells, each recovered into 1 ml SOC, pooled and outgrown for one hour at 37° C. A sample of each was used to determine the efficiency of cloning and the total number of transformants. Target number of transformants/library should be at least $1\times10^7$ with a background of less than 10%. The remainder was transferred to 300 ml 2YT+100 ug/ml Ampicillin+2% glucose and grown to an OD600 of ~0.3. Next m13K07 helper phage was added at a multiplicity of infection (MOI) of 5:1 and incubated for 1 hour at 37° C. without shaking. Following helper infection, the cells were harvested by centrifugation and resuspended in 300 ml 2YT+100 ug/ml Ampicillin+2% glucose+70 ug/ml Kanamycin and growth continued at 37° C. overnight with shaking for stock phage production.

The resulting phage containing culture supernatents are harvested by centrifugation at 6000 RPM for 10 minutes at 4° C. Next the phage are precipitated by the addition of 0.2 volume of 20% PEG/2.5M NaCl solution to each supernatant and incubation on ice for 1 hour. Phage are then harvested by centrifugation at 7900 RPM for 15 minutes at 4 C. The supernatant is removed and the phage pellet resuspended in 30 ml sterile 1xPBS. For long term −20° C. storage the PBS is supplemented with 50% glycerol.

Example 2—Preparation of Neutralizing Antibodies

Antibodies derived from human bone marrow phage display antibody libraries (see Example 1) were converted and tested as mammalian expressed immunoglobulins, as previously described (see also, Kashyap A K et al., Proc Natl Acad Sci USA. 2008 Apr. 22; 105(16):5986-91). The heavy chains fell into two sequence classes:

```
                                              (SEQ ID NO: 1)
QVQLQESGGGLVQPGESLRLSCVGSGSSFGESTLSYYAVSWVRQAPGKGL

EWLSIINAGGGDIDYADSVEGRFTISRDNSKETLYLQMTNLRVEDTGVYY

CAKHMSMQQVVSAGWERADLVGDAFDVWGQGTMVTVSS (SEQ ID NO: 2)
QVQLQQSGPRLVKPSQTLSLTCAISGDSVSGDSGTWNWIRQSPSRGLEWL

GRTYYRSKWYNDYAESVKSRIVIKADTSKNEFSLQLNSVTPEDTAIYYCA

RAGVKIFGLIVGALDNWGRGTLVTVSS
```

The underlined hypervariable CDR regions are shown for the heavy chains as follows.

```
                                              (SEQ ID NO: 7)
        GESTLSYYAVS (SEQ ID NO: 8)
        WLSIINAGGGDID (SEQ ID NO: 9)
        AKHMSMQQVVSAGWERADLVGDAFD (SEQ ID NO: 10)
        SGDSGTWN (SEQ ID NO: 11)
        WLGRTYYRSKWYND (SEQ ID NO: 12)
        ARAGVKIFGLIVGALD
```

The heavy chain described by SEQ ID NO:1 was found to pair with one lambda light chain (SEQ ID NO:3) and two kappa light chains (SEQ ID NOS:4-5) exemplified by clone 1286-C5.

```
                                                (SEQ ID NO: 3)
QSVLTQPPSVSGAPGQRVTISCTGSSSNIGAGYDVHWYQQLPGTAPKLLI

YDNNNRPSGVPDRFSGSKSGASASLAITGLQAEDEAHYYCQSYDNSLSGS

VFGGGTQLTVLS (SEQ ID NO: 4)
DIQLTQSPSSLSASVGDRVTLTCQASQDIRKFLNWYQQKPGKGPKLLIYD

ASNLQRGVPSRFSGGGSGTDFTLIISSLQPEDVGTYYCQQYDGLPFTFGG

GTKLEIK (SEQ ID NO: 5)
DIQLTQSPSSLSASIGDRVTITCQASQDIRNSLNWYEHKPGKAPKLLIHD

ASNLETGVPSRFSGGGSGTDFTLTISSLQPEDFATYYCQQANSFPLTFGG

GTKVEIK
```

The underlined hypervariable CDR regions are shown for the light chains as follows.

```
            IGAGYDVHWY                          (SEQ ID NO: 13)

LLIYDNNNRP                          (SEQ ID NO: 14)

QSYDNSLSGS                          (SEQ ID NO: 15)

IRKFLNWY                            (SEQ ID NO: 16)

LLIYDASNLQ                          (SEQ ID NO: 17)

QQYDGLPF                            (SEQ ID NO: 18)

IRNSLNWY                            (SEQ ID NO: 19)

LLIHDASNLE                          (SEQ ID NO: 20)

QQANSFPL                            (SEQ ID NO: 21)
```

The heavy chain described by SEQ ID NO:2 and exemplified by clone 1286-A11 pairs with a single kappa light chain (SEQ ID NO:6).

```
                                                (SEQ ID NO: 6)
EIVMTQSPGTLSLSPGERATLSCRASQSVSSSYLAWYQQKPGQAPRLLIY

GASTRATGVPDRFHGGGSGTDFTLTISRLEPEDFAVYYCQQYDTSSGLTF

GGGTKVEIK
```

The underlined hypervariable CDR regions are shown for the light chain as follows.

```
            SSYLAWY                             (SEQ ID NO: 22)

LLIYGASTRA                          (SEQ ID NO: 23)

QQYDTSSGL                           (SEQ ID NO: 24)
```

Figure 4:
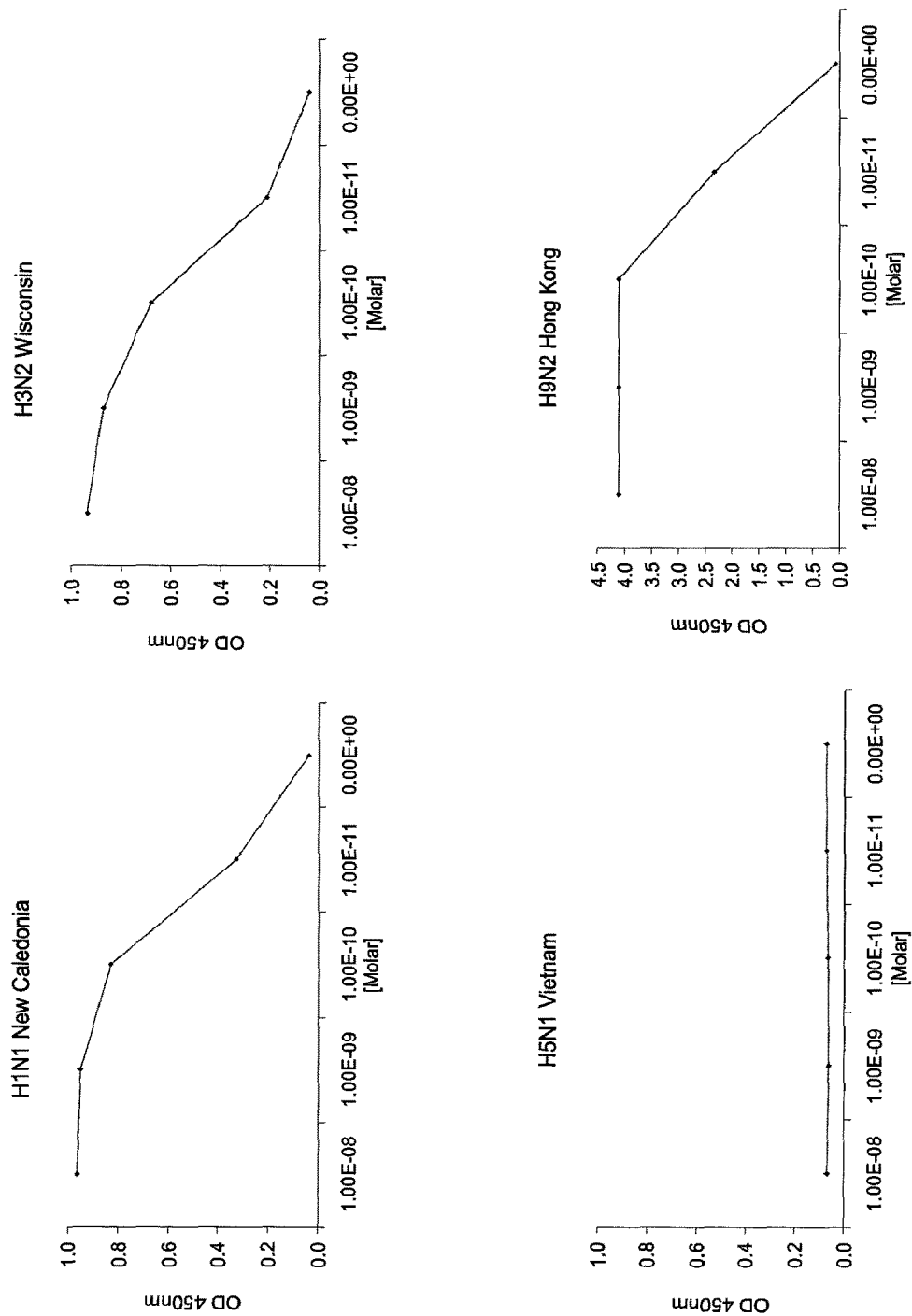
FIG. 4 shows the binding ability of the 1286-C5 antibody to hemagglutinin antigens from H1, H3, and H9.
Figure 5:
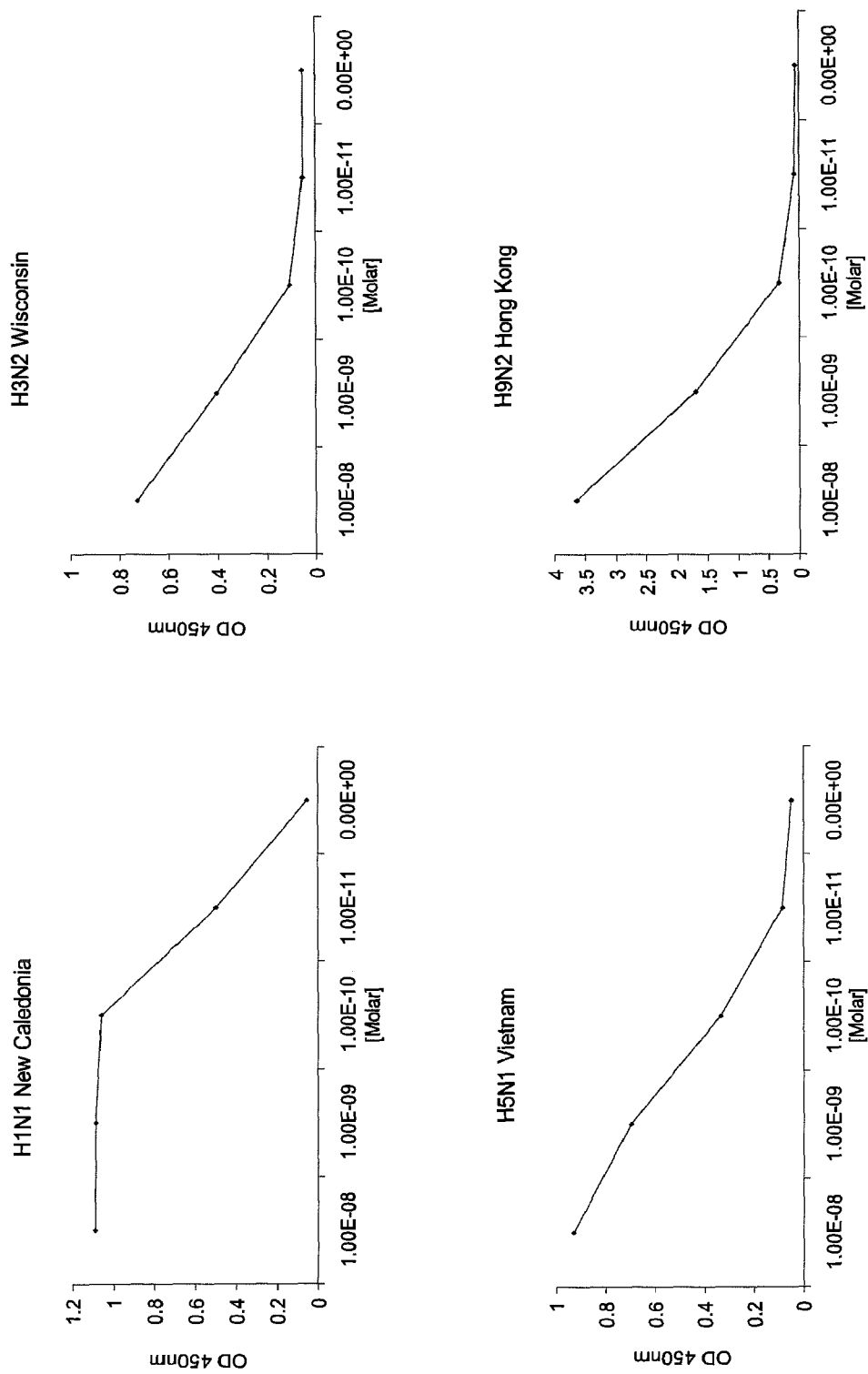
FIG. 5 shows the binding ability of the 1286-A11 antibody to hemagglutinin antigens from H1, H3, H5, and H9.

FIGS. 4-5 show the binding ability of the clone 1286-C5 antibody and the clone 1286-A11. To characterize the function of these antibodies, the corresponding IgGs were tested for the ability to bind on a panel of different antigens (FIGS. 4 and 5), as previously described (see also, Kashyap A K et al. 2008 supra). The binding ability of the clone 1286-A11 and 1286-C5 antibodies. Both 1286-A11 and 1286-C5 were capable of binding H1N1, H3N2 and H9N2 hemagglutinin. In addition, 1286-A11 was able to bind H5N1 hemagglutinin. Microneutralization of various influenza subtype viruses was also performed as previously described (see also, id.).

As shown in Table 2 below, each antibody was able to neutralize H1 virus replication in vitro in MDCK cells.

TABLE 2

| Sub-type | Strain | | Binding | Neutralization MIC (ug/mL) |
|---|---|---|---|---|
| 1286-C5 | | | | |
| Avian Influenza | H5N1 | Vietnam/1203/04 | No | No activity at 333 |
| | H9N2 | Hong Kong 1073/99 | Yes | 100 |
| Seasonal Influenza | H1N1 | New Caledonia/20/99 | Yes | 0.5 |
| | | Solomon Islands/3/06 | Yes | 0.65 |
| | H3N2 | Wisconsin/67/05 | Yes | 0.13 |
| | | Hong Kong/68 | Yes | 0.13 |
| "Asian" Influenza | H2N2 | Adachi/1/1957 | Yes | 21 |
| 1286-A11 | | | | |
| Avian Influenza | H5N1 | Vietnam/1203/04 | Yes | partial activity at 333 |
| Seasonal Influenza | H1N1 | New Caledonia/20/99 | Yes | 83 |
| | | Solomon Islands/3/06 | Yes | Not tested |
| | H3N2 | Wisconsin/67/05 | Yes | No activity at 333 |
| | | Hong Kong/68 | Yes | |

1286-C5 also showed the remarkable ability to neutralize H3 virus replication. 1286-A11 did not measurably neutralize an H3 sub-type virus, but did however display H5 sub-type neutralization. The mechanism of action of the 1286-C5 antibody is through hemagglutination inhibition, while the mechanism of action for 1286-A11 has not been determined.

Each of these antibodies would be optimized for increased potency and spectrum of activity through standard directed and randomized antibody optimization techniques, such as saturation mutagenesis and error-prone PCR, respectively. Presumably these antibodies would be useful if converted to various fragments, as well as monospecific and multispecific surrobodies.

Example 3—Generating Universal Influenza Vaccines

The goal of vaccine design against heterogeneous pathogens is to identify and design effective and broadly protective antigens. In the case of influenza, considerable historical efforts have gone into the empirical testing of conserved linear sequences and regions with little success. A plausible reason for these failures is a lack of knowledge that focused responses against antigenic test articles are actual bona fide productive sites for neutralization of an antigen on the pathogen in the setting of an actual infection. For influenza one would be expect to find these bona fide solutions within the repertoires of survivors of an influenza infection. In our case we have demonstrated that certain antibodies amongst a large collection of antibodies are capable of neutralizing multiple subtypes of Influenza. Some of these antibodies neutralize influenza through classical inhibition of hemagglutination. Collectively, we expect that the design and assessment of vaccines utilizing such cross neutralizing antibodies derived from bona fide survivors would aid in the design and validity of cross reactive or "universal" influenza vaccines.

Specifically cross neutralizing monoclonal antibodies can be used in the design and validation of vaccine production processes that maintain or enhance the quality and antigenicity of cross neutralizing epitopes in current and future manufactured vaccines. Assuming that antibody binding to vaccine is reflective of structural integrity and antigenic potential, one would assess binding of cross neutralizing antibodies to such vaccine process derivatives to quantitatively assess their cross neutralizing potential.

To maximize the responses toward these universal epitopes one would create derivatives to increase immunogenicity towards these universal epitopes through adjuvants, like a spore coat or spore exosporium. Alternatively one could engineer and optimize these cross neutralizing epitopes to increase their immunogenicity through predictive models and supportive testing. In any case the resulting antigen would again be tested to insure that not only the efficiency of binding to target was maintained, but that a directed immunogenicity was accomplished. This would either involve determining the specific universal neutralizing titers contained in the serum from immunized individuals or test animals, likely by competitive ELISA. As an in vitro surrogate, one would combine the antigen-antibody binding data with that of an in vitro or in silico predictive model for immunogenicity. To further direct responses to the universal epitope one may deimmunize known non-neutralizing and non-crossreactive hemagglutinin epitopes It reasonable to extend this antibody into the design and validation of engineered recombinant hemagglutinin chimeras, fragments, and conformational mimics. For instance, it is well established that influenza contains many immunodominant epitopes that give rise to non-neutralizing responses. Utilizing the cross protective antibodies it is possible to assess whether antigen variants of vaccines that have been partially or fully deimmunized for these immunodominant non-neutralizing epitopes have maintained or created enhanced recognition of the universally protective epitopes.

Also as a result of these vaccine designs, one could minimize the antigen epitopes and even remove them from the context of hemagglutinin to create a conformational cross specific antigen.

The strategies outlined above detail methods to guide a response to a minimized neutralizing epitope or element. From the knowledge of such minimized elements, which are likely be conformationally dependent and exist within discontinuous sequence space, it would be possible to recreate the conformational neutralizing epitope in a combinatorial fashion within a smaller polypeptide, as described previously (see Horowitz et al., Combinatorial Libraries of Conformationally Constrained Polypeptide Sequences, PCT Publication No. WO/2008/089073) where the proximal placement of discontinuous epitopes alone, or in the context of designed structural support, can regenerate the essential properties of conformational epitopes.

In such a design we would take the conformation epitope and express them on hemagglutinin related and unrelated structural scaffolds, or even as a collection of conformational epitopes within a library that could be selected by conformationally dependent antibodies.

The reduction of discontinuous epitopes to a conformational epitope would result in an even smaller sized peptide immunogen than that possible with traditional protein engineering. Furthermore these structural epitopes may be further enhanced, reduced in size, or substituted through the use of nonpeptide mimetics. In any event, any of these conformational derivatives or mimics would be validated by one or more of SEQ ID NOS:1-6, related antibodies comprising at least one of SEQ ID NOS:1-6, or a corresponding antibody to the influenza virus of choice.

Methods and materials. Crossreactive Influenza HAI epitope spore vaccine targets.
1. Mammalian expression of target as secreted protein or on mammalian cell.
   a. globular HA1 variant from a single isolate
   b. globular HA1 chimera from related isolates
   c. globular HA1 chimera from unrelated isolates
   d. globular HA1 chimera from related and unrelated isolates
2. Detect conformational epitope with SEQ ID NOS:1-6 antibodies or related antibodies of secreted protein or on mammalian cell
3. Transfer successful conformational antigen to spore expression
4. Test for spore binding with SEQ ID NOS:1-6 antibodies or -related antibodies
5. Assess crossreactive immunogenicity in vivo Example 4—Increasing the Potency and Spectrum of Cross Subtype Neutralizing Antibodies Based on the sequence information for the heavy and light chains of the antibodies described in Example 1, methods of mutagenesis are used to create improved mutants for testing either individually or amongst a collection in a library. Methods commonly used to introduce beneficial mutations could be saturation mutagenesis at sites responsible for binding or error-prone PCR mutagenesis throughout the regions known to be responsible for binding.

If crossreactivity and potency are insufficient because of inherent limitations of conventional antibody optimization strategies, one might consider destinational mutagenesis, amalgamated antibody libraries, or combinations of either or both of these methods with each other or with the previously mentioned conventional optimization strategies.

Example 5—Co-Administration of Vaccine and Antibody to Increase Potency and Spectrum of Protection Complexes of antibody and antigen are known to potently induce responses against numerous microbial proteins and other proteins in animals. One possible explanation is that a forced uptake of the vaccine antibody complex occurs by Fc receptors on antigen presenting cells. Complexes of cross reactive antibodies with seasonal vaccines would allow for increases in potency from year to year and because the cross-reactive antibodies recognize numerous hemagglutinin antigens, this obviates the need to recreate new antibodies when new viral isolates are selected for each seasons Influenza vaccine. Furthermore, as these antibodies are directed at conserved neutralizing regions they may actually direct a more effective protective response towards these critically conserved susceptible regions when complexed with antigen. As described previously, the vaccine may be a traditional live or killed virus, recombinant protein or protein fragment, or even minimized peptide or non-peptidic conformationally epitope complexed with an antibody, antibody fragment or derivative, or surrobody.

Example 6—Protective Effect Against Influenza Challenge

Female 6-8 weeks old DBA/2 (Charles River) mice were housed 5-6 per cage in ABSL3+ containment. Food and water were provided ad libitum. Mice (5-6 per group) received 1, 2.5, 10, or 25 mg antibody C05 (C05-1286) per kg of bodyweight in approximately 200-300 µL of sterile phosphate-buffered saline (PBS) by intraperitoneal (IP) injection. The control groups were injected with 200-300 µL of either 25 mg nonimmune human IgG in PBS or PBS alone via IP injection. Antibody and controls were administered 24 hours prior to viral challenge with X-31 (H3N2) or A/Memphis/3/2008 (H1N1) virus. For a lethal virus challenge, mice were inoculated by intranasal administration with 33 $MLD_{50}$ (50% mouse lethal dose) influenza virus in 30-50 µL of PBS. Both the H3N2 and H1N1 viruses are highly pathogenic in DBA/2 mice. Symptoms preceding death are weight loss >30% and general inactivity. Body weight, morbidity, and mortality were monitored daily for fourteen days.

Figure 7A:
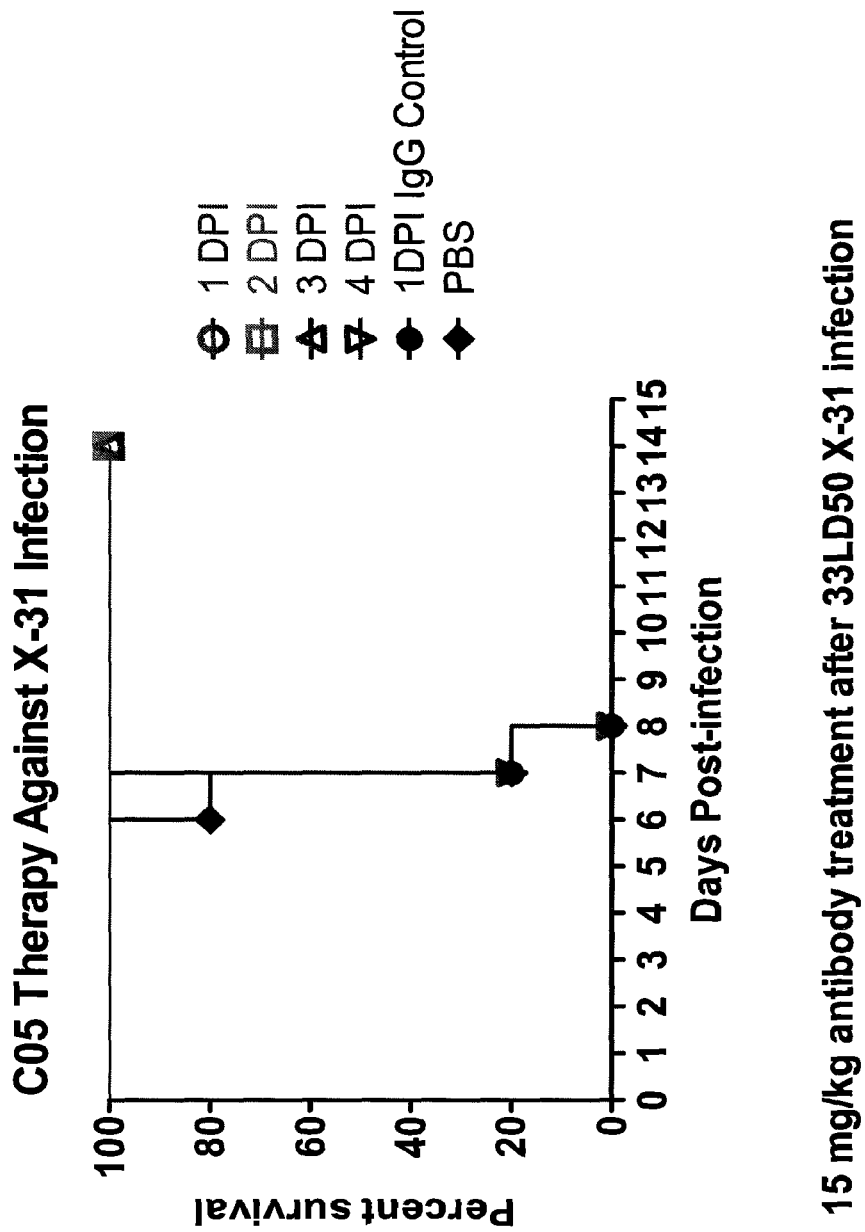
FIG. 7A-E illustrates the therapeutic and protective effect of an influenza neutralizing antibody.
Figure 7B:
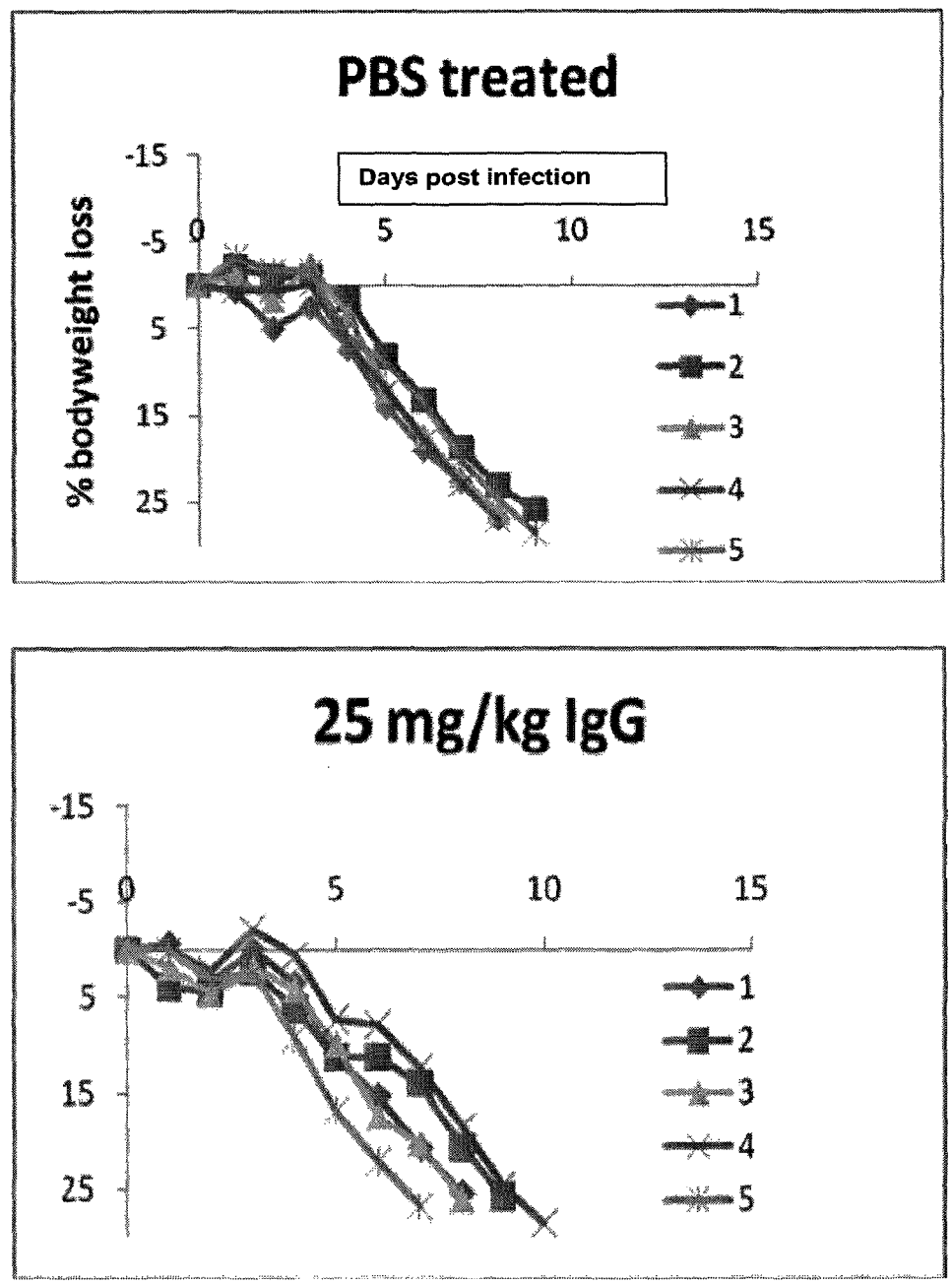
Figure 7B:
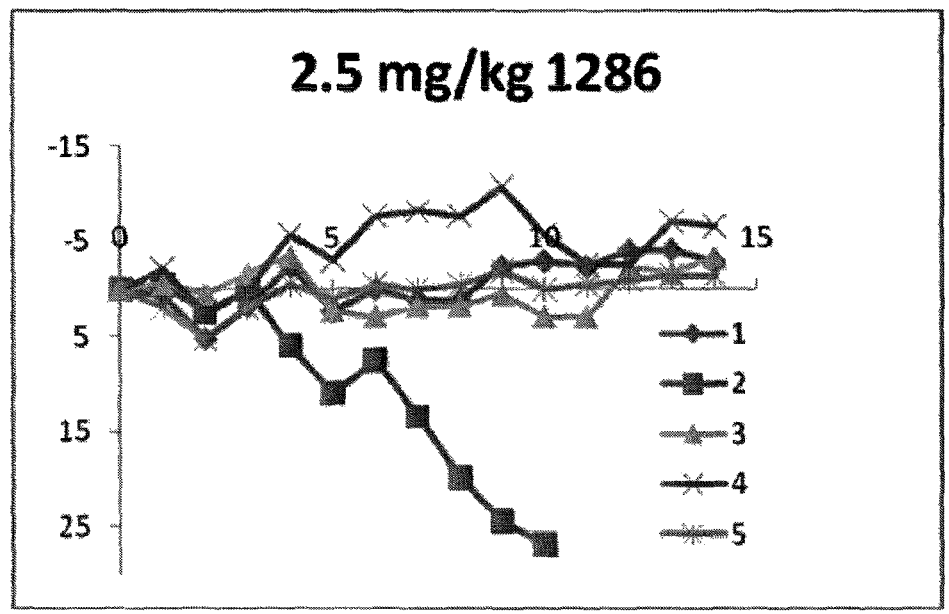
Figure 7B:
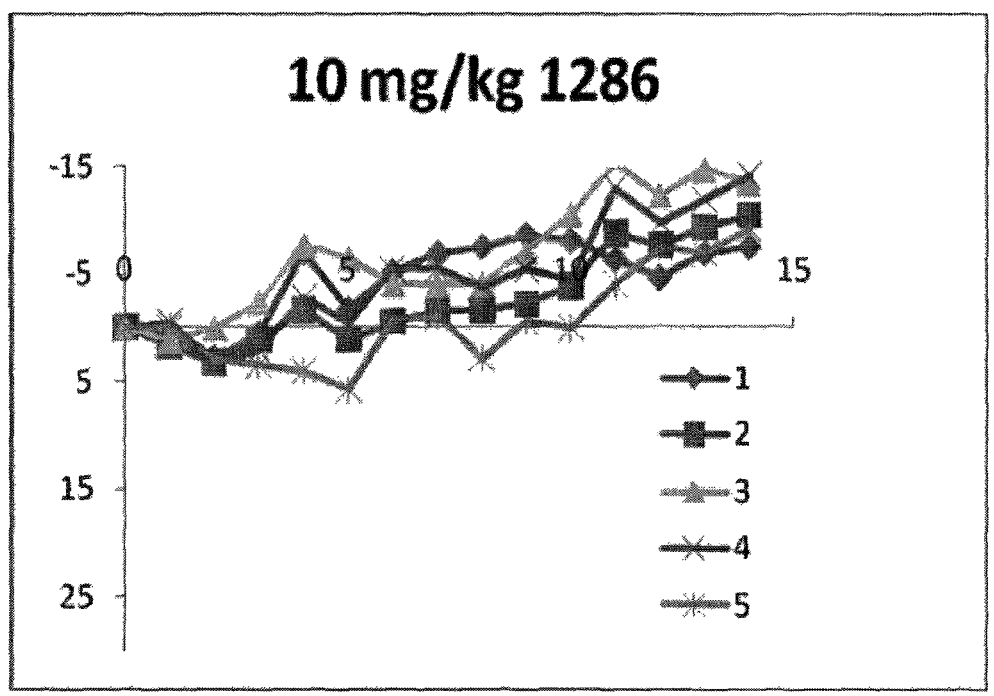
Figure 7B:
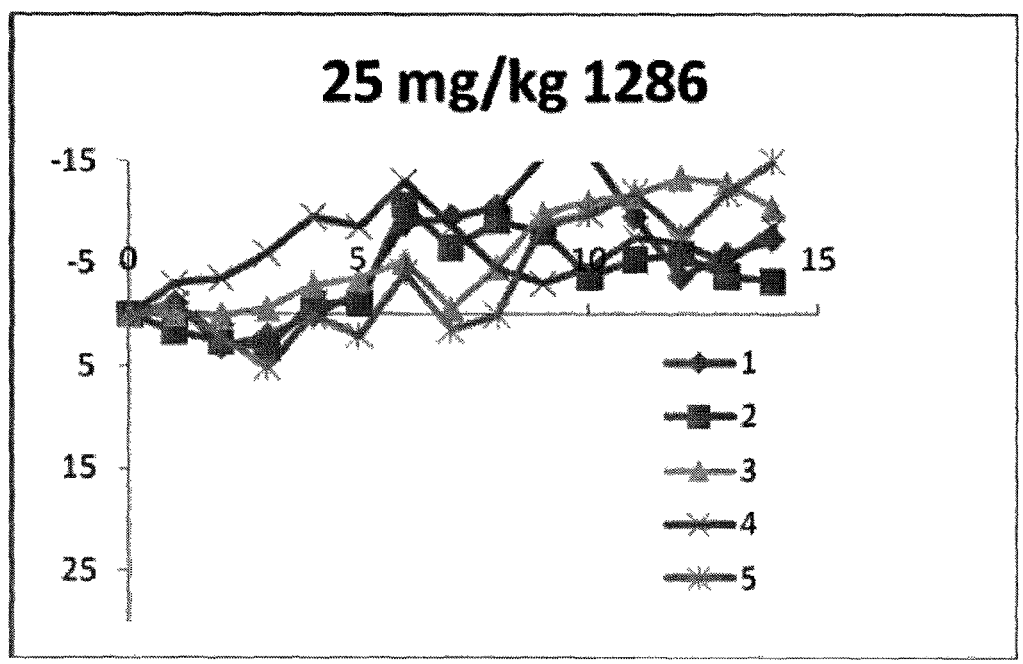

FIG. 7A-B illustrates the prophylactic effect of the C05 antibody against high titer lethal H3N2 viral challenge. For the high titer challenge (33 $MLD_{50}$), the following results were obtained. PBS treated: 0% survival. 2.5 mg/kg treated: 80% survival. 10 mg/kg treated: 100% survival. 25 mg/kg treated: 100% survival. 25 mg/kg IgG isotype: 0% survival. FIG. 7E illustrates the prophylactic effect of the C05 antibody against H1N1 Memphis/3/2008 viral challenge.

Figure 7C:
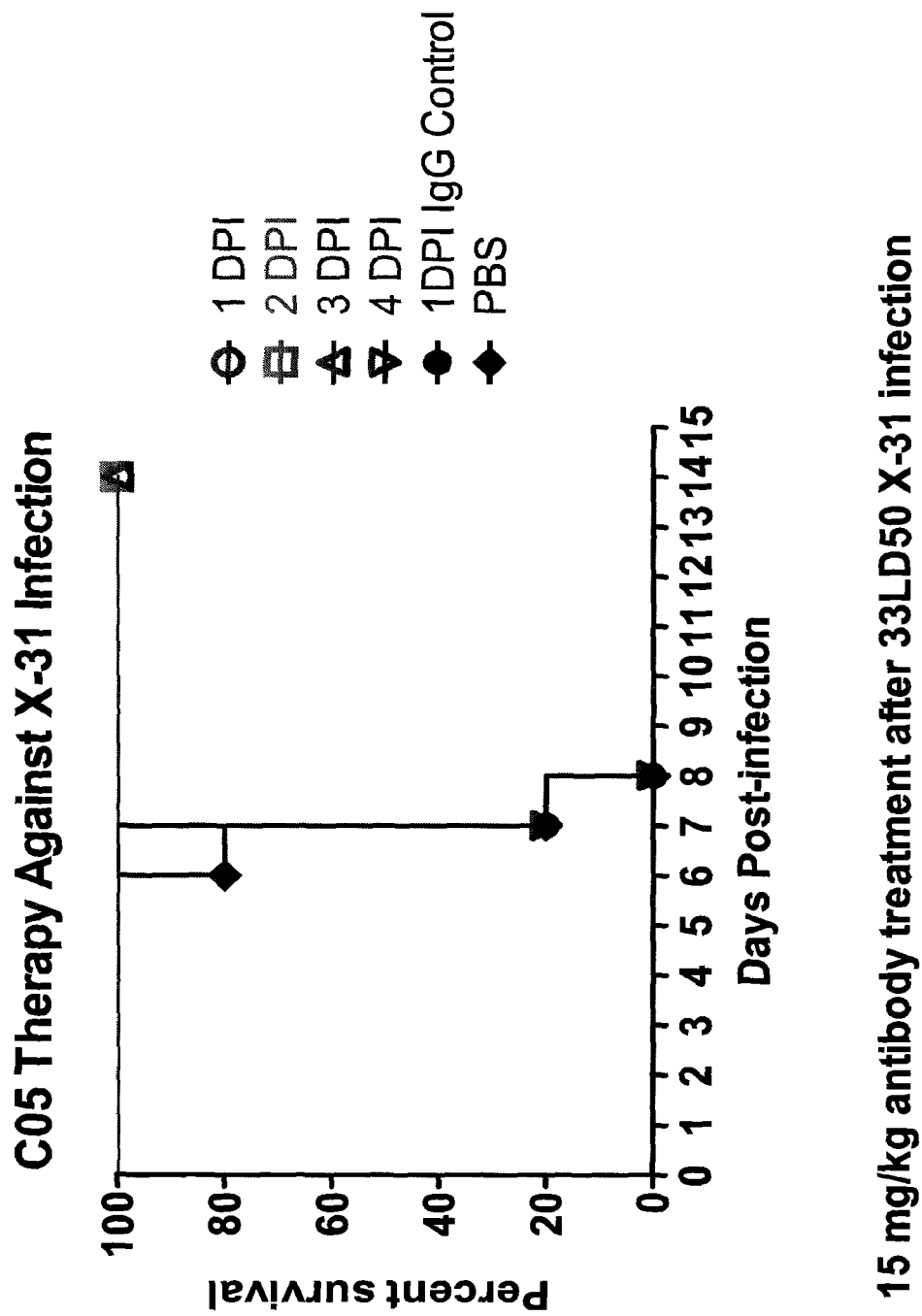
Figure 7D:
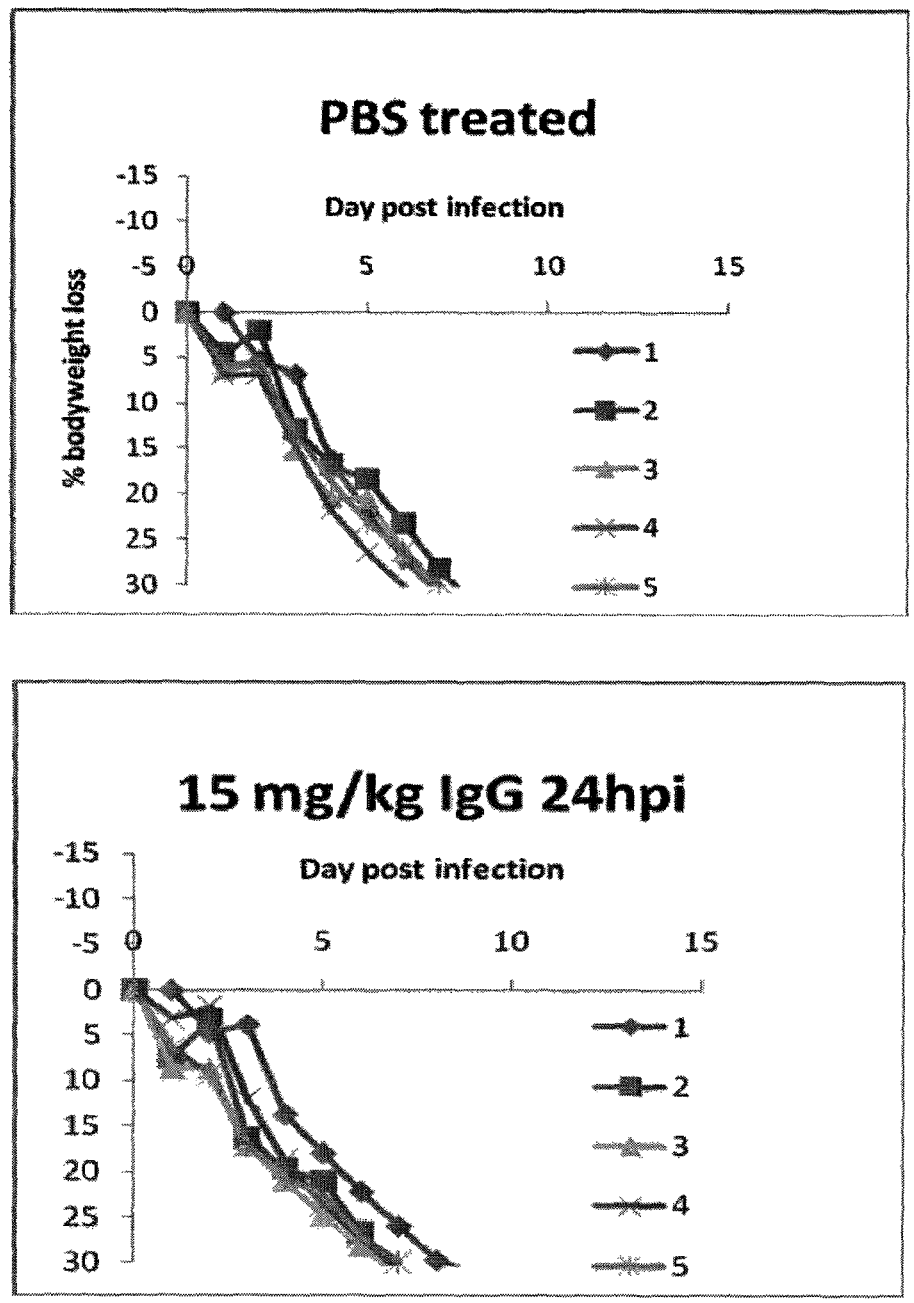
Figure 7D:
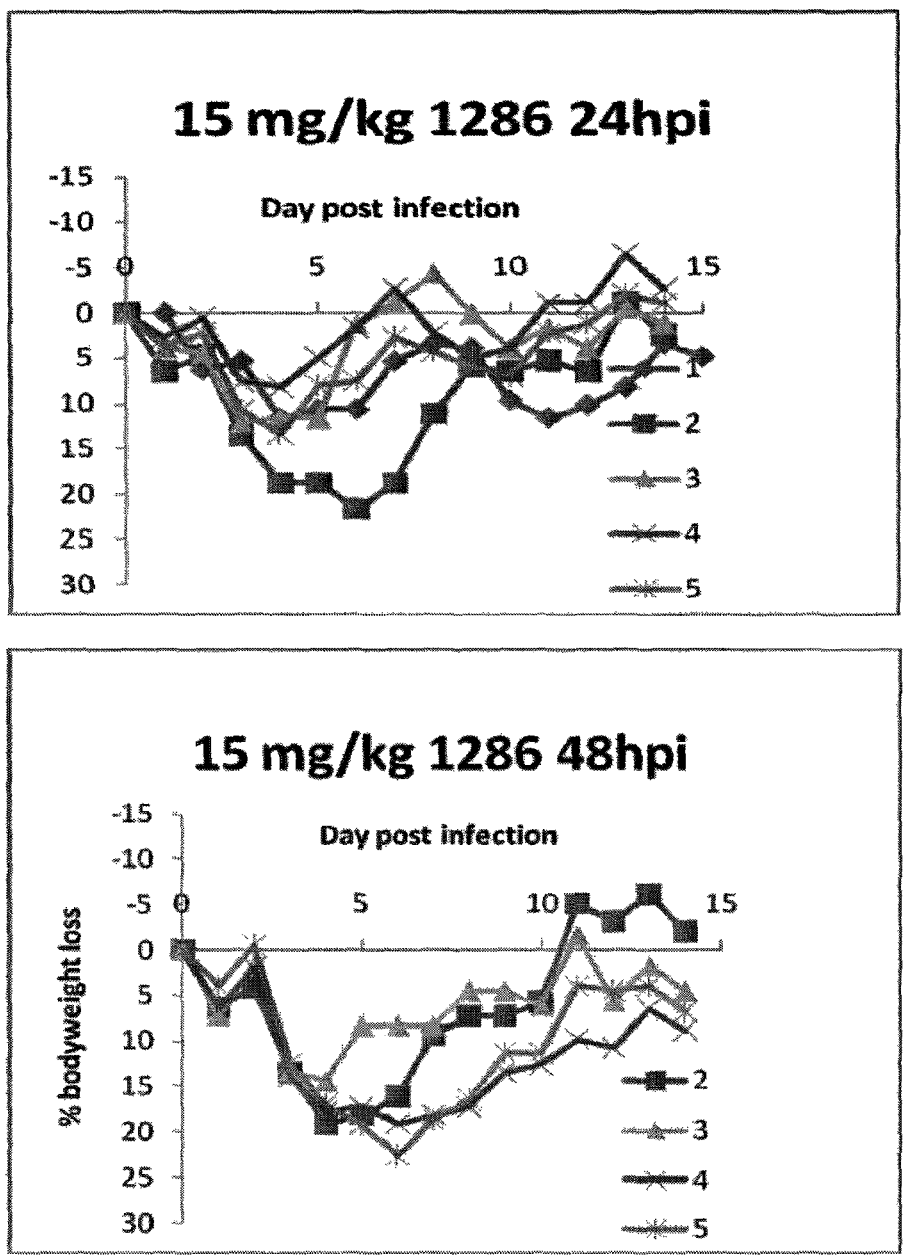
Figure 7D:
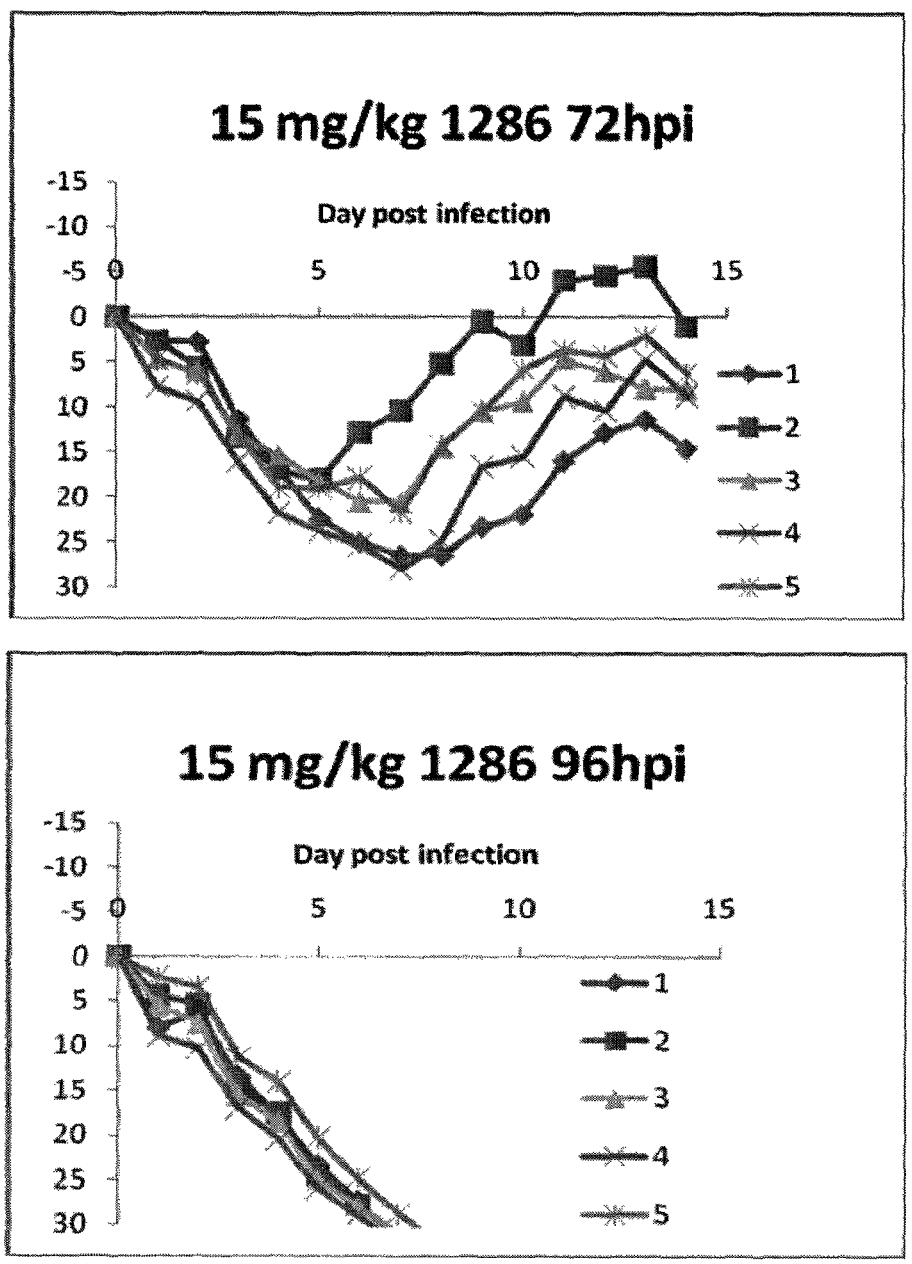
Figure 7E:
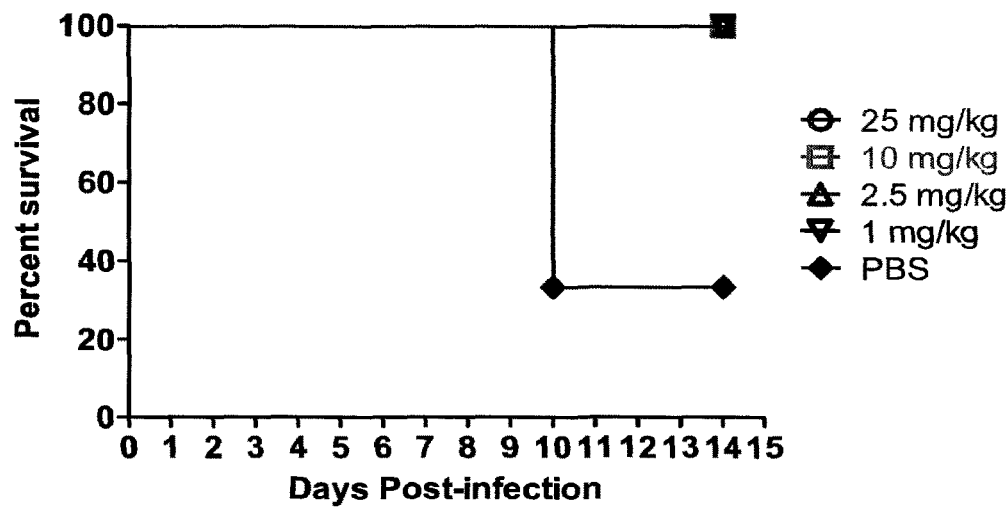
Figure 7E:
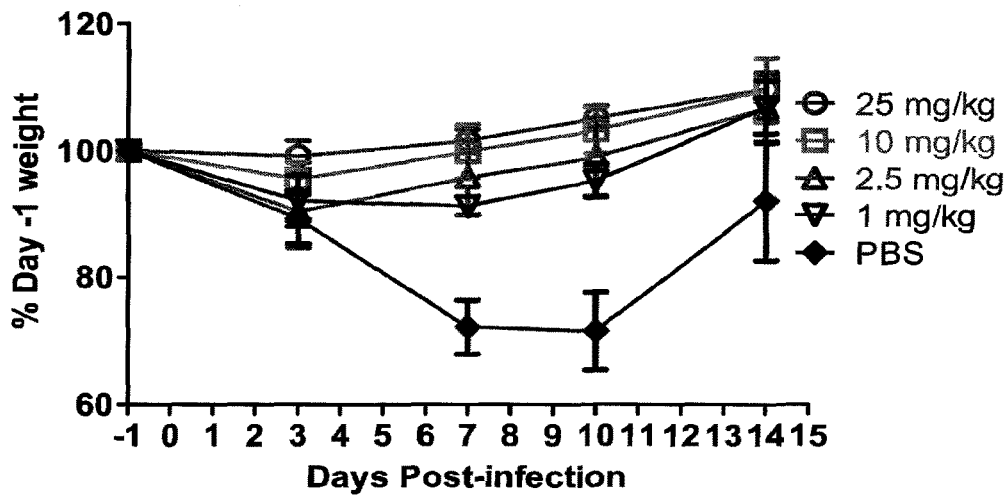

FIG. 7C-D show a therapeutic effect by the C05 antibody against lethal H3N2 viral challenge. DBA/2 mice were first inoculated by intranasal administration with 33 $MLD_{50}$ (50% mouse lethal dose) X-31 (H3N2) influenza virus in 30-50 µL of PBS. Mice (5-6 per group) received 15 mg antibody C05 (C05-1286) per kg of bodyweight in approximately 200-300 µL of sterile phosphate-buffered saline (PBS) by intraperitoneal (IP) injection. The control groups were injected with 200-300 µL of either 25 mg non-immune human IgG in PBS or PBS alone via IP injection. The C05 antibody was administered at 24, 48, 72, or 96 hours after infection. Administration of the controls occurred at 24 hours after infection. Body weight, morbidity, and mortality were monitored daily for fourteen days.

Example 7—Generating Variants with Heavy Chain Loops of Varied Lengths

As shown below, the C05 antibody heavy chain sequence (SEQ ID NO:1) has a remarkably atypical length heavy chain CDR1 (SEQ ID NO:7) loop of 11 amino acids. The C05 has 5 more amino acids at CDR1 compared to VH3-23 germline.

| | CDR1 | CDR2 |
|---|---|---|
| VH3 3-23 | EVQLLESGGGLVQPGGSLRLSCAASGFTF-----SSYAMSWVRQAPGKGLEWVSAISGSGGSTYYADSVKGRFTISRDNSKNTLYLQMNSLRAEDTAVYYCAK | |
| C05 | QVQLQESGGGLVQPGESLRLSCVGSGSSFGESTLSYYAVSWVRQAPGKGLEWLSIINAGGGDIDYADSVEGRFTISRDNSKETLYLQMTNLRVEDTGVYYCAK | |

| CDR1 Deletions | CDR1 Insertions |
|---|---|
| Progressive | CDR flanking |
| -----SSYAMS 3-23 germline | C05-based |
| GESTLSYYAVS C05 | GESTLSYYAVS |
| -ESTLSYYAVS | $(X)_m$GESTLSYYAVS |
| --STLSYYAVS | GESTLSYYAVS$(Y)_n$ |
| ---TLSYYAVS | $(X)_m$GESTLSYYAVS$(Y)_n$ |
| ----LSYYAVS | Germline based |
| -----SYYAVS | SSYAMS |
| | $(X)_m$SSYAMS |
| | SSYAS$(Y)_n$ |
| | $(X)_m$SSYAMS$(Y)_n$ |

As the heavy chain CDR1 region placement is typically proximal to CDR3 and towards the edge of the binding face, it is possible that the additional length 3-5 amino acids may impart additional physical docking surface area creating greater stability for the antibody to the hemagglutinin. Analysis of the VH gene repertoire does not reveal the use of such an extended length of CDR1. Furthermore, BLAST searches do not identify any antibodies with such a CDR1 length. It therefore bears consideration that positive selection may have played a role in the existence and reinforcement of such a novel CDR1 length and its composition. Because the heavy chain is marked by such unique loop lengths in both CDR1 and CDR3 that one would consider increasing the potency and breadth of activity not only by varying the composition of these loops but by also varying the length of these loops. In terms of making improvements one could first start by deletion of the amino acid extensions in the parental CDR1 loop and even replacement with a corresponding shorter germline CDR1 peptide sequence and/or through the generation intermediate length loops, or diversified collections thereof, as shown above (lower left panel). Still if the extended loop is beneficial, but not entirely optimal, one would consider extending the loop by insertion of (1-20) random or selected amino acids within CDR1, the FR1 junction, and/or the FR2 junctions of CDR1 in a stepwise and combinatorial fashion. By creating a combinatorial library of such antibodies with extended loop lengths one could discriminately screen for better and broader binders to both susceptible and unsusceptible influenza isolates, strains, and types.

Figure 8:
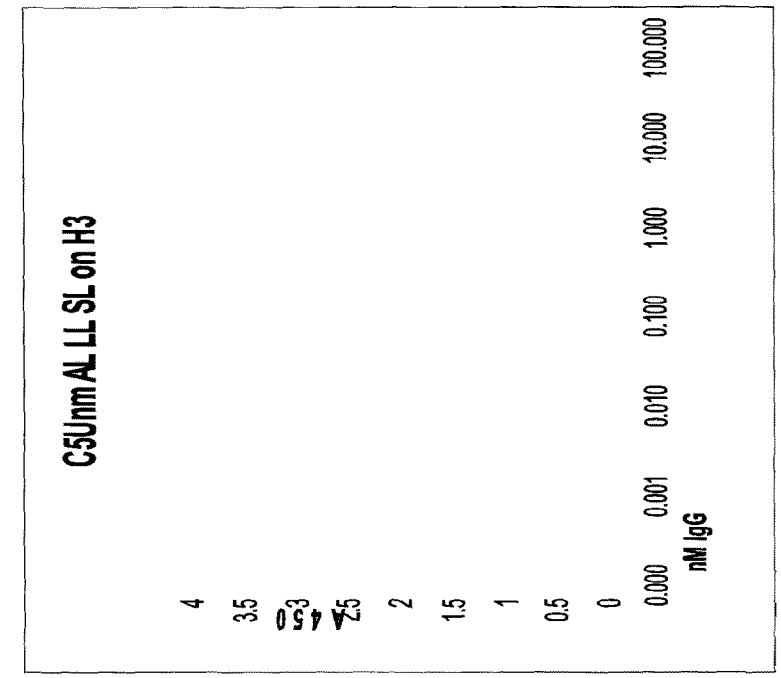
FIG. 8 illustrates that C05 variants maintain recognition of H1 and H3 HA proteins.
Figure 8:
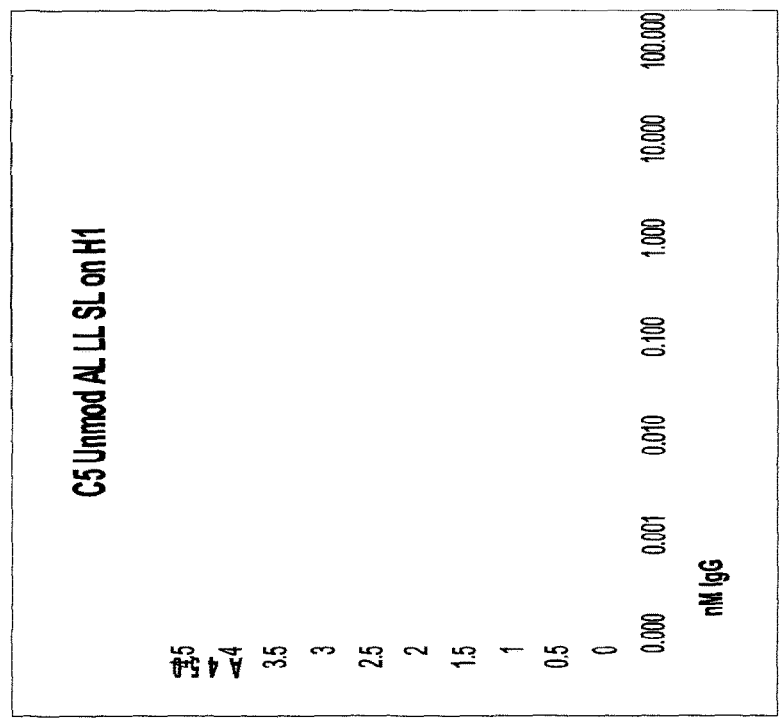

In addition, the C05 antibody is marked by a longer than typical heavy chain CDR3 (SEQ ID NO:9) loop of 25 amino acids. Similar to the CDR1 insertion and deletions examples described above, the CDR3 region can be similarly modified. As shown below (lower right panel), the CDR3 sequences could be similarly contracted or expanded, by 1-20 amino acids, within the loops or at the FR3 and FR4 junctions of CDR3 in a step wise combinatorial fashion (genomic sequence of C05 is shown).

nines were essential by generating double point mutations that substituted alanine, leucine, or serine for methionine at Kabat residue 96, and a leucine for methionine at Kabat residue 98. The corresponding proteins were produced in transient mammalian systems and purified as previously described (Kashyap A K et al. supra 2008). The resulting proteins were tested for binding to the H1 (New Caledonia/20/99) hemagglutinin and found to bind within a fold of the parental protein. Next these proteins were test for their ability to bind H3 (Wisconsin/67/2005) hemagglutinin, which showed the leucine 96/leucine 98 variant bound substantially better than the alanine 96/leucine 98 and the serine 96/leucine 98 variants. FIG. 8 illustrates that C05 nonoxidizable "XL" variants maintain recognition of H1 and H3 HA proteins.

Figure 9:
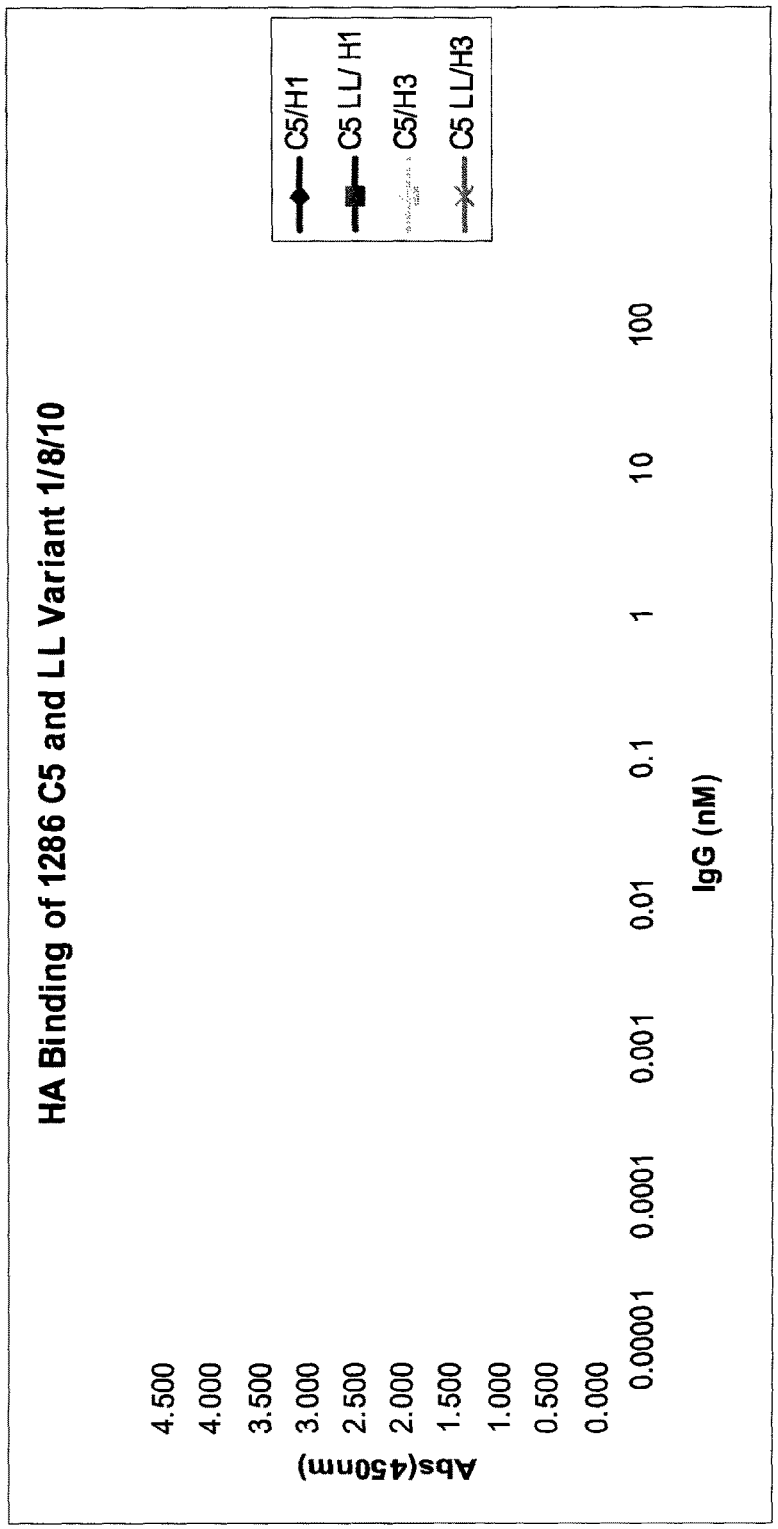
FIG. 9 illustrates that C05 variants maintain recognition of H1 and H3 HA proteins.

FIG. 9 shows the binding of a leucine 96/leucine 98 C05 variant to H1 (New Caledonia/20/99) and H3 (Wisconsin/67/2005) hemagglutinin, as compared to binding of non-variant C05 to H1 and H3. The C05 nonoxidizable "LL" variant maintain recognition of H1 and H3 HA proteins.

Table 3 illustrates that the C05-LL variant displayed similar potency and breadth of activity, as tested by hemagglutination inhibition (HAI) assays, where hemagglutination and the hemagglutination inhibition assays were essentially as described by Edwards and Dimmock, (Journal of Virology, v75, pp. 10208-18, 2001) and where recombinogenic virus was generated as described by Kashyap, et. al. (2008) supra. The values represent minimum concentration of antibody inhibiting hemagglutination of 0.5% cRBCs.

TABLE 3

| Subtype | Strain | Activity with 1286 C05 | Activity with 1286 C5 LL variant |
| --- | --- | --- | --- |
| Pandemic H1N1 | (SOIV) A/Cal/04/09 (6:2) | No Activity (>100 ug/ml) | No Activity (>100 ug/ml) |
| Seasonal | A/New Cal/99 | <0.1 ug/ml | 0.39 ug/ml |

```
                CDR2                                                           CDR3
VH3 3-23  EWVSAISGSGGSTYYADSVKGRFTISRDNSKNTLYLQMNSLRAEDTAVYYCAKHMSMQQVVSAGWERADLVGDAFDVWGQGTMVTVSS
    C05   EWLSIINAGGGDIDYADSVEGRFTISRDNSKETLYLQMTNLRVEDTGVYYCAK-------------------AFDIWGQGTMVTVSS  JH3

CDR3 Insertions
C05-based
    AKHMSMQQVVSAGWERADLVGDAFD
(X)ₘAKHMSMQQVVSAGWERADLVGDAFD
    AKHMSMQQVVSAGWERADLVGDAFD(Y)ₙ
(X)ₘAKHMSMQQVVSAGWERADLVGDAFD(Y)ₙ
```

By analogy to other mutually beneficial mutagenesis the varied loop length CDR1 and CDR3 libraries could be combined to interrogate novel and more broadly potent anti-influenza antibodies against the currently susceptible and unsusceptible influenza isolates, strains, and types. Importantly, these strategies could also be applied not only to the parental C05 CDRs, but also to the Vh3-23 germline or other Vh germline CDR1 loop crossed into the antibody of interest.

Example 8—Variants with Decreased Oxidative Heterogeneity Potential

The antibody 1286-C05 contains two methionines within the heavy chain CDR3 loop at Kabat residues 96 and 98. By definition this loop is surface exposed and therefore susceptible to oxidation. We tested whether either or both methio- TABLE 3-continued

| Subtype | Strain | Activity with 1286 C05 | Activity with 1286 C5 LL variant |
| --- | --- | --- | --- |
| H1N1 | A/Texas/91 | No Activity (>100 ug/ml) | No Activity (>100 ug/ml) |
|  | A/Bris/59/07 | 1.56 ug/ml | 3.12 ug/ml |
|  | A/Sol Is/06 | 1.56 ug/ml | 3.12 ug/ml |
|  | A/Virginia/87 | No Activity (>100 ug/ml) | No Activity (>100 ug/ml) |
| Seasonal H3N2 | A/Wisc/05 | <0.1 ug/ml | <0.1 ug/ml |
|  | A/HK/68 | <0.1 ug/ml | 0.39 ug/ml |
|  | A/Bris/10/07 | 12.5 ug/ml | 12.5 ug/ml |
|  | A/Pan/99 | 0.39 ug/ml | 0.19 ug/ml |

Example 8—Generating Variants with Increased Affinity and Breadth of Activity Various methods of mutagenesis are used to create improved variants for testing either individually or amongst a collection in a library. Methods commonly used to introduce beneficial mutations at sites responsible for binding, such as the CDRs or those contact residues found specifically through direct structural analysis would be, but not limited to, saturation mutagenesis, Look through mutagenesis, or parsimonious mutagenesis.

As a directed step one would create a collection of variants based upon mutagenesis of the CDR3 by the methods mentioned above. Previous work with other human antibodies have shown tremendous benefits by exploring and generating point variants to the light chain, other heavy chain CDRs, or even simultaneously to several or all of these areas at one time to produce synergistic improvements. Usually one can accomplish this by maintaining the parental framework and length of the CDRs, while varying only the composition of the CDRs. Conversely error-prone PCR mutagenesis and other stochastic processes could be used throughout similar regions and also in other areas of the heavy chain variable domain to generate collections of variants. In any event the resulting collections or clones could be selected for increased affinity, neutralization, and or breadth of activity.

As described above we would generate such optimization collections, but because the heavy chain is marked by such unique loop lengths in both CDR1 and CDR3 it could be of even greater importance to test the potency and breadth of activity not just by varying the composition of these loops, but also by varying the length of these loops. For example, we would test the effects of the extended CDR1 loop by replacement with the corresponding shorter germline CDR1 peptide sequence and/or a mutated collection. In addition insertion of random amino acids within CDR1, or at the FR1 and FR2 junctions of CDR1 in a stepwise library fashion, until the loop matches, and even exceeds the existing extended loop length could be made and discriminately screened for better and broader binders. of. Similarly the CDR3 sequences could be contracted or expanded within the loops or at the FR3 and FR4 junctions of CDR3 in a step wise library fashion. By analogy to other mutually beneficial mutagenesis the varied loop length CDR1 and CDR3 libraries could be combined to interrogate novel and more broadly potent anti-influenza antibodies.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All references cited throughout the specification are hereby expressly incorporated by reference in their entirety.

What is claimed is:

1. An antibody that binds an influenza virus comprising a heavy chain, the heavy chain comprising the hypervariable region sequences of SEQ ID NO:7, SEQ ID NO:8, and SEQ ID NO:9; and (b) a light chain comprising the hypervariable region sequences of SEQ ID NO: 13, SEQ ID NO: 14, and SEQ ID NO: 15; wherein the antibody (i) neutralizes more than one subtype or more than one isolate of an influenza A virus, (ii) binds to a hemagglutinin antigen (HA) of the virus, and (iii) inhibits hemagglutination.

2. The antibody of claim 1, wherein the heavy chain comprises the amino acid sequence of SEQ ID NO: 1.

3. The antibody of claim 2, wherein the light chain comprises the amino acid sequence of SEQ ID NO:5.

4. The antibody of claim 1, which prevents the globular head region of the influenza A virus from binding and attaching to the surface of a cell.

5. A composition comprising the antibody of claim 1.

6. The antibody of claim 1, wherein the heavy chain comprises the amino acid sequence of SEQ ID NO: 1 and wherein the light chain comprises the amino acid sequence of SEQ ID NO: 5.

7. The antibody of claim 6, which binds to an H1 HA antigen, and optionally binds to at least one additional HA antigen, wherein the additional HA antigen is selected from an H3 HA antigen and an H9 HA antigen.

8. The antibody of claim 7, wherein the H1 HA is from a New Caledonia/20/99 isolate or a Solomon Islands/3/06 isolate of the H1 virus.

9. The antibody of claim 7, wherein the H3 HA is from a Wisconsin/67/05 isolate or a Hong Kong/68 isolate of the H3 virus.

10. The antibody of claim 7, wherein the H9 HA is from, a Hong Kong/1073/99 isolate of the H9 virus.

11. The antibody of claim 1, wherein at least one of the influenza virus isolates has the ability to infect humans.

* * * * *

SEQUENCE LISTING

```
<160> NUMBER OF SEQ ID NOS: 29

<210> SEQ ID NO 1
<211> LENGTH: 138
<212> TYPE: PRT
<213> ORGANISM: Homo sapiens

<400> SEQUENCE: 1

Gln Val Gln Leu Gln Glu Ser Gly Gly Gly Leu Val Gln Pro Gly Glu
1               5                   10                  15

Ser Leu Arg Leu Ser Cys Val Gly Ser Gly Ser Ser Phe Gly Glu Ser
            20                  25                  30

Thr Leu Ser Tyr Tyr Ala Val Ser Trp Val Arg Gln Ala Pro Gly Lys
        35                  40                  45

Gly Leu Glu Trp Leu Ser Ile Ile Asn Ala Gly Gly Gly Asp Ile Asp
    50                  55                  60

Tyr Ala Asp Ser Val Glu Gly Arg Phe Thr Ile Ser Arg Asp Asn Ser
65                  70                  75                  80

Lys Glu Thr Leu Tyr Leu Gln Met Thr Asn Leu Arg Val Glu Asp Thr
                85                  90                  95

Gly Val Tyr Tyr Cys Ala Lys His Met Ser Met Gln Gln Val Val Ser
            100                 105                 110

Ala Gly Trp Glu Arg Ala Asp Leu Val Gly Asp Ala Phe Asp Val Trp
        115                 120                 125

Gly Gln Gly Thr Met Val Thr Val Ser Ser
    130                 135

<210> SEQ ID NO 2
<211> LENGTH: 127
<212> TYPE: PRT
<213> ORGANISM: Homo sapiens
```

<400> SEQUENCE: 2

Gln Val Gln Leu Gln Gln Ser Gly Pro Arg Leu Val Lys Pro Ser Gln
1               5                   10                  15
Thr Leu Ser Leu Thr Cys Ala Ile Ser Gly Asp Ser Val Ser Gly Asp
            20                  25                  30
Ser Gly Thr Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
Glu Ser Val Lys Ser Arg Ile Val Ile Lys Ala Asp Thr Ser Lys Asn
65                  70                  75                  80
Glu Phe Ser Leu Gln Leu Asn Ser Val Thr Pro Glu Asp Thr Ala Ile
                85                  90                  95
Tyr Tyr Cys Ala Arg Ala Gly Val Lys Ile Phe Gly Leu Ile Val Gly
            100                 105                 110
Ala Leu Asp Asn Trp Gly Arg Gly Thr Leu Val Thr Val Ser Ser
        115                 120                 125

<210> SEQ ID NO 3
<211> LENGTH: 112
<212> TYPE: PRT
<213> ORGANISM: Homo sapiens

<400> SEQUENCE: 3

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Asp Asn Asn Asn Arg Pro Ser Gly Val Pro Asp Arg Phe
    50                  55                  60
Ser Gly Ser Lys Ser Gly Ala Ser Ala Ser Leu Ala Ile Thr Gly Leu
65                  70                  75                  80
Gln Ala Glu Asp Glu Ala His Tyr Tyr Cys Gln Ser Tyr Asp Asn Ser
                85                  90                  95
Leu Ser Gly Ser Val Phe Gly Gly Gly Thr Gln Leu Thr Val Leu Ser
            100                 105                 110

<210> SEQ ID NO 4
<211> LENGTH: 107
<212> TYPE: PRT
<213> ORGANISM: Homo sapiens

<400> SEQUENCE: 4

Asp Ile Gln Leu Thr Gln Ser Pro Ser Ser Leu Ser Ala Ser Val Gly
1               5                   10                  15
Asp Arg Val Thr Leu Thr Cys Gln Ala Ser Gln Asp Ile Arg Lys Phe
            20                  25                  30
Leu Asn Trp Tyr Gln Gln Lys Pro Gly Lys Gly Pro Lys Leu Leu Ile
        35                  40                  45
Tyr Asp Ala Ser Asn Leu Gln Arg Gly Val Pro Ser Arg Phe Ser Gly
    50                  55                  60
Gly Gly Ser Gly Thr Asp Phe Thr Leu Ile Ile Ser Ser Leu Gln Pro
65                  70                  75                  80
Glu Asp Val Gly Thr Tyr Tyr Cys Gln Gln Tyr Asp Gly Leu Pro Phe

Thr Phe Gly Gly Gly Thr Lys Leu Glu Ile Lys
                100                 105

<210> SEQ ID NO 5
<211> LENGTH: 107
<212> TYPE: PRT
<213> ORGANISM: Homo sapiens

<400> SEQUENCE: 5

Asp Ile Gln Leu Thr Gln Ser Pro Ser Ser Leu Ser Ala Ser Ile Gly
1               5                   10                  15

Asp Arg Val Thr Ile Thr Cys Gln Ala Ser Gln Asp Ile Arg Asn Ser
            20                  25                  30

Leu Asn Trp Tyr Glu His Lys Pro Gly Lys Ala Pro Lys Leu Leu Ile
        35                  40                  45

His Asp Ala Ser Asn Leu Glu Thr Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
                100                 105

<210> SEQ ID NO 6
<211> LENGTH: 109
<212> TYPE: PRT
<213> ORGANISM: Homo sapiens

<400> SEQUENCE: 6

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Val Pro Asp Arg Phe His
    50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Thr Ser Ser
                85                  90                  95

Gly Leu Thr Phe Gly Gly Gly Thr Lys Val Glu Ile Lys
                100                 105

<210> SEQ ID NO 7
<211> LENGTH: 11
<212> TYPE: PRT
<213> ORGANISM: Homo sapiens

<400> SEQUENCE: 7

Gly Glu Ser Thr Leu Ser Tyr Tyr Ala Val Ser
1               5                   10

<210> SEQ ID NO 8
<211> LENGTH: 13
<212> TYPE: PRT
<213> ORGANISM: Homo sapiens

<400> SEQUENCE: 8

Trp Leu Ser Ile Ile Asn Ala Gly Gly Gly Asp Ile Asp
1               5                   10

<210> SEQ ID NO 9
<211> LENGTH: 25
<212> TYPE: PRT
<213> ORGANISM: Homo sapiens

<400> SEQUENCE: 9

Ala Lys His Met Ser Met Gln Gln Val Val Ser Ala Gly Trp Glu Arg
1               5                   10                  15

Ala Asp Leu Val Gly Asp Ala Phe Asp
            20                  25

<210> SEQ ID NO 10
<211> LENGTH: 8
<212> TYPE: PRT
<213> ORGANISM: Homo sapiens

<400> SEQUENCE: 10

Ser Gly Asp Ser Gly Thr Trp Asn
1               5

<210> SEQ ID NO 11
<211> LENGTH: 14
<212> TYPE: PRT
<213> ORGANISM: Homo sapiens

<400> SEQUENCE: 11

Trp Leu Gly Arg Thr Tyr Tyr Arg Ser Lys Trp Tyr Asn Asp
1               5                   10

<210> SEQ ID NO 12
<211> LENGTH: 16
<212> TYPE: PRT
<213> ORGANISM: Homo sapiens

<400> SEQUENCE: 12

Ala Arg Ala Gly Val Lys Ile Phe Gly Leu Ile Val Gly Ala Leu Asp
1               5                   10                  15

<210> SEQ ID NO 13
<211> LENGTH: 10
<212> TYPE: PRT
<213> ORGANISM: Homo sapiens

<400> SEQUENCE: 13

Ile Gly Ala Gly Tyr Asp Val His Trp Tyr
1               5                   10

<210> SEQ ID NO 14
<211> LENGTH: 10
<212> TYPE: PRT
<213> ORGANISM: Homo sapiens

<400> SEQUENCE: 14

Leu Leu Ile Tyr Asp Asn Asn Asn Arg Pro
1               5                   10

<210> SEQ ID NO 15
<211> LENGTH: 10
<212> TYPE: PRT

<213> ORGANISM: Homo sapiens

<400> SEQUENCE: 15

Gln Ser Tyr Asp Asn Ser Leu Ser Gly Ser
1               5                   10

<210> SEQ ID NO 16
<211> LENGTH: 8
<212> TYPE: PRT
<213> ORGANISM: Homo sapiens

<400> SEQUENCE: 16

Ile Arg Lys Phe Leu Asn Trp Tyr
1               5

<210> SEQ ID NO 17
<211> LENGTH: 10
<212> TYPE: PRT
<213> ORGANISM: Homo sapiens

<400> SEQUENCE: 17

Leu Leu Ile Tyr Asp Ala Ser Asn Leu Gln
1               5                   10

<210> SEQ ID NO 18
<211> LENGTH: 8
<212> TYPE: PRT
<213> ORGANISM: Homo sapiens

<400> SEQUENCE: 18

Gln Gln Tyr Asp Gly Leu Pro Phe
1               5

<210> SEQ ID NO 19
<211> LENGTH: 8
<212> TYPE: PRT
<213> ORGANISM: Homo sapiens

<400> SEQUENCE: 19

Ile Arg Asn Ser Leu Asn Trp Tyr
1               5

<210> SEQ ID NO 20
<211> LENGTH: 10
<212> TYPE: PRT
<213> ORGANISM: Homo sapiens

<400> SEQUENCE: 20

Leu Leu Ile His Asp Ala Ser Asn Leu Glu
1               5                   10

<210> SEQ ID NO 21
<211> LENGTH: 8
<212> TYPE: PRT
<213> ORGANISM: Homo sapiens

<400> SEQUENCE: 21

Gln Gln Ala Asn Ser Phe Pro Leu
1               5

<210> SEQ ID NO 22
<211> LENGTH: 7
<212> TYPE: PRT
<213> ORGANISM: Homo sapiens

```
<400> SEQUENCE: 22

Ser Ser Tyr Leu Ala Trp Tyr
1               5

<210> SEQ ID NO 23
<211> LENGTH: 10
<212> TYPE: PRT
<213> ORGANISM: Homo sapiens

<400> SEQUENCE: 23

Leu Leu Ile Tyr Gly Ala Ser Thr Arg Ala
1               5                   10

<210> SEQ ID NO 24
<211> LENGTH: 9
<212> TYPE: PRT
<213> ORGANISM: Homo sapiens

<400> SEQUENCE: 24

Gln Gln Tyr Asp Thr Ser Ser Gly Leu
1               5

<210> SEQ ID NO 25
<211> LENGTH: 25
<212> TYPE: PRT
<213> ORGANISM: Homo sapiens

<400> SEQUENCE: 25

Ala Lys His Met Ser Leu Gln Gln Val Val Ser Ala Gly Trp Glu Arg
1               5                   10                  15

Ala Asp Leu Val Gly Asp Ala Phe Asp
            20                  25

<210> SEQ ID NO 26
<211> LENGTH: 25
<212> TYPE: PRT
<213> ORGANISM: Homo sapiens

<400> SEQUENCE: 26

Ala Lys His Leu Ser Met Gln Gln Val Val Ser Ala Gly Trp Glu Arg
1               5                   10                  15

Ala Asp Leu Val Gly Asp Ala Phe Asp
            20                  25

<210> SEQ ID NO 27
<211> LENGTH: 25
<212> TYPE: PRT
<213> ORGANISM: Homo sapiens

<400> SEQUENCE: 27

Ala Lys His Ala Ser Leu Gln Gln Val Val Ser Ala Gly Trp Glu Arg
1               5                   10                  15

Ala Asp Leu Val Gly Asp Ala Phe Asp
            20                  25

<210> SEQ ID NO 28
<211> LENGTH: 25
<212> TYPE: PRT
<213> ORGANISM: Homo sapiens

<400> SEQUENCE: 28

Ala Lys His Ser Ser Leu Gln Gln Val Val Ser Ala Gly Trp Glu Arg
1               5                   10                  15
```

```
Ala Asp Leu Val Gly Asp Ala Phe Asp
            20                  25

<210> SEQ ID NO 29
<211> LENGTH: 25
<212> TYPE: PRT
<213> ORGANISM: Homo sapiens

<400> SEQUENCE: 29

Ala Lys His Leu Ser Leu Gln Gln Val Val Ser Ala Gly Trp Glu Arg
1               5                   10                  15

Ala Asp Leu Val Gly Asp Ala Phe Asp
            20                  25
```